(12) United States Patent
Kadoma et al.

(10) Patent No.: US 11,641,777 B2
(45) Date of Patent: May 2, 2023

(54) DIBENZO[C,G]CARBAZOLE DERIVATIVE, LIGHT-EMITTING DEVICE, LIGHT-EMITTING APPARATUS, ELECTRONIC DEVICE, AND LIGHTING DEVICE

(71) Applicant: Semiconductor Energy Laboratory Co., Ltd., Kanagawa-ken (JP)

(72) Inventors: Hiroshi Kadoma, Kanagawa (JP); Tsunenori Suzuki, Kanagawa (JP); Naoaki Hashimoto, Kanagawa (JP); Yusuke Takita, Kanagawa (JP); Satoshi Seo, Kanagawa (JP)

(73) Assignee: Semiconductor Energy Laboratory Co., Ltd.

( * ) Notice: Subject to any disclaimer, the term of this patent is extended or adjusted under 35 U.S.C. 154(b) by 237 days.

(21) Appl. No.: 16/764,715

(22) PCT Filed: Nov. 12, 2018

(86) PCT No.: PCT/IB2018/058851
§ 371 (c)(1),
(2) Date: May 15, 2020

(87) PCT Pub. No.: WO2019/102292
PCT Pub. Date: May 31, 2019

(65) Prior Publication Data
US 2021/0175435 A1    Jun. 10, 2021

(30) Foreign Application Priority Data
Nov. 24, 2017  (JP) .............................. JP2017-225741

(51) Int. Cl.
*C07D 209/80* (2006.01)
*H01L 51/00* (2006.01)
*C09K 11/06* (2006.01)
*H01L 51/50* (2006.01)

(52) U.S. Cl.
CPC ........ *H01L 51/0072* (2013.01); *C07D 209/80* (2013.01); *C09K 11/06* (2013.01); *H01L 51/0052* (2013.01); *C09K 2211/1018* (2013.01); *H01L 51/5012* (2013.01); *H01L 51/5056* (2013.01)

(58) Field of Classification Search
CPC .................................................. C07D 209/80
See application file for complete search history.

(56) References Cited

U.S. PATENT DOCUMENTS

| 8,841,655 | B2 | 9/2014 | Okamoto |
| 8,986,857 | B2 | 3/2015 | Suzuki et al. |
| 9,240,558 | B2 | 1/2016 | Suzuki et al. |
| 9,997,723 | B2 | 6/2018 | Kang et al. |
| 10,186,669 | B2 | 1/2019 | Kang et al. |
| 10,886,474 | B2 | 1/2021 | Moon et al. |
| 2013/0020561 | A1 | 1/2013 | Suzuki et al. |
| 2015/0171347 | A1 | 6/2015 | Suzuki et al. |

FOREIGN PATENT DOCUMENTS

| CN | 103052624 A | 4/2013 |
| CN | 106187859 A | 12/2016 |
| CN | 106414428 A | 2/2017 |
| CN | 107056737 A | 8/2017 |

(Continued)

OTHER PUBLICATIONS

International Search Report (Application No. PCT/IB2018/058851) dated Feb. 5, 2019.

(Continued)

*Primary Examiner* — Shawquia Jackson
(74) *Attorney, Agent, or Firm* — Husch Blackwell LLP

(57) ABSTRACT

An object is to provide a novel organic compound. Another object is to provide a novel light-emitting device. Another object is to provide a light-emitting device with favorable emission efficiency. Another object is to provide a light-emitting device with a favorable lifetime. Another object is to provide a light-emitting device with a low driving voltage. A dibenzo[c,g]carbazole derivative represented by the following general formula (G1) and a light-emitting device using it are provided. Note that at least one of $R^{11}$ to $R^{22}$ represents a substituent that has 14 to 60 carbon atoms in total and contains a condensed tricyclic to hexacyclic aromatic hydrocarbon skeleton, and the others independently represent any of hydrogen, an alkyl group having 1 to 6 carbon atoms, a cycloalkyl group having 3 to 6 carbon atoms, and a substituted or unsubstituted aryl group having 6 to 25 carbon atoms.

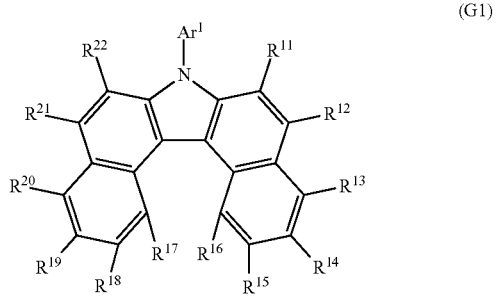

(G1)

19 Claims, 34 Drawing Sheets

(56) References Cited

FOREIGN PATENT DOCUMENTS

| | | | |
|---|---|---|---|
| CN | 107074764 A | | 8/2017 |
| CN | 107602467 A | | 1/2018 |
| CN | 107652221 A | | 2/2018 |
| CN | 107698487 A | | 2/2018 |
| CN | 107721903 A | * 2/2018 | ........... C07D 209/80 |
| CN | 107721903 A | | 2/2018 |
| DE | 112012003073 | | 11/2014 |
| DE | 112012005831 | | 6/2015 |
| JP | 2013-047283 A | | 3/2013 |
| JP | 2013-048221 A | | 3/2013 |
| JP | 2013-100341 A | | 5/2013 |
| JP | 2016-219827 A | | 12/2016 |
| JP | 2017-046000 A | | 3/2017 |
| JP | 2018-085525 A | | 5/2018 |
| KR | 2010-0108924 A | | 10/2010 |
| KR | 2014-0015259 A | | 2/2014 |
| KR | 2014-0026577 A | | 3/2014 |
| KR | 2015-0004099 A | | 1/2015 |
| KR | 10-1535606 | | 7/2015 |
| TW | 201105774 | | 2/2011 |
| TW | 201313682 | | 4/2013 |
| TW | 201706245 | | 2/2017 |
| WO | WO-2010/114264 | | 10/2010 |
| WO | WO-2011/065136 | | 6/2011 |
| WO | WO-2013/015144 | | 1/2013 |
| WO | WO 2015/178731 A1 | | 11/2015 |
| WO | WO 2016/048109 A1 | | 3/2016 |
| WO | WO-2016/122150 | | 8/2016 |

OTHER PUBLICATIONS

Written Opinion (Application No. PCT/IB2018/058851) dated Feb. 5, 2019.

Chinese Office Action (Application No. 201880075855.7) dated Feb. 11, 2023.

\* cited by examiner

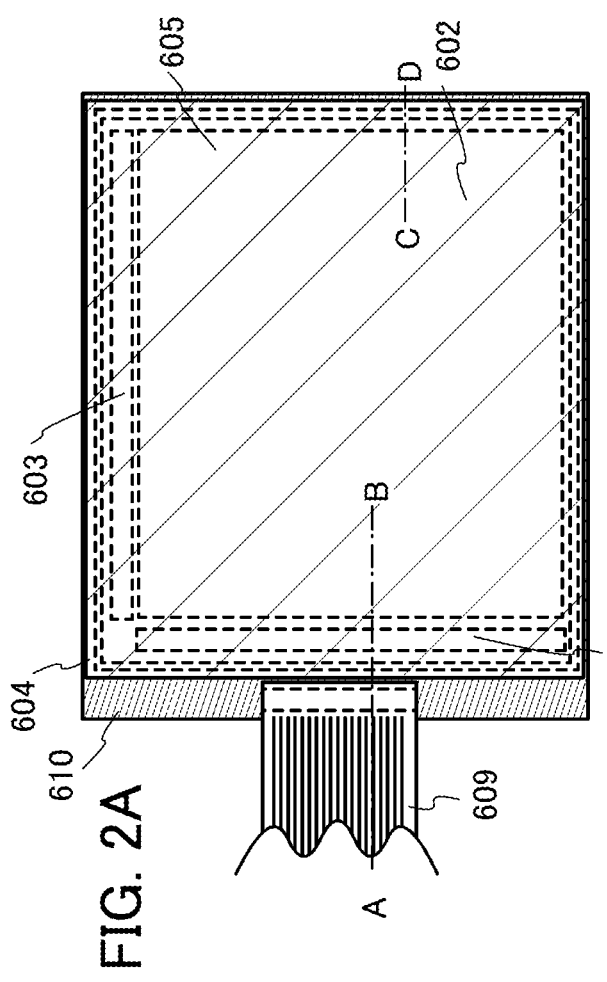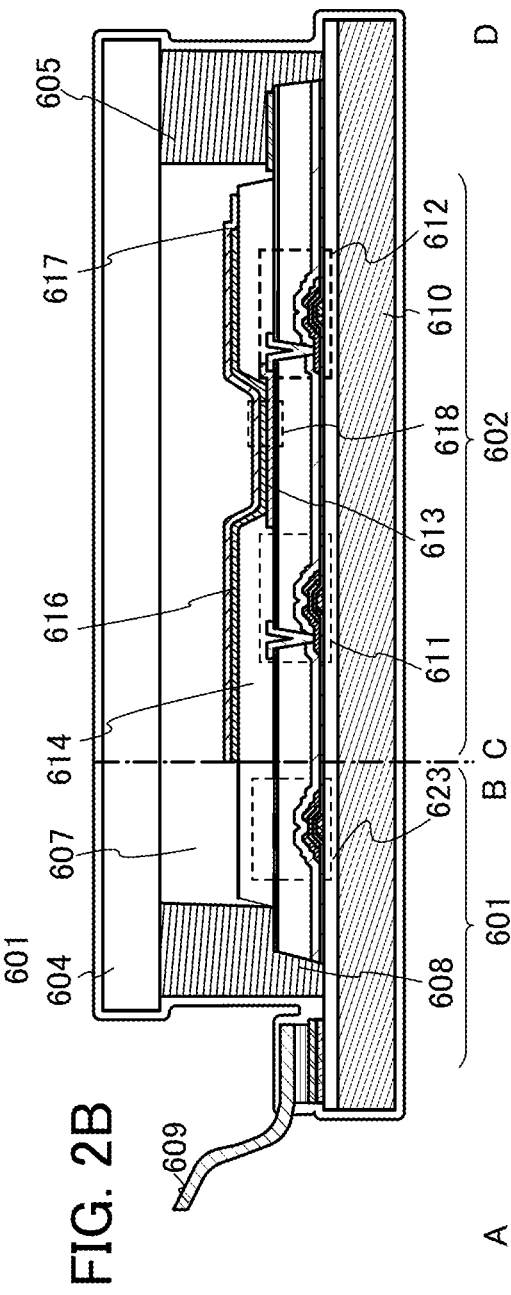

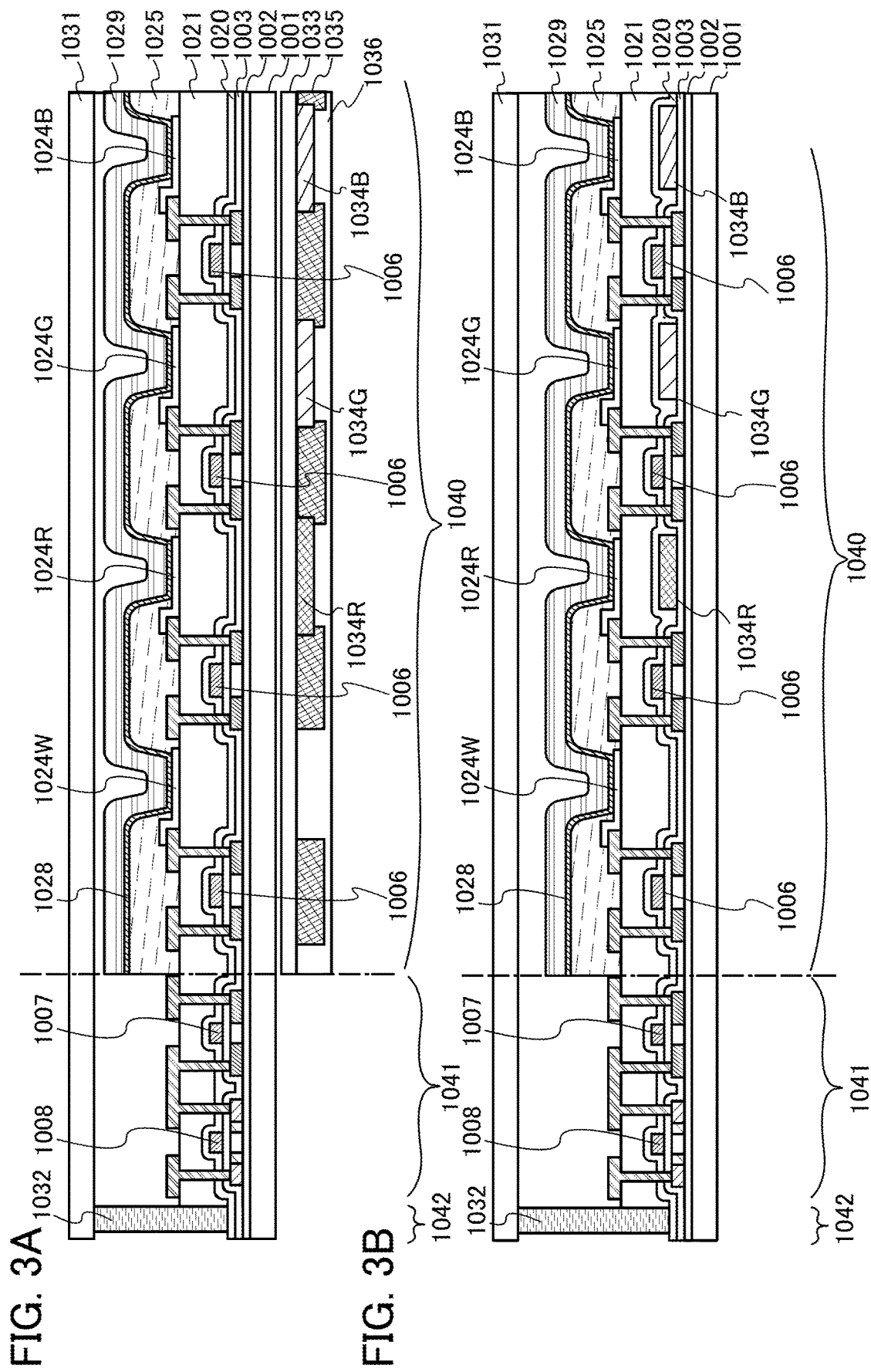

FIG. 7A
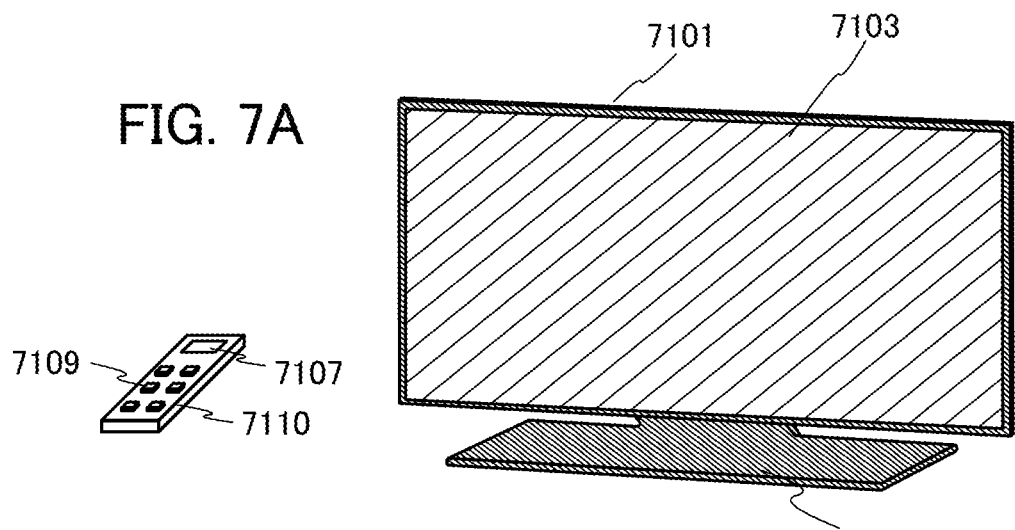
FIG. 7B1
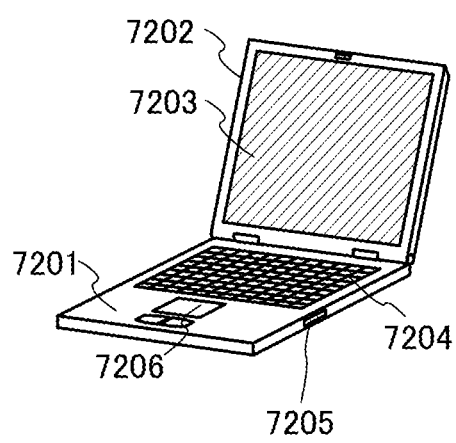
FIG. 7B2
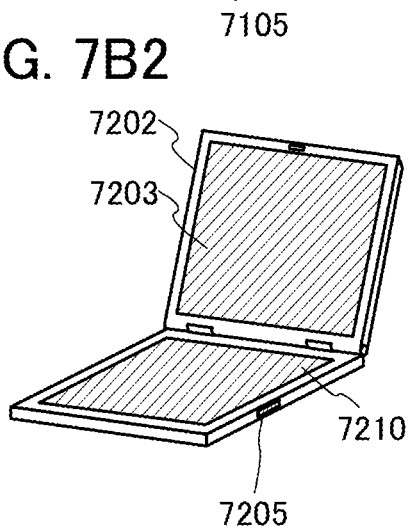
FIG. 7C
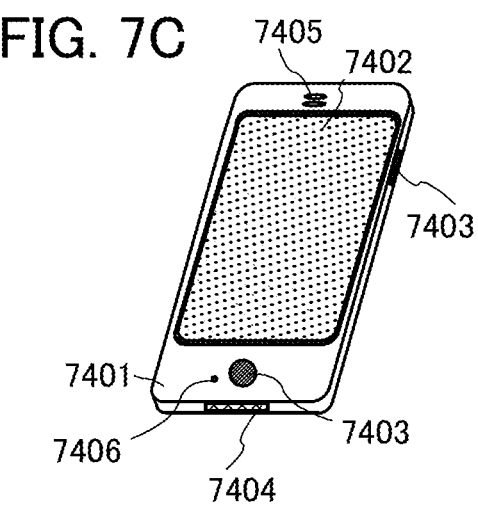

DIBENZO[C,G]CARBAZOLE DERIVATIVE, LIGHT-EMITTING DEVICE, LIGHT-EMITTING APPARATUS, ELECTRONIC DEVICE, AND LIGHTING DEVICE

This application is a 371 of international application PCT/IB2018/058851 filed on Nov. 12, 2018 which is incorporated herein by reference.

TECHNICAL FIELD

One embodiment of the present invention relates to a light-emitting device, a display module, a lighting module, a display device, a light-emitting apparatus, an electronic device, and a lighting device. Note that one embodiment of the present invention is not limited to the above technical field. The technical field of one embodiment of the invention disclosed in this specification and the like relates to an object, a method, or a manufacturing method. Another embodiment of the present invention relates to a process, a machine, manufacture, or a composition of matter. Thus, more specifically, a semiconductor device, a display device, a liquid crystal display device, a light-emitting apparatus, a lighting device, a power storage device, a memory device, an imaging device, a driving method thereof, or a manufacturing method thereof can be given as an example of the technical field of one embodiment of the present invention disclosed in this specification.

BACKGROUND ART

Light-emitting devices (organic EL devices) that use organic compounds and utilize electroluminescence (EL) have been put to more practical use. The basic structure of such a light-emitting device is a structure in which an organic compound layer containing a light-emitting material (an EL layer) is interposed between a pair of electrodes. Carriers are injected by application of voltage to this element, and recombination energy of the carriers is used, whereby light emission can be obtained from the light-emitting material.

Such light-emitting devices are of self-light-emitting type, and have advantages over liquid crystal such as high visibility and no need for backlight when used for pixels of a display; accordingly, the light-emitting devices are suitable as flat panel display devices. Displays using such light-emitting devices are also highly advantageous in that they can be fabricated to be thin and lightweight. Moreover, extremely fast response speed is also one of the features.

Since light-emitting layers of such light-emitting devices can be successively formed two-dimensionally, planar light emission can be obtained. This feature is difficult to realize with point light sources typified by incandescent lamps and LEDs or linear light sources typified by fluorescent lamps; thus, light-emitting devices also have great potential as planar light sources, which can be applied to lightings and the like.

Displays or lighting devices using light-emitting devices can be suitably used for a variety of electronic devices as described above, and research and development of light-emitting devices has progressed for more favorable efficiency or lifetimes.

An organic compound having an acceptor property can be given as a material for a hole-injection layer that is used to facilitate the injection of carriers, particularly holes, into an EL layer. The organic compound having an acceptor property, which can be easily deposited by evaporation, is suitable for mass production and has become widely used; however, the hole injection into an EL layer is difficult when the LUMO level of the organic compound having an acceptor property is at a distance from the HOMO level of an organic compound included in a hole-transport layer. When the HOMO level of the organic compound included in the hole-transport layer is made shallow so that the HOMO level of the organic compound included in the hole-transport layer is closer to the LUMO level of the organic compound having an acceptor property, the HOMO level becomes much different from the HOMO level of the light-emitting layer, causing difficulty in hole injection from the hole-transport layer into a host material in the light-emitting layer even when holes can be injected into the EL layer.

Patent Document 1 discloses a structure in which a hole-transport material, which has a HOMO level between the HOMO level of a first hole-injection layer and the HOMO level of a host material, is provided between a light-emitting layer and a first hole-transport layer in contact with the hole-injection layer.

The characteristics of light-emitting devices have been improved remarkably, but are still insufficient to satisfy advanced requirements for various characteristics including efficiency and durability.

REFERENCES

Patent Document

[Patent Document 1] PCT International Publication No. WO2011/065136

SUMMARY OF THE INVENTION

Problems to be Solved by the Invention

An object of one embodiment of the present invention is to provide a novel organic compound. Another object of one embodiment of the present invention is to provide a novel organic compound having a hole-transport property. Another object of one embodiment of the present invention is to provide a novel hole-transport material. Another object of one embodiment of the present invention is to provide a novel light-emitting device. Another object is to provide a light-emitting device with favorable emission efficiency. Another object is to provide a light-emitting device with a favorable lifetime. Another object of the present invention is to provide a light-emitting device with a low driving voltage.

Alternatively, an object of another embodiment of the present invention is to provide each of a light-emitting apparatus, an electronic device, and a display device with high reliability. Alternatively, an object of another embodiment of the present invention is to provide a light-emitting apparatus, an electronic device, and a display device each having low power consumption.

It is only necessary that at least one of the above-described objects be achieved in the present invention.

Means for Solving the Problems

One embodiment of the present invention is a dibenzo[c,g]carbazole derivative represented by the following general formula (G1).

[Chemical Formula 1]

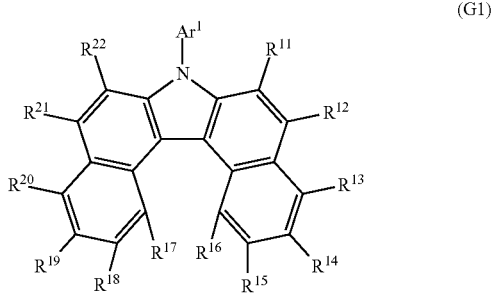

(G1)

Note that in the general formula (G1), at least one of $R^{11}$ to $R^{22}$ represents a substituent that has 14 to 60 carbon atoms in total and contains a condensed tricyclic to hexacyclic aromatic hydrocarbon, and the others independently represent any of hydrogen, an alkyl group having 1 to 6 carbon atoms, a cycloalkyl group having 3 to 6 carbon atoms, and a substituted or unsubstituted aryl group having 6 to 25 carbon atoms. Furthermore, $Ar^1$ represents a substituted or unsubstituted aryl group having 6 to 13 carbon atoms in a ring.

Another embodiment of the present invention is the dibenzo[c,g]carbazole derivative having the above structure in which $R^{12}$ represents a substituent that has 14 to 60 carbon atoms in total and contains a condensed tricyclic to hexacyclic aromatic hydrocarbon.

Alternatively, another embodiment of the present invention is the dibenzo[c,g]carbazole derivative in which the condensed tricyclic to hexacyclic aromatic hydrocarbon is any of a substituted or unsubstituted anthryl group, a substituted or unsubstituted phenanthryl group, and a substituted or unsubstituted triphenylenyl group, in the above structure.

Alternatively, another embodiment of the present invention is a dibenzo[c,g]carbazole derivative represented by the following general formula (G2).

[Chemical Formula 2]

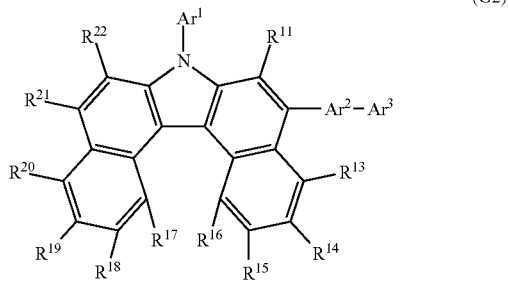

(G2)

Note that in the general formula (G2), $Ar^2$ represents a substituted or unsubstituted arylene group having 6 to 25 carbon atoms in a ring, and $Ar^3$ represents a substituent containing a condensed bicyclic to hexacyclic aromatic hydrocarbon. Note that the total number of carbon atoms contained in $Ar^2$ and $Ar^3$ is greater than or equal to 14 and less than or equal to 60. Furthermore, $R^{11}$ and $R^{13}$ to $R^{22}$ independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $Ar^1$ represents a substituted or unsubstituted aryl group having 6 to 13 carbon atoms in a ring.

Alternatively, another embodiment of the present invention is the dibenzo[c,g]carbazole derivative having the above structure in which the $Ar^3$ represents any one of a substituted or unsubstituted naphthyl group, a substituted or unsubstituted anthryl group, a substituted or unsubstituted phenanthryl group, and a substituted or unsubstituted triphenylenyl group.

Alternatively, another embodiment of the present invention is a dibenzo[c,g]carbazole derivative represented by the following general formula (G3).

[Chemical Formula 3]

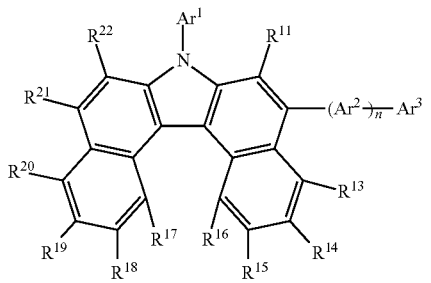

(G3)

Note that in the general formula (G3), $Ar^2$ represents a substituted or unsubstituted arylene group having 6 to 25 carbon atoms in a ring, and $Ar^3$ represents any one of a substituted or unsubstituted anthryl group, a substituted or unsubstituted phenanthryl group, and a substituted or unsubstituted triphenylenyl group. Furthermore, n represents an integer of 0 to 3, and the total number of carbon atoms contained in $Ar^2$ and $Ar^3$ is greater than or equal to 14 and less than or equal to 60. Furthermore, $R^{11}$ and $R^{13}$ to $R^{22}$ independently represent any of hydrogen, an alkyl group having 1 to 6 carbon atoms, a cycloalkyl group having 3 to 6 carbon atoms, and a substituted or unsubstituted aryl group having 6 to 13 carbon atoms. Furthermore, $Ar^1$ represents a substituted or unsubstituted aryl group having 6 to 13 carbon atoms in a ring.

Alternatively, another structure of the present invention is the dibenzo[c,g]carbazole derivative having the above structure in which n is 1.

Alternatively, another embodiment of the present invention is the dibenzo[c,g]carbazole derivative having the above structure in which $Ar^2$ is a substituted or unsubstituted phenylene group.

Alternatively, another embodiment of the present invention is the dibenzo[c,g]carbazole derivative having the above structure in which $Ar^3$ is an anthryl group including a phenyl group as a substituent.

Alternatively, another embodiment of the present invention is the dibenzo[c,g]carbazole derivative having the above structure in which $Ar^3$ is a phenanthryl group.

Alternatively, another embodiment of the present invention is the dibenzo[c,g]carbazole derivative having the above structure in which $Ar^1$ is a substituted or unsubstituted phenyl group.

Alternatively, another embodiment of the present invention is the dibenzo[c,g]carbazole derivative having the above structure in which $R^{11}$ and $R^{13}$ to $R^{22}$ are each hydrogen.

Alternatively, another embodiment of the present invention is a dibenzo[c,g]carbazole derivative represented by the following structural formula (100).

[Chemical Formula 4]

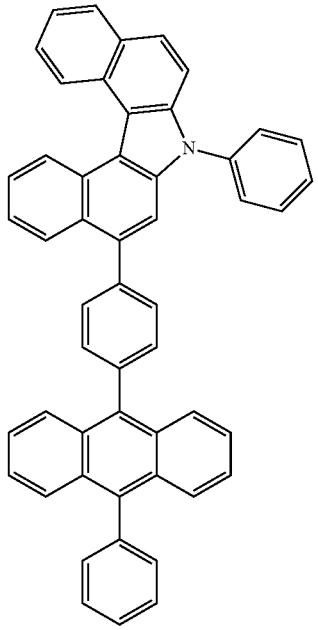
(100)

Alternatively, another embodiment of the present invention is a dibenzo[c,g]carbazole derivative represented by the following structural formula (101).

[Chemical Formula 5]

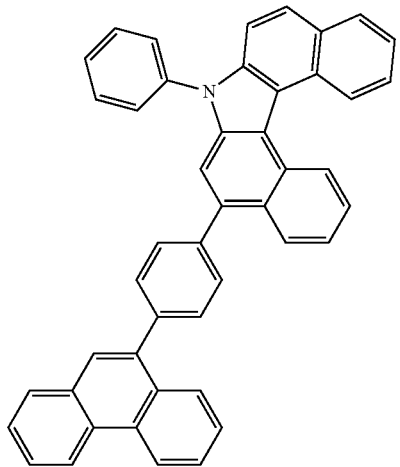
(101)

Alternatively, another embodiment of the present invention is a material for a light-emitting device containing the dibenzo[c,g]carbazole derivative having the above structure.

Alternatively, another embodiment of the present invention is a light-emitting device containing the dibenzo[c,g] carbazole derivative having the above structure.

Alternatively, another embodiment of the present invention is a light-emitting device containing the dibenzo[c,g] carbazole derivative described in any one of claim 1 to claim 15 between an anode and a light-emitting layer.

Alternatively, another embodiment of the present invention is a light-emitting device containing the dibenzo[c,g] carbazole derivative having the above structure in a light-emitting layer.

Alternatively, another embodiment of the present invention is a light-emitting apparatus including the light-emitting device having the above structure and a transistor or a substrate.

Alternatively, another embodiment of the present invention is an electronic device including the above light-emitting apparatus, and a sensor, an operation button, a speaker, or a microphone.

Alternatively, another embodiment of the present invention is a lighting device including the light-emitting apparatus having the above structure and a housing.

Note that the light-emitting apparatus in this specification includes an image display apparatus using a light-emitting device. In some cases, a module in which a light-emitting device is provided with a connector such as an anisotropic conductive film or a TCP (Tape Carrier Package), a module in which a printed wiring board is provided at the end of a TCP, or a module in which an IC (integrated circuit) is directly mounted on a light-emitting device by a COG (Chip On Glass) method includes the light-emitting apparatus. Furthermore, in some cases, lighting device or the like includes the light-emitting apparatus.

Effect of the Invention

In one embodiment of the present invention, in one embodiment of the present invention, a novel organic compound can be provided. Alternatively, in one embodiment of the present invention, a novel organic compound having a hole-transport property can be provided. Alternatively, in one embodiment of the present invention, a novel hole-transport material can be provided. One embodiment of the present invention can provide a novel light-emitting device. Alternatively, a light-emitting device with a favorable lifetime can be provided. Alternatively, a light-emitting device with favorable emission efficiency can be provided.

Alternatively, in one embodiment of the present invention, a light-emitting apparatus, an electronic device, and a display device each having high reliability can be provided. Alternatively, in one embodiment of the present invention, a light-emitting apparatus, an electronic device, and a display device each having low power consumption can be provided.

Note that the descriptions of these effects do not disturb the existence of other effects. Note that one embodiment of the present invention does not necessarily have all the effects listed above. Effects other than these will be apparent from the descriptions of the specification, the drawings, the claims, and the like and effects other than these can be derived from the descriptions of the specification, the drawings, the claims, and the like.

BRIEF DESCRIPTION OF DRAWINGS

FIGS. 2A and 2B are conceptual views of an active matrix light-emitting apparatus.
FIGS. 3A and 3B are conceptual views of active matrix light-emitting apparatuses.

FIGS. 7A-7C are drawings illustrating electronic devices.

MODE FOR CARRYING OUT THE INVENTION

Figure 1A:
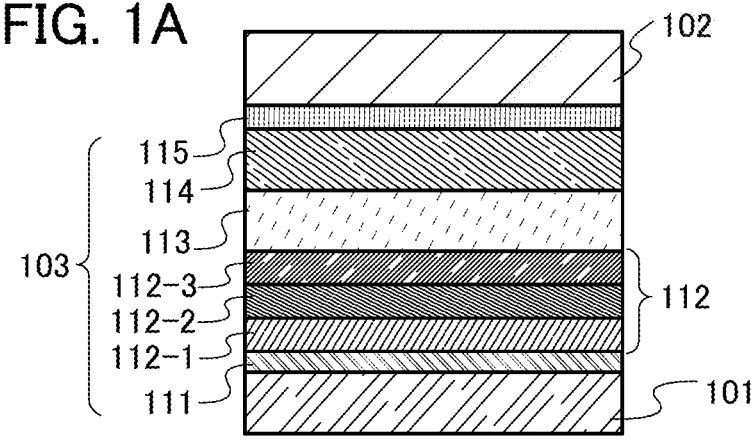
FIGS. 1A-1C are schematic views of light-emitting devices.

Embodiments of the present invention will be described in detail below with reference to the drawings. Note that the present invention is not limited to the following descriptions, and it will be readily appreciated by those skilled in the art that modes and details of the present invention can be modified in various ways without departing from the spirit and scope of the present invention. Thus, the present invention should not be interpreted as being limited to the descriptions in the following embodiments.

Embodiment 1

One embodiment of the present invention is a dibenzo[c,g]carbazole derivative represented by the following general formula (G1).

[Chemical Formula 6]

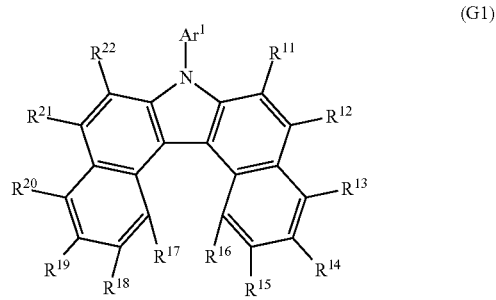

(G1)

Note that in the general formula (G1), at least one of $R^{11}$ to $R^{22}$ represents a substituent that has 14 to 60 carbon atoms in total and contains a condensed tricyclic to hexacyclic aromatic hydrocarbon skeleton, and the others independently represent any of hydrogen, an alkyl group having 1 to 6 carbon atoms, a cycloalkyl group having 3 to 6 carbon atoms, and a substituted or unsubstituted aryl group having 6 to 25 carbon atoms.

Note that in the case where a thin film of a material for the light-emitting device is formed particularly by an evaporation method, too high molecular weight causes problems such as decomposition at the time of evaporation; thus, the substituent that has 14 to 60 carbon atoms in total and contains a condensed tricyclic to hexacyclic aromatic hydrocarbon skeleton is preferably any one of $R^{11}$ to $R^{22}$. For the same reason, the substituent containing a condensed tricyclic to hexacyclic aromatic hydrocarbon skeleton preferably has 14 to 60 carbon atoms.

In addition, the dibenzo[c,g]carbazole derivative that includes a substituent containing a condensed aromatic hydrocarbon at the 5-position of the dibenzo[c,g]carbazole skeleton, i.e., the position of $R^{12}$ in the above general formula (G1) has an excellent hole-transport property; thus, in one embodiment of the present invention, $R^{12}$ is preferably a substituent that has 14 to 60 carbon atoms in total and contains a condensed tricyclic to hexacyclic aromatic hydrocarbon skeleton.

Note that examples of the condensed tricyclic to hexacyclic aromatic hydrocarbon skeleton include an anthracene skeleton, a phenanthrene skeleton, a triphenylene skeleton, a fluorene skeleton, a fluoranthene skeleton, a pyrene skeleton, a chrysene skeleton, a spirobifluorene skeleton, a benzo[a]anthracene skeleton, and a benzo[b]triphenylene skeleton. In the above, any of the anthracene skeleton, the phenanthrene skeleton, and the triphenylene skeleton is particularly preferable for easy synthesis. In addition, these skeletons may each include a substituent, and in that case, examples of the substituent include an alkyl group having 1 to 6 carbon atoms, a cycloalkyl group having 3 to 6 carbon atoms, and an aryl group having 6 to 25 carbon atoms.

Note that $R^{11}$ to $R^{22}$ other than substituents that has 14 to 60 carbon atoms in total and contains a condensed tricyclic to hexacyclic aromatic hydrocarbon independently represent hydrogen, an alkyl group having 3 to 6 carbon atoms, a cycloalkyl group having 3 to 6 carbon atoms, or a substituted or unsubstituted aryl group having 6 to 25 carbon atoms; however, the structure in which $R^{11}$ to $R^{22}$ are each hydrogen is preferable in terms of easy synthesis and availability of a material.

Furthermore, $Ar^1$ represents a substituted or unsubstituted aryl group having 6 to 13 carbon atoms in a ring. $Ar^1$ is preferably 6 to 13 substituted or unsubstituted aryl groups for easy synthesis. Examples of the aryl group having 6 to 13 carbon atoms in a ring include a phenyl group, a naphthyl group, a biphenyl group, and a 9H-fluorenyl group. Furthermore, these aryl groups may include a substituent; examples of the substituent include an alkyl group having 1 to 6 carbon atoms, a cycloalkyl group having 3 to 6 carbon atoms, an alkoxy group having 1 to 6 carbon atoms, and a phenyl group, and examples of the aryl group including any of these substituents include a 9,9-dimethylfluorenyl group, a 9,9-diphenylfluorenyl group, a 9,9'-spirobifluorenyl group, a tolyl group, and a mesityl group. An organic compound in which $Ar^1$ is a phenyl group is particularly preferable because of its high sublimability.

In another embodiment of the present invention, the condensed aromatic hydrocarbon skeleton of the substituent that has 14 to 60 carbon atoms in total and contains the condensed aromatic hydrocarbon skeleton is preferably combined with the dibenzo[c,g]carbazole skeleton through the arylene group in terms of easy synthesis and a high level of amorphousness. Accordingly, one embodiment of the present invention is a dibenzo[c,g]carbazole derivative represented by the following general formula (G2).

[Chemical Formula 7]

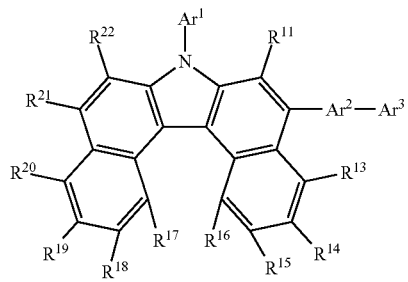

(G2)

Note that in the general formula (G2), $Ar^2$ represents a substituted or unsubstituted arylene group having 6 to 25 carbon atoms in a ring, and $Ar^3$ represents a substituent containing a condensed bicyclic to hexacyclic aromatic hydrocarbon skeleton. Note that the total number of carbon atoms contained in $Ar^2$ and $Ar^3$ is greater than or equal to 14 and less than or equal to 60.

Examples of the substituted or unsubstituted arylene group having 6 to 25 carbon atoms in a ring, which is represented by $Ar^2$, include a phenylene group, a naphthalenediyl group, a biphenyldiyl group, an anthracenediyl group, phenanthrenediyl group, a triphenylenediyl group, a 9H-fluorendiyl group, a 9,9-dimethylfluorendiyl group, and a 9,9'-spirobifluorendiyl group. These arylene groups may each include a substituent, and examples of the substituent include an alkyl group having 1 to 6 carbon atoms, a cycloalkyl group having 3 to 6 carbon atoms, and an alkokyl group having 1 to 6 carbon atoms. Note that an unsubstituted phenylene group is particularly preferable as $Ar^2$.

Examples of the substituent containing a condensed bicyclic to hexacyclic aromatic hydrocarbon skeleton, which is represented as AP, include a substituted or unsubstituted naphthyl group, a substituted or unsubstituted anthryl group, a substituted or unsubstituted phenanthryl group, a substituted or unsubstituted triphenylenyl group, a substituted or unsubstituted fluorenyl group, a substituted or unsubstituted dimethylfluorenyl group, and a substituted or unsubstituted spirobifluorenyl group. In the case where these include a substituent, examples of the substituent include an alkyl group having 1 to 6 carbon atoms, a cycloalkyl group having 3 to 6 carbon atoms, an alkoxyl group having 1 to 6 carbon atoms, and an aryl group having 6 to 13 carbon atoms.

Note that as $Ar^3$, an anthryl group including a phenyl group, particularly a 10-phenyl-9-anthryl group, an unsubstituted 9-phenanthryl group, or an unsubstituted triphenylen-2-yl group is preferable for easy synthesis.

Note that in the general formula (G2), the total number of carbon atoms in $Ar^2$ and $Ar^3$ is preferably 14 to 60 in terms of sublimability.

Since $R^{11}$, $R^{13}$ to $R^{22}$, and $Ar^1$ are similar to those in the general formula (G1), the descriptions thereof are omitted.

The dibenzo[c,g]carbazole derivative of one embodiment of the present invention can also be represented by the following general formula (G3).

[Chemical Formula 8]

(G3)

Note that in the general formula (G3), Ar² represents a substituted or unsubstituted arylene group having 6 to 25 carbon atoms in a ring, and Ar³ represents any one of a substituted or unsubstituted anthryl group, a substituted or unsubstituted phenanthryl group, and a substituted or unsubstituted triphenylenyl group. Furthermore, n is an integer of 0 to 3, and the total number of carbon atoms contained in Ar² and Ar³ is 14 to 60.

Since Ar² is the same as Ar² in the above general formula (G2), the description thereof is omitted. Although n is an integer of 0 to 3, particularly preferably 1 in terms of easy synthesis and a high level of amorphousness. In addition, Ar¹ is further preferably a phenyl group in that case.

In the above general formula (G3), Ar³ is preferably a substituted or unsubstituted anthryl group, a substituted or unsubstituted phenanthryl group, or a substituted or unsubstituted triphenylenyl group for easy synthesis. In addition, in the case where the dibenzo[c,g]carbazole derivative is used as a fluorescent host, Ar³ that is a substituted or unsubstituted anthryl group can increase the electron-transport property, which is further preferable in terms of lower driving voltage and the like.

Note that in the case where the anthryl group, the phenanthryl group, or the triphenylenyl group includes a substituent, examples of the substituent include an alkyl group having 1 to 6 carbon atoms, a cycloalkyl group having 3 to 6 carbon atoms, an alkoxy group having 1 to 6 carbon atoms, and an aryl group having 6 to 13 carbon atoms.

Note that when a device is formed by evaporation, too low molecular weight makes control difficult, whereas too high molecular weight makes evaporation difficult; thus, the total number of carbon atoms contained in n Ar² and Ar³ in the general formula (G3) is preferably 14 to 60.

Note that Since $R^{11}$, $R^{13}$ to $R^{22}$, $Ar^1$, and $Ar^2$ are similar to those in the general formula (G1), the descriptions thereof are omitted.

Specific examples of the groups represented by $R^{11}$ to $R^{22}$ in the above general formulae (G1) to (G3) are shown below.

[Chemical Formula 9]

(R-15) 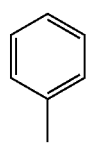
(R-16) 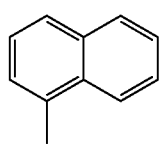
(R-17) 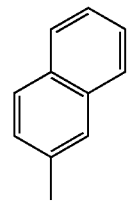
(R-18) 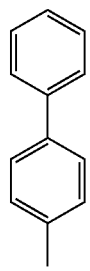
(R-19) 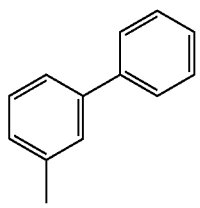
(R-20) 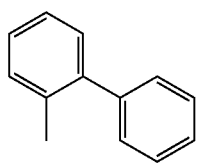
(R-21) 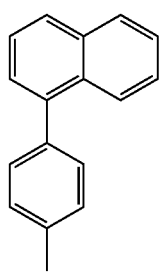
(R-22) 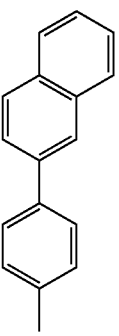
(R-23) 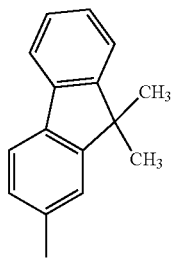
(R-24) 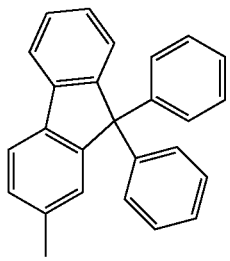
(R-25) 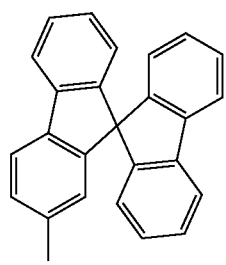
(R-26) 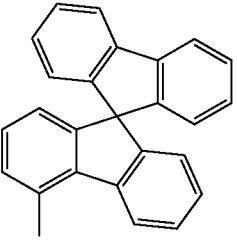
(R-27) 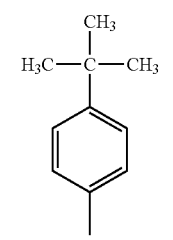

(R-28)
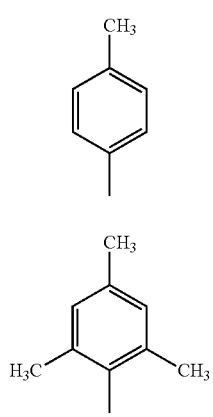
(R-29)
Specific examples of the groups represented by Ar¹ in the above general formulae (G1) to (G3) are shown below.
[Chemical Formula 10]
(Ar¹-1)
(Ar¹-2)
(Ar¹-3)
(Ar¹-4)
(Ar¹-5)
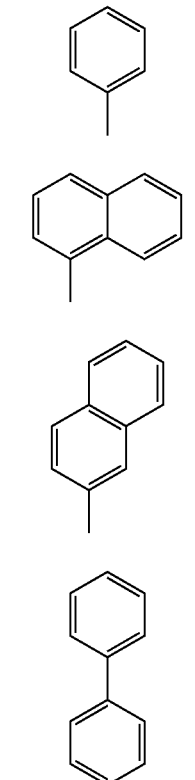
(Ar¹-6)
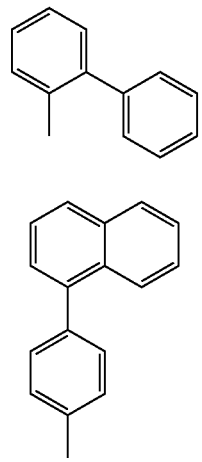
(Ar¹-7)
(Ar¹-8)
(Ar¹-9)
(Ar¹-10)
(Ar¹-11)
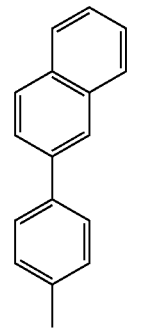
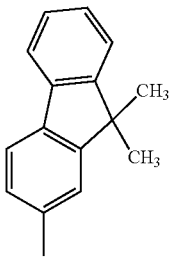
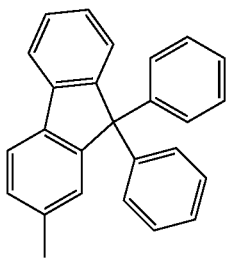
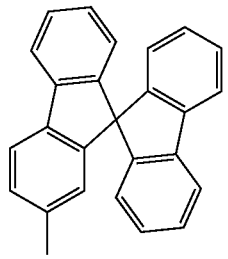

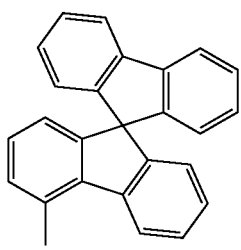 (Ar¹-12)
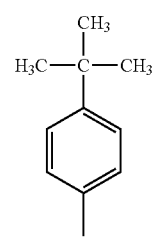 (Ar¹-13)
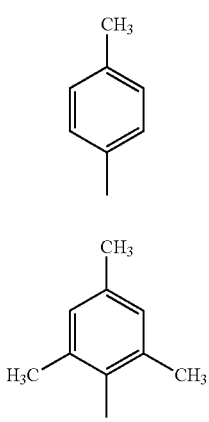 (Ar¹-14)
(Ar¹-15)
Specific examples of the groups represented by Ar² in the above general formulae (G2) and (G3) are shown below.
[Chemical Formula 11]
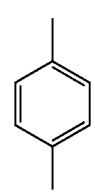 (Ar²-1)
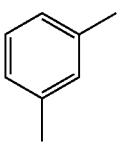 (Ar²-2)
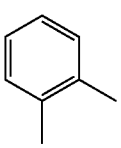 (Ar²-3)
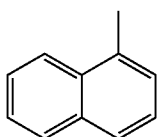 (Ar²-4)
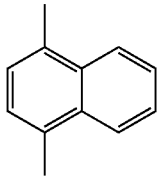 (Ar²-5)
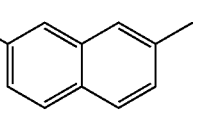 (Ar²-6)
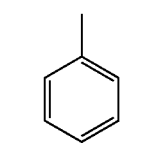 (Ar²-7)
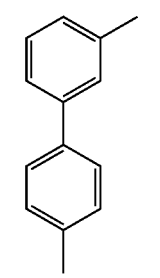 (Ar²-8)
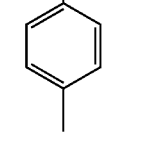 (Ar²-9)
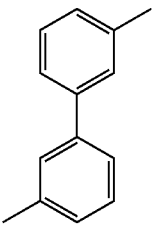 (Ar²-10)

(Ar²-11)
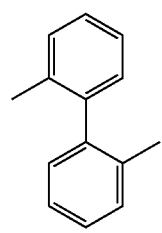
(Ar²-12)
(Ar²-13)
(Ar²-14)
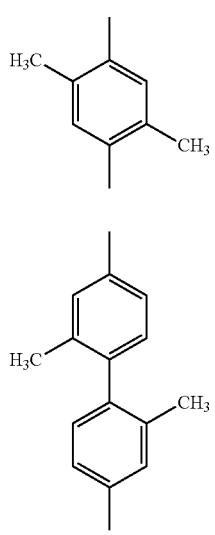
(Ar²-15)
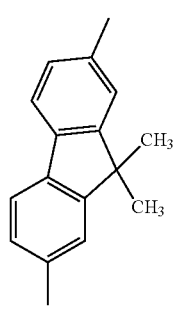
(Ar²-16)
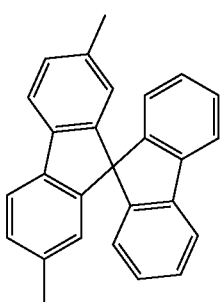
(Ar²-17)
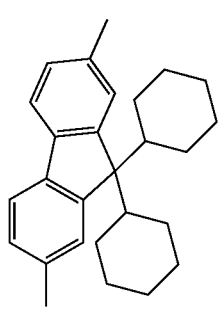
(Ar²-18)
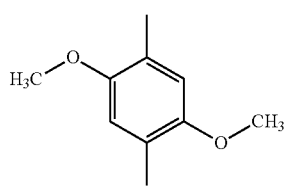
Specific examples of the groups represented by Ar³ in the above general formulae (G2) and (G3) are shown below.
[Chemical Formula 12]
(Ar³-1)
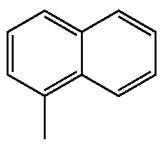
(Ar³-2)
(Ar³-3)
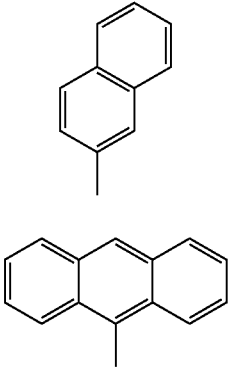

-continued
(Ar³-4)
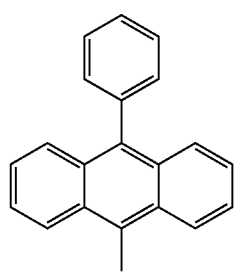
(Ar³-5)
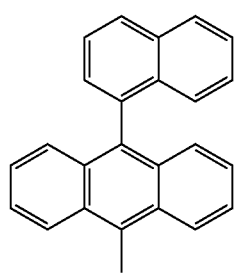
(Ar³-6)
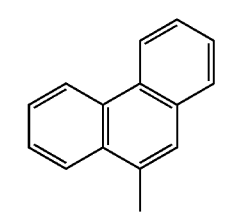
(Ar³-7)
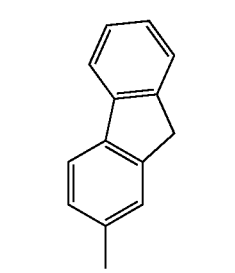
(Ar³-8)
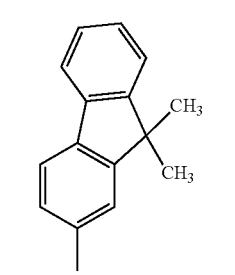
(Ar³-9)
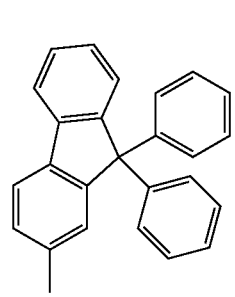
-continued
(Ar³-10)
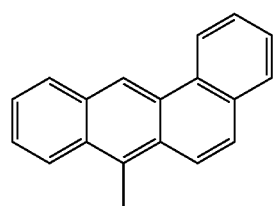
(Ar³-11)
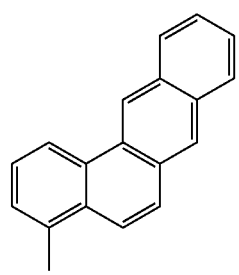
(Ar³-12)
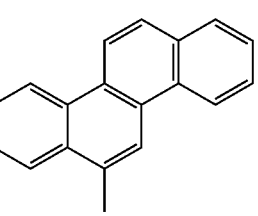
(Ar³-13)
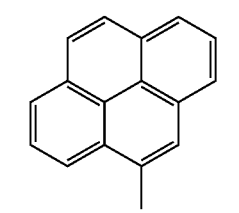
(Ar³-14)
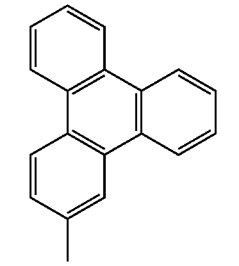
(Ar³-15)
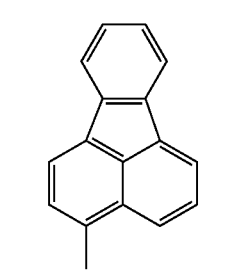

(Ar³-16)
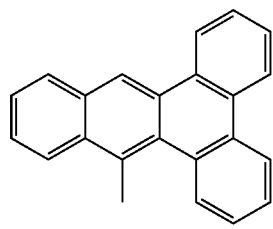
(Ar³-17)
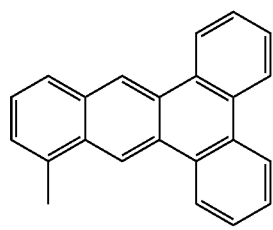
(Ar³-18)
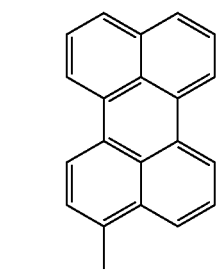
(Ar³-19)
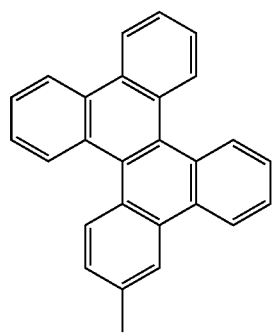
(Ar³-20)
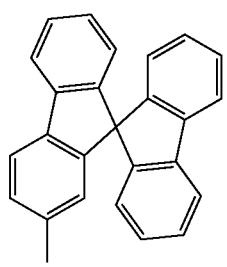
(Ar³-21)
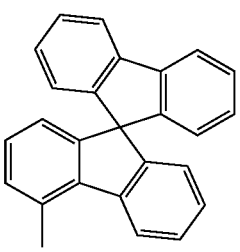
(Ar³-22)
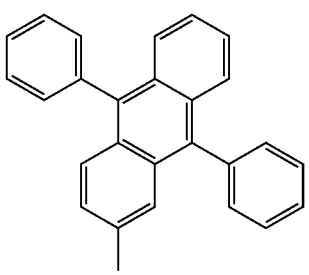
Specific examples of the dibenzo[c,g]carbazole derivative represented by the above general formulae (G1) to (G3) are shown below.
[Chemical Formula 13]
(100)
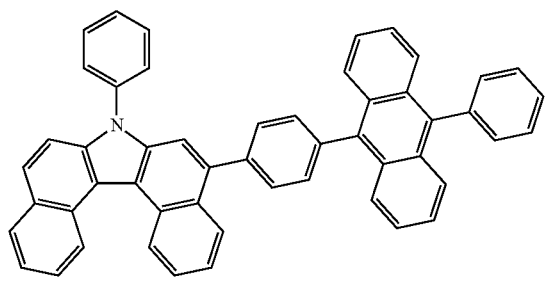
(101)
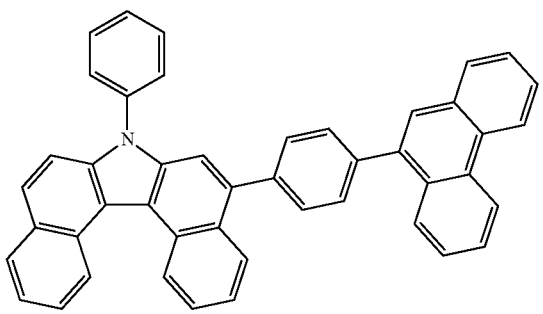

-continued
(102)
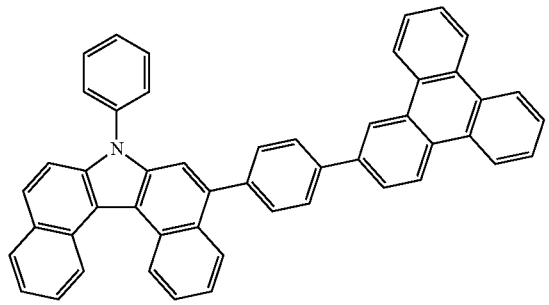
(103)
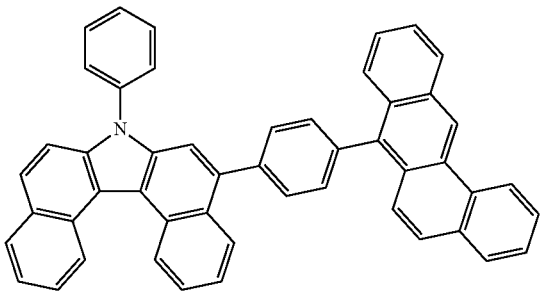
(104)
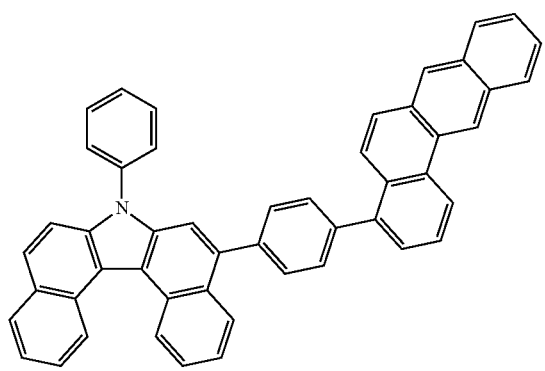
(105)
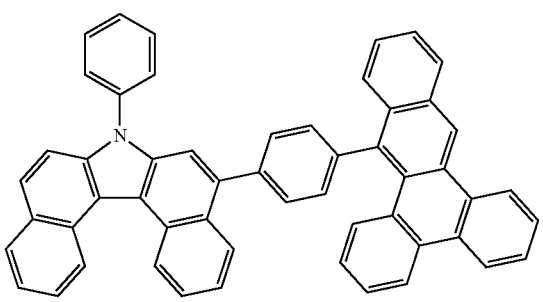
(106)
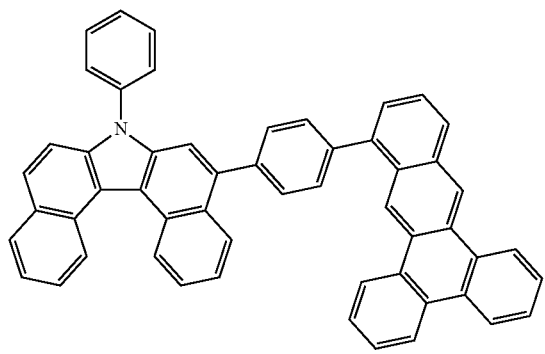
(107)
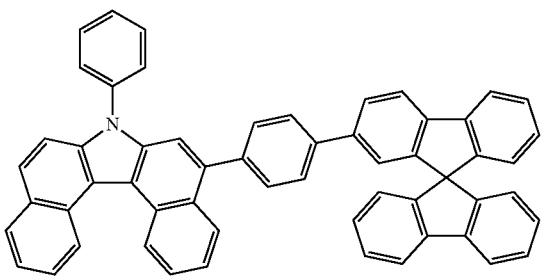
[Chemical Formula 14]
(108)
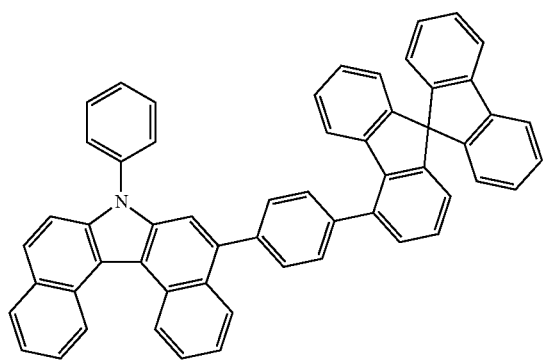
(109)
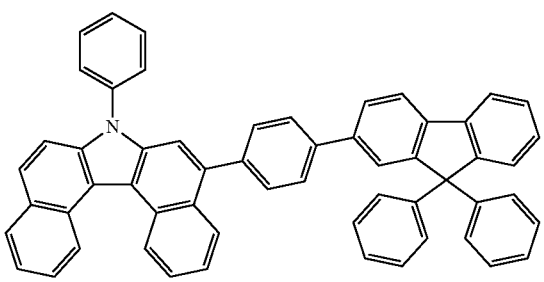

-continued
(110)
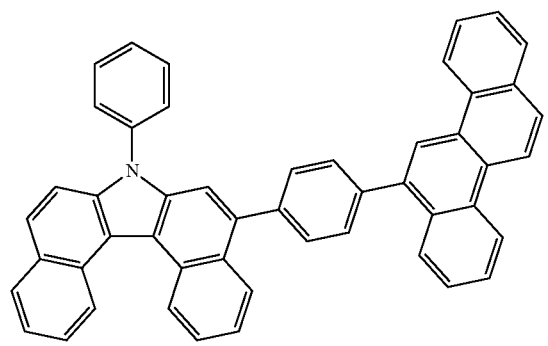
(111)
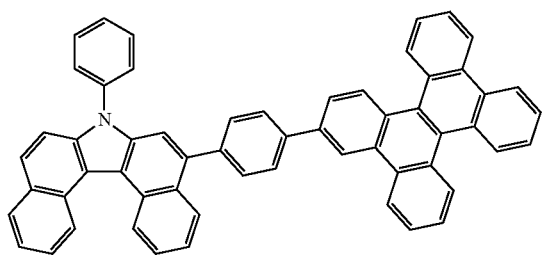
(112)
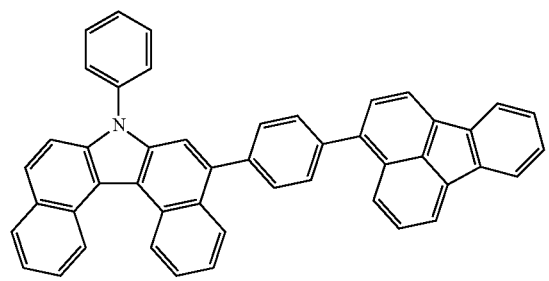
(113)
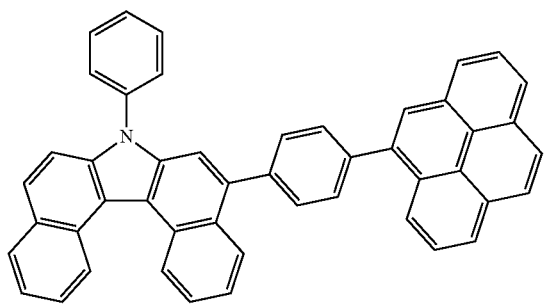
(114)
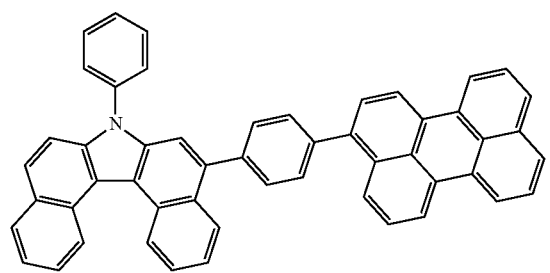
(115)
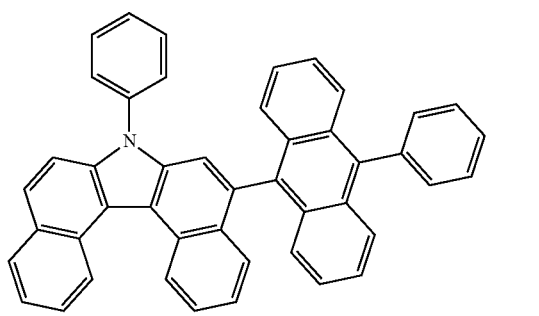
[Chemical Formula 15]
(116)
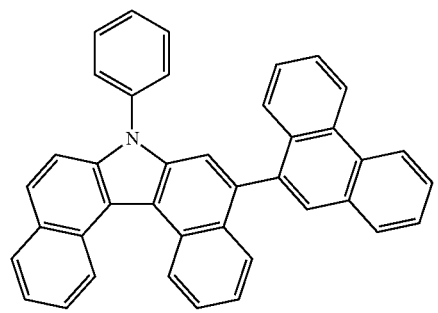
(117)
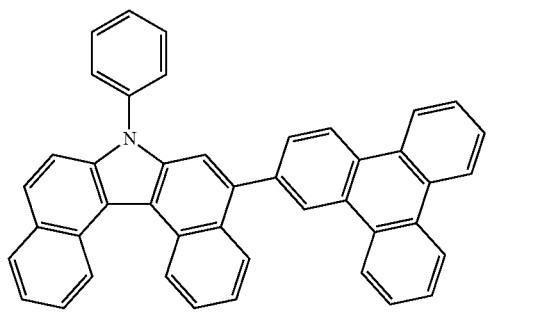

-continued
(118)
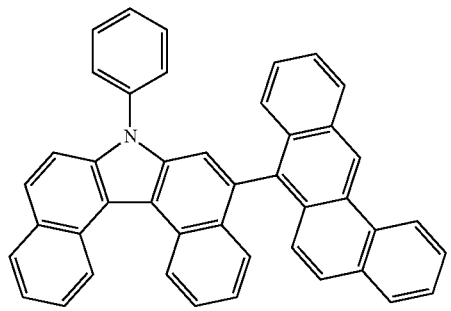
(119)
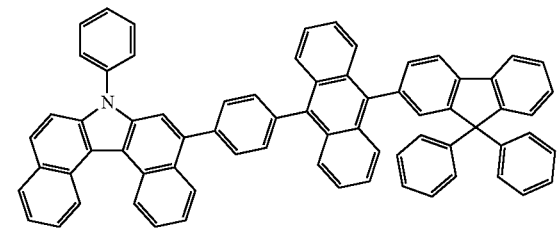
(120)
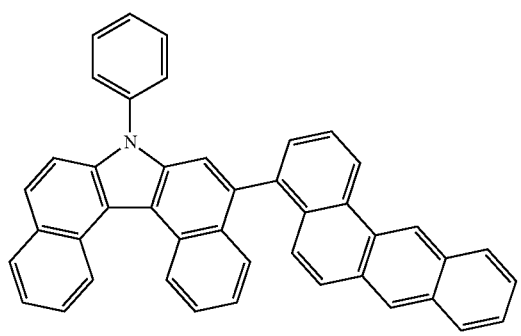
(121)
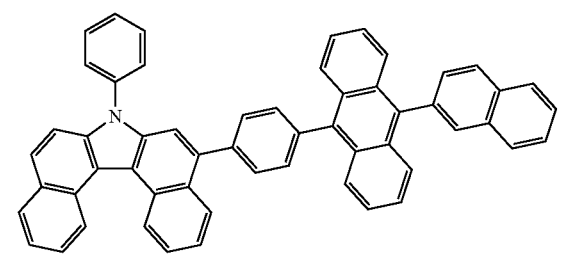
(122)
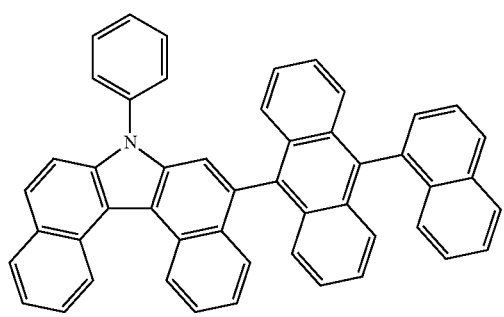
(123)
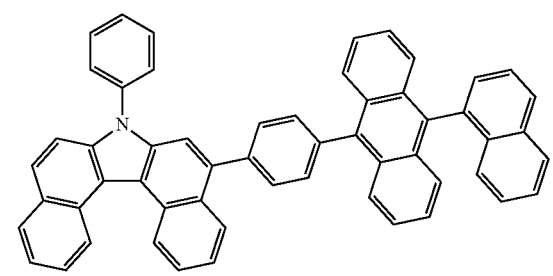
[Chemical Formula 16]
(124)
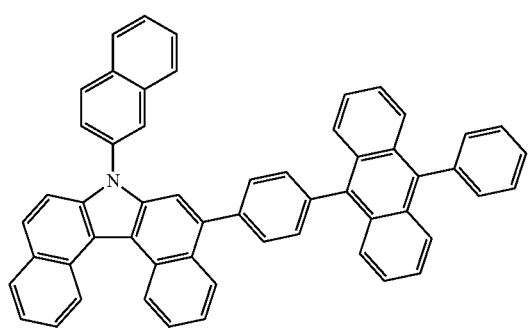
(125)
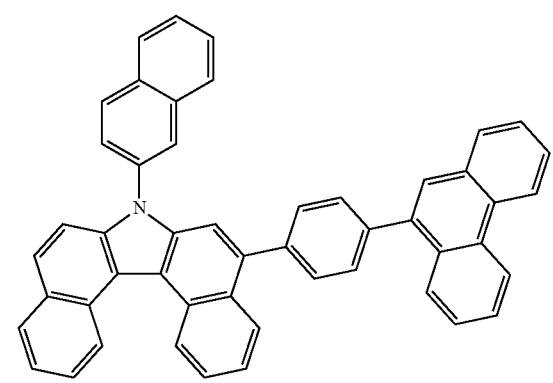

-continued
(126)
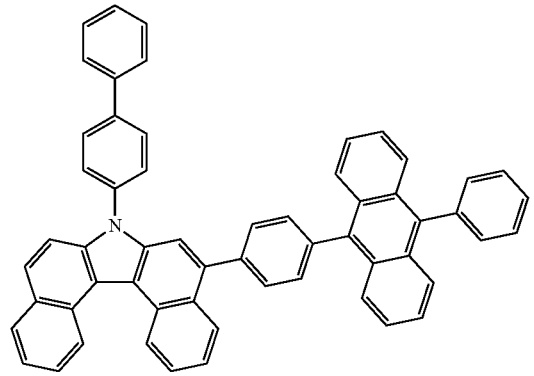
(127)
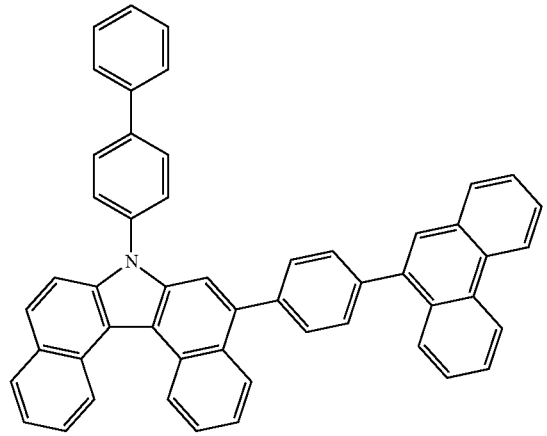
(128)
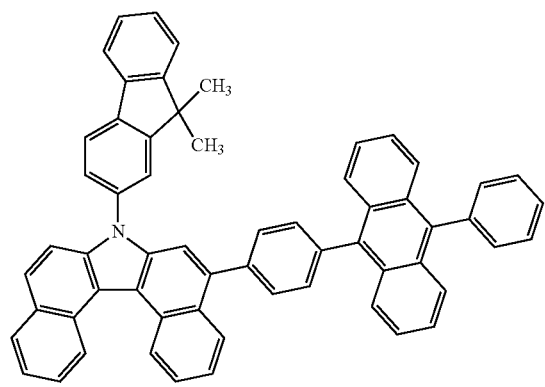
(129)
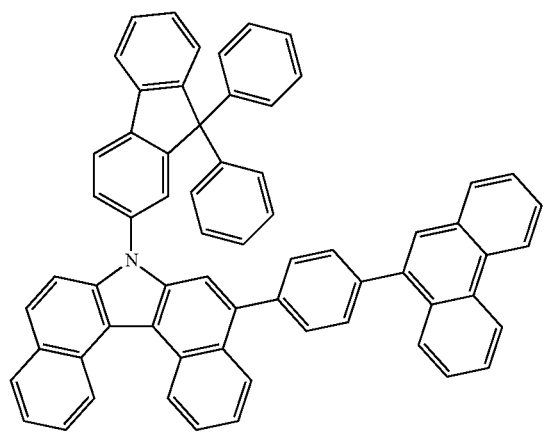
(130)
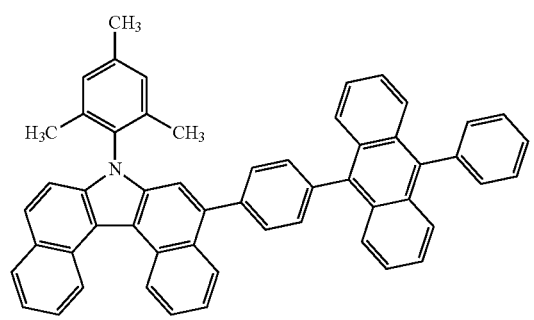
(131)
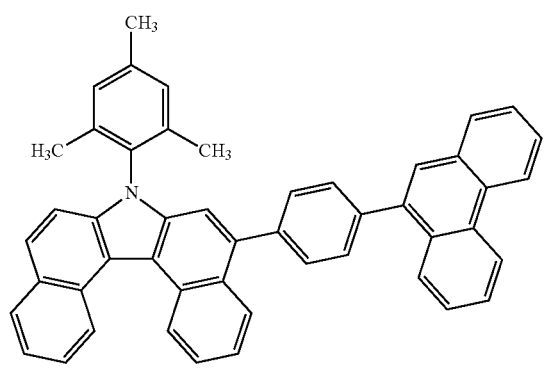

[Chemical Formula 17]
(132)
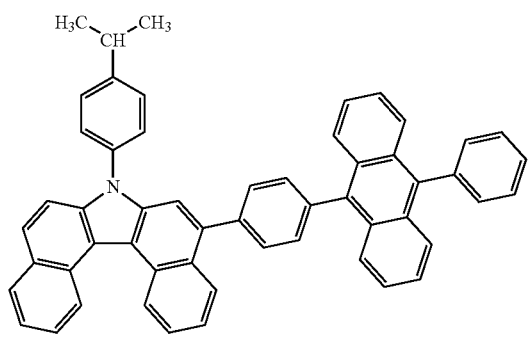
(133)
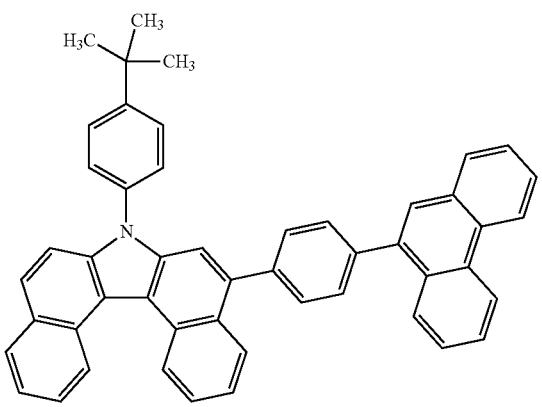
(134)
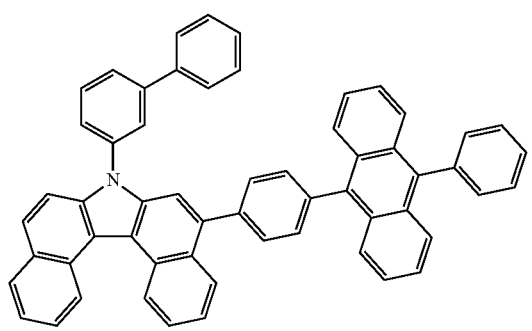
(135)
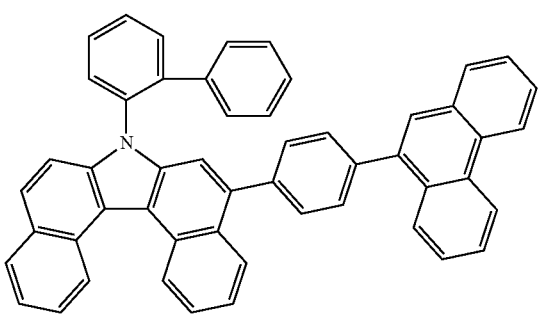
(136)
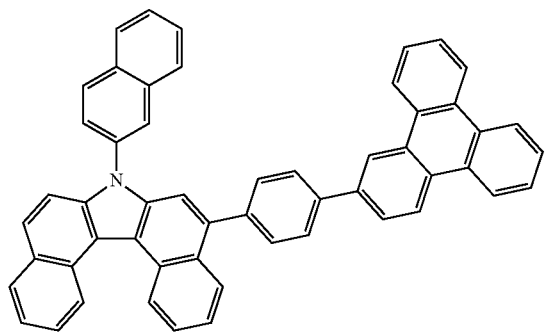
(137)
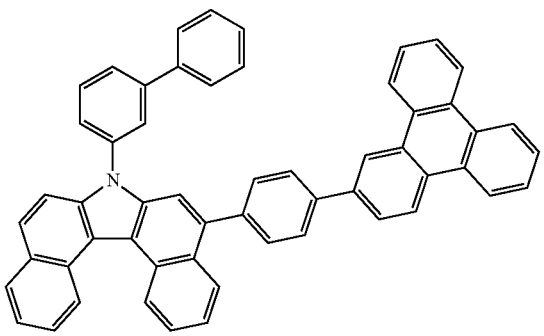
(138)
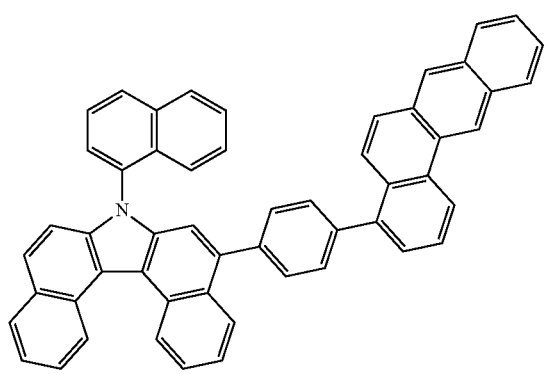
(139)
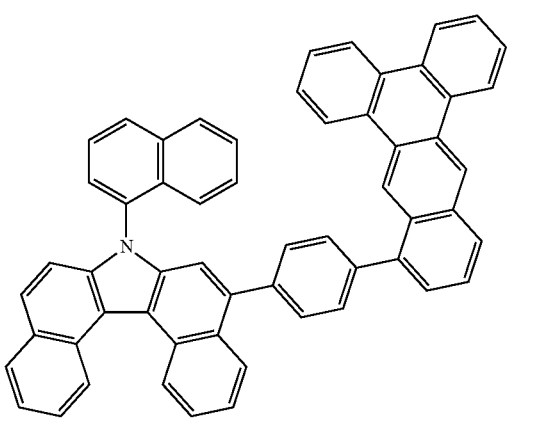

[Chemical Formula 18]
(140)
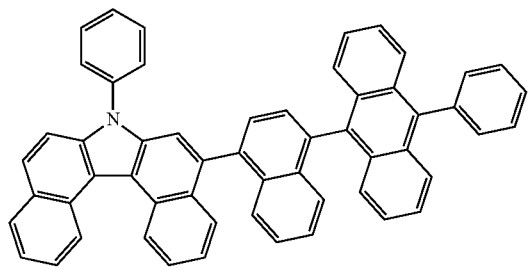
(141)
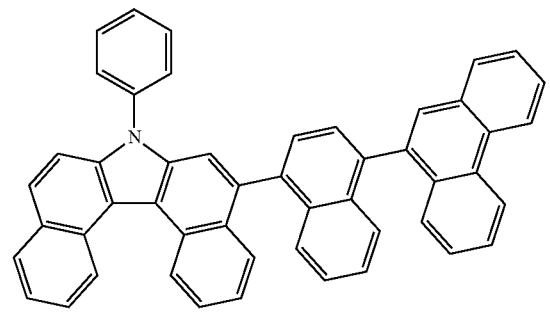
(142)
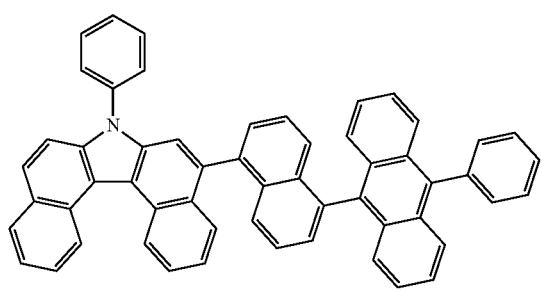
(143)
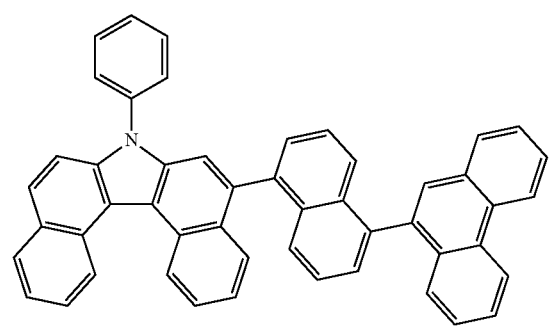
(144)
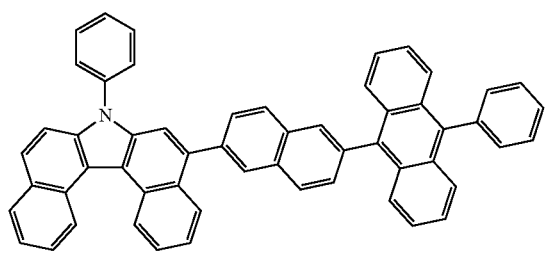
(145)
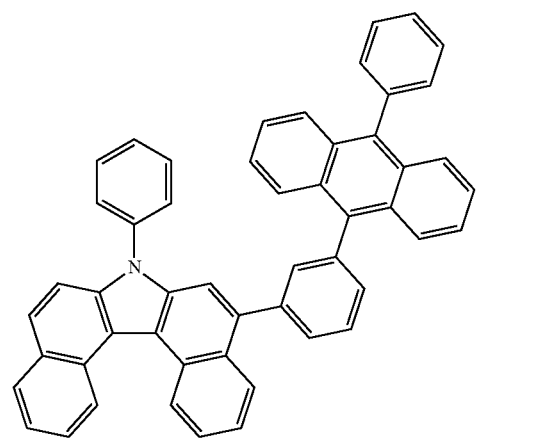
(146)
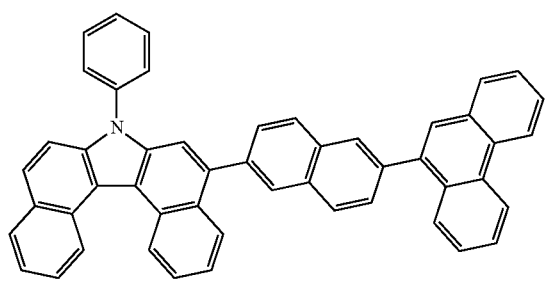
(147)
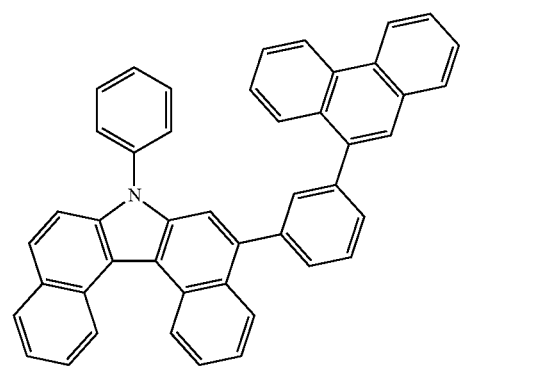

[Chemical Formula 19]
(148)
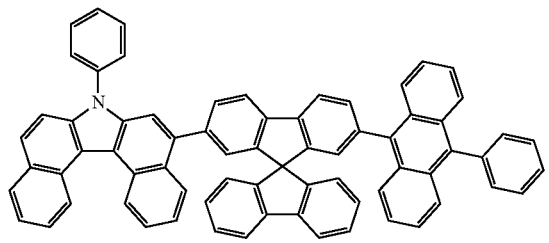
(149)
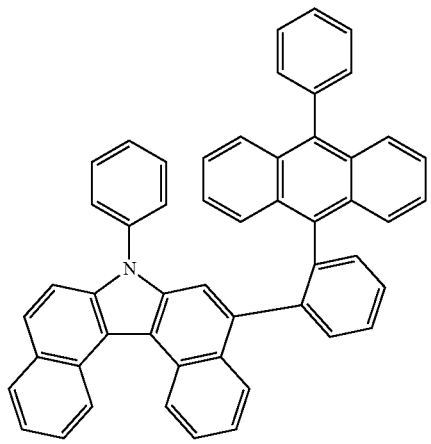
(150)
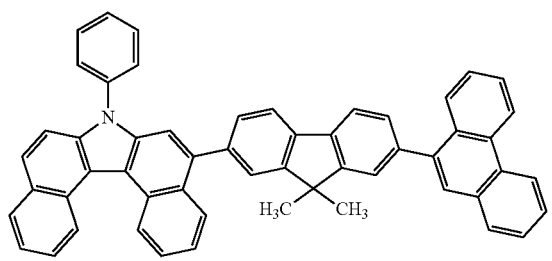
(151)
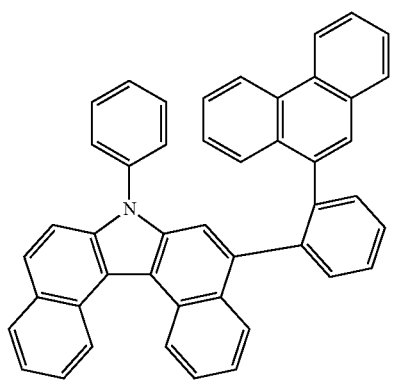
(152)
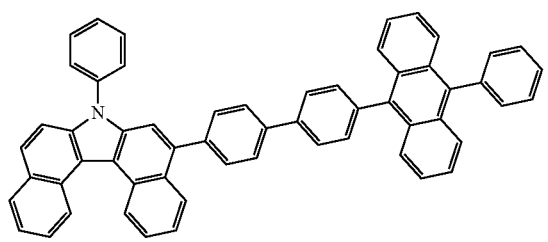
(153)
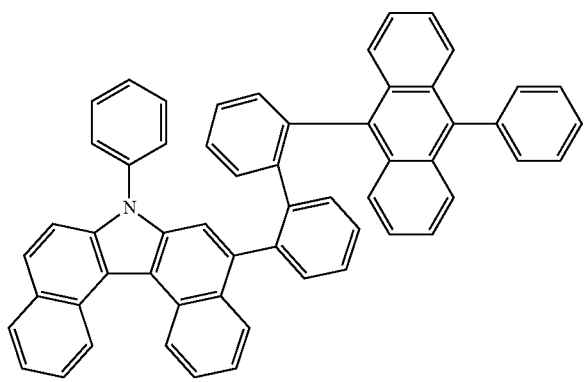

-continued
(154)
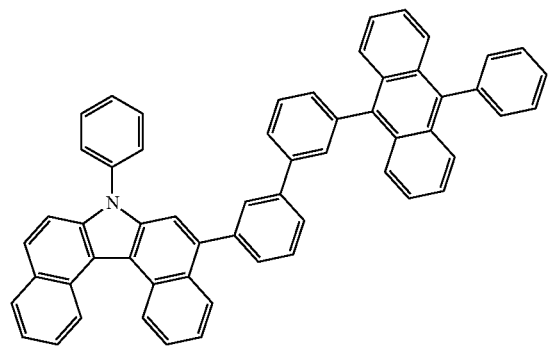
(156)
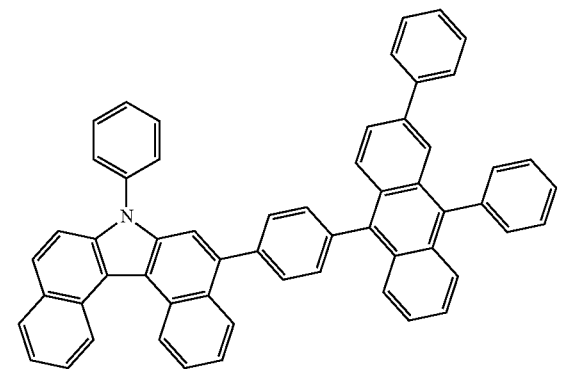
[Chemical Formula 20]
(157)
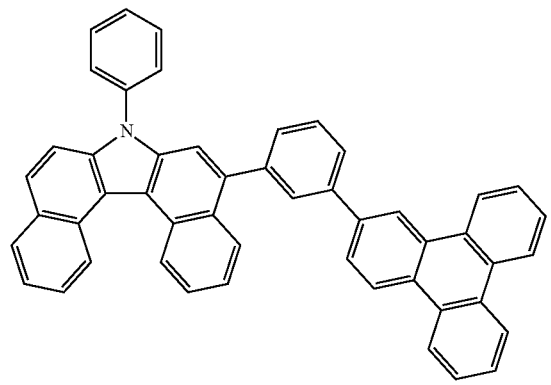
(158)
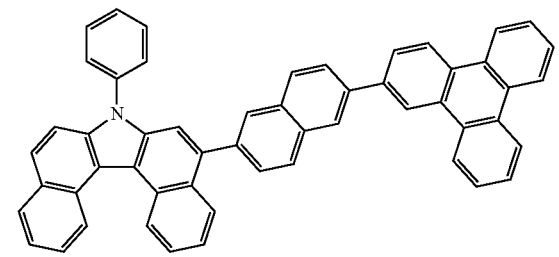
(159)
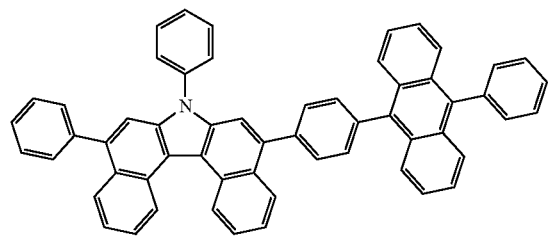
(160)
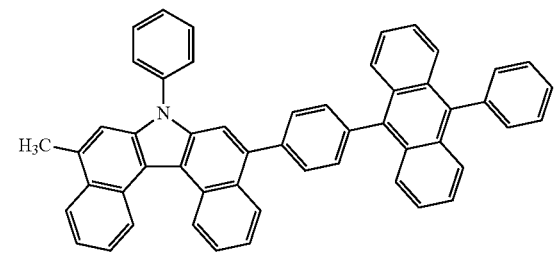
(161)
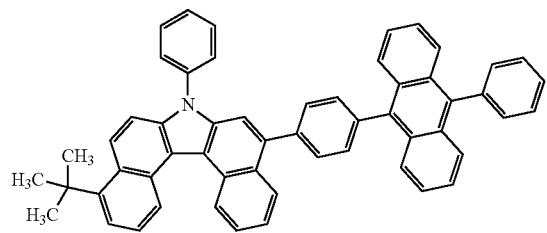
(162)
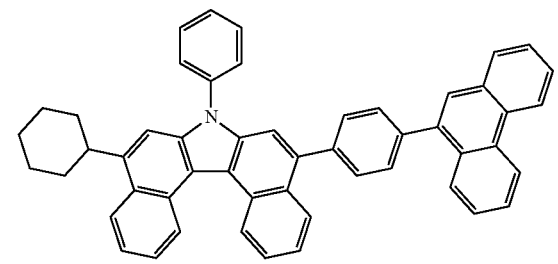

(163)
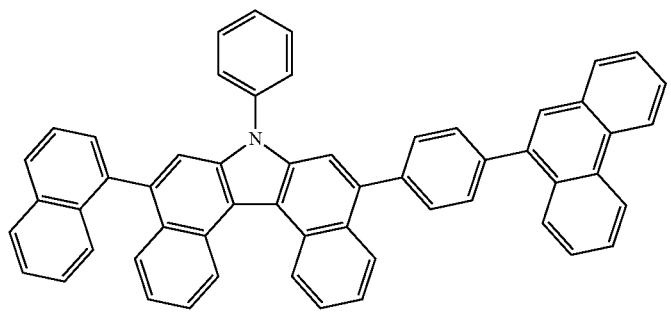
[Chemical Formula 21]
(164)
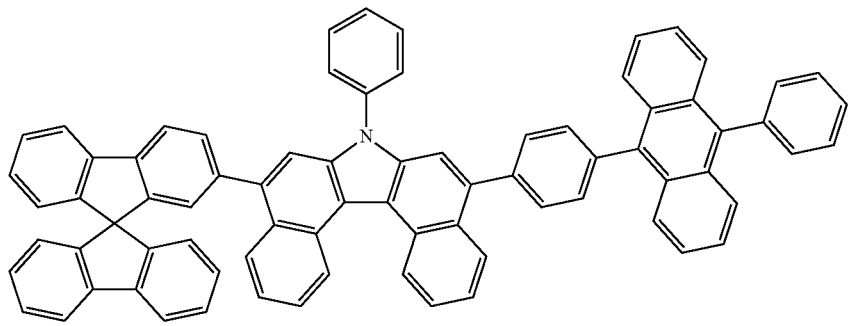
(165)
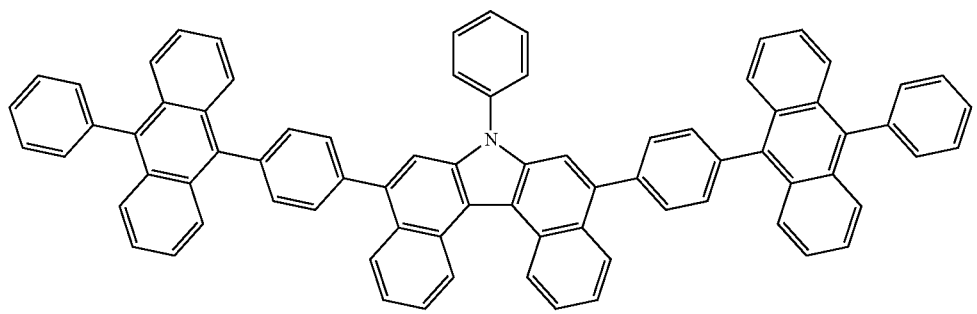
(166)
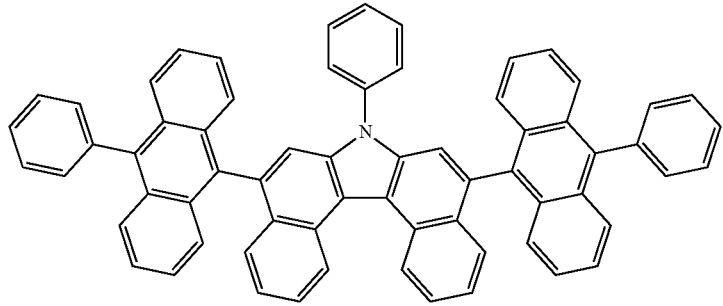
(167)
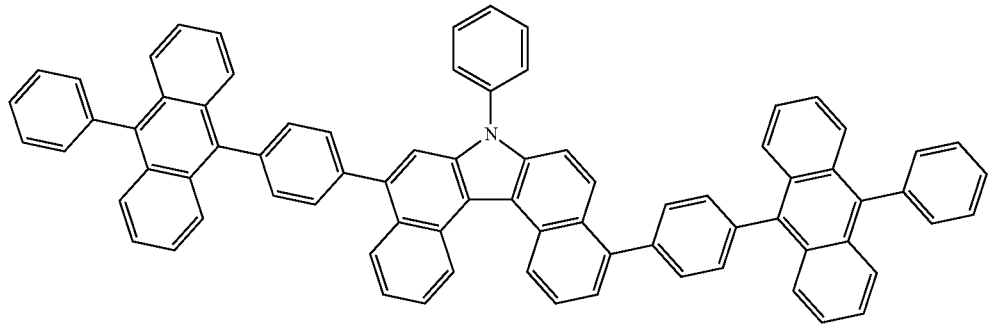

(168)
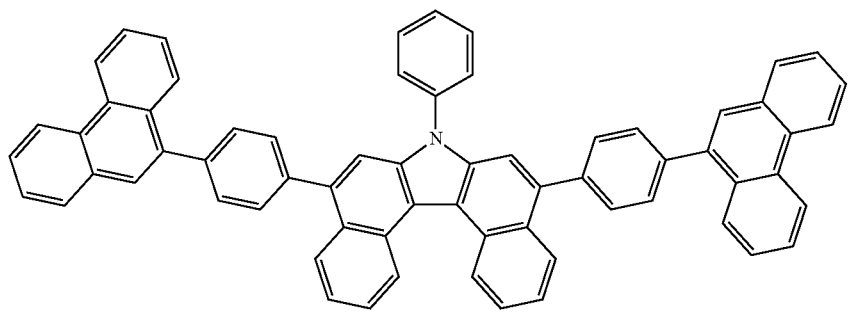
[Chemical Formula 22]
(169)
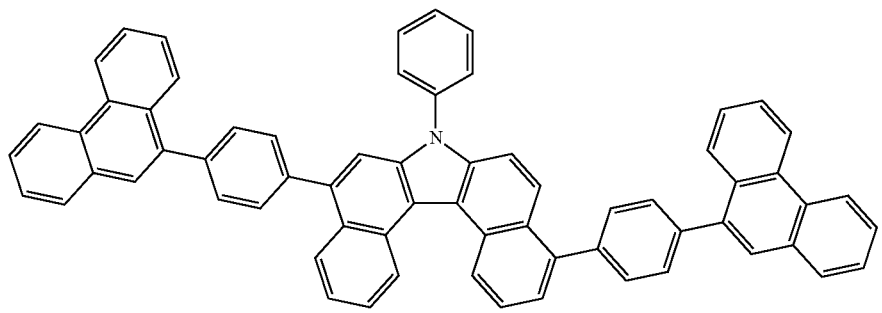
(170)
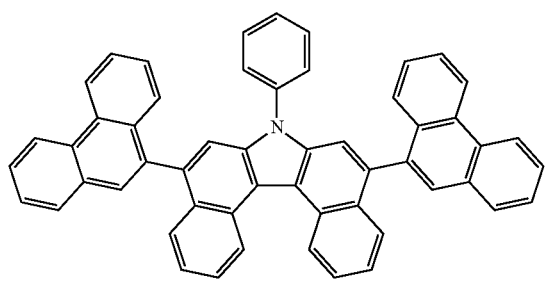
(171)
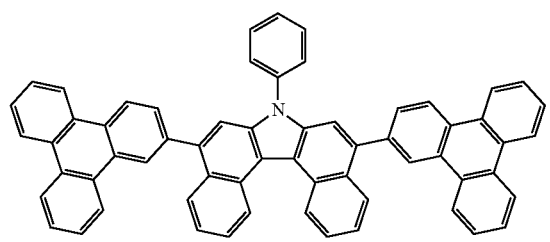
(172)
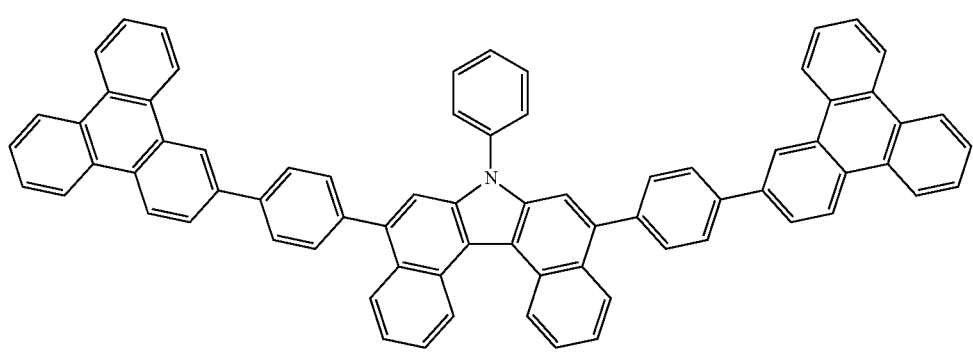

(173)
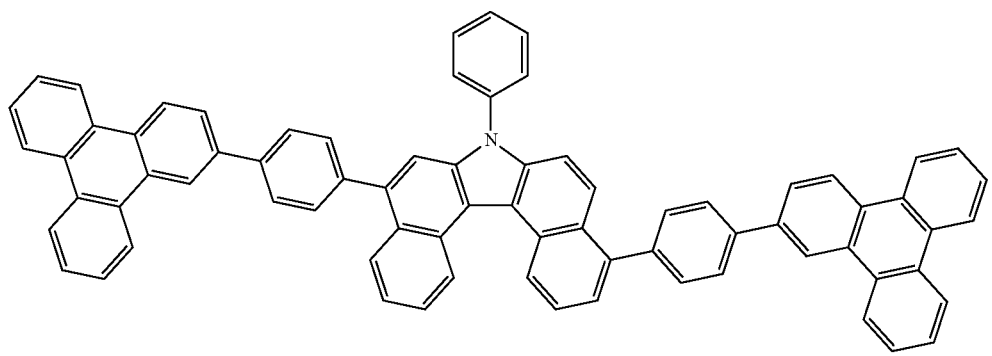
[Chemical Formula 23]
(174)
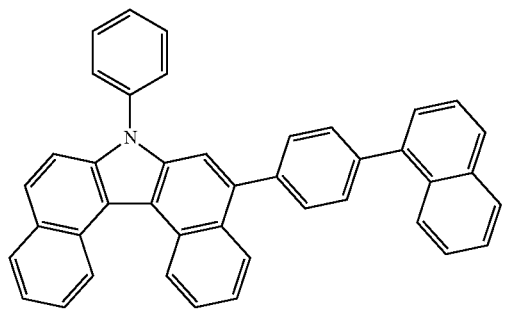
(175)
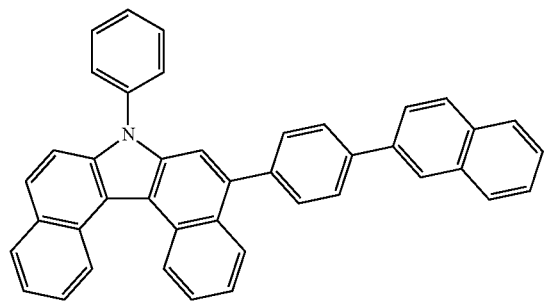
(176)
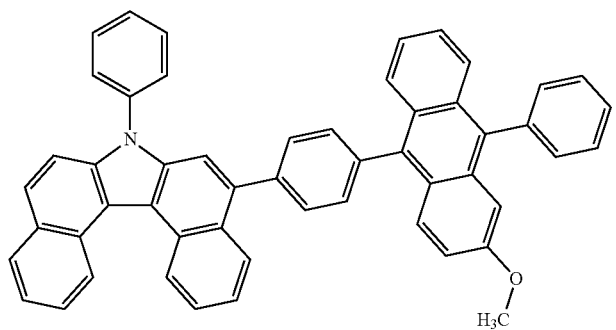
(177)
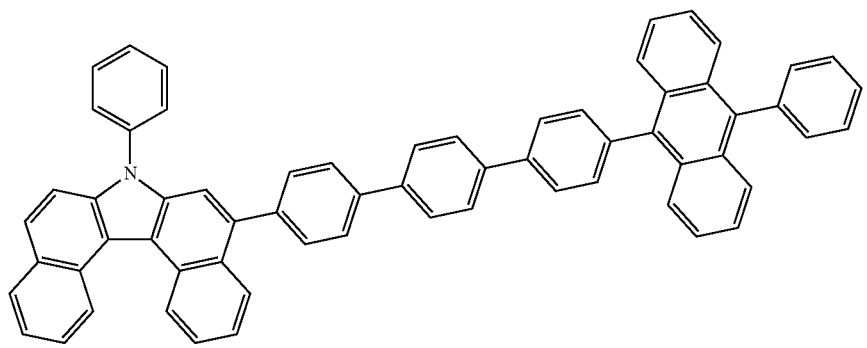

-continued (178)

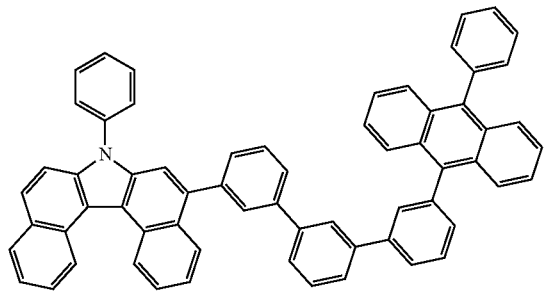

(179)

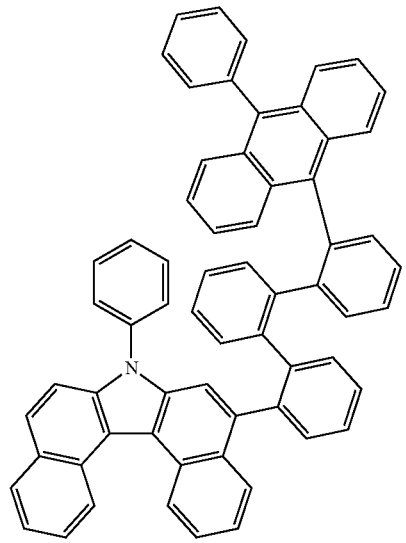

When the above-described organic compounds having an excellent hole-transport property are used as a host material or a material for a hole-transport layer, a light-emitting device with a low driving voltage can be fabricated. In addition, a light-emitting device with favorable emission efficiency can be fabricated.

The above-described organic compounds can be synthesized by the following synthesis scheme, for example. Note that a synthesis method of the dibenzo[c,g]carbazole derivative represented by the above general formula (G2) is described as an example here.

As shown in the following synthesis scheme (A-1), the dibenzo[c,g]carbazole derivative represented by the above general formula (G2) can be obtained by coupling a halide of the dibenzo[c,g]carbazole derivative (Compound 1) and an organoboron compound or boronic acid of a condensed aromatic hydrocarbon skeleton (Compound 2) by a Suzuki-Miyaura reaction.

[Chemical Formula 24]

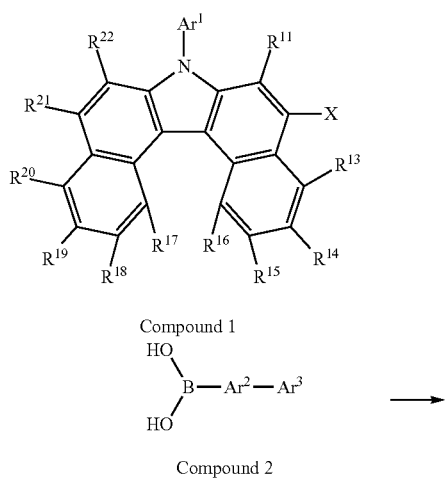

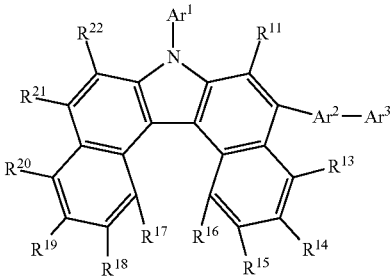

Target compound 1

In the above synthesis scheme (A-1), X represents a halogen or a triflate group. Furthermore, since $Ar^1$, $Ar^2$, $Ar^3$, $R^{11}$, and $R^{13}$ to $R^{22}$ in the above synthesis scheme (A-1) are the same as those in the description of the above general formula (G2), the descriptions thereof are omitted.

In the case of performing the synthesis scheme (A-1) by the Suzuki-Miyaura reaction, a palladium catalyst is used; examples of the palladium catalyst that can be used include palladium(II) acetate, tetrakis(triphenylphosphine)palladium(0), and bis(triphenylphosphine)palladium(II) dichloride. Note that examples of the ligands of the palladium catalyst that can be used in the synthesis scheme (A-1) include tri(ortho-tolyl)phosphine, triphenylphosphine, and tricyclohexylphosphine.

In addition, a base is used in the reaction; examples of the base that can be used include organic bases such as sodium tert-butoxide, and inorganic bases such as potassium carbonate and sodium carbonate. Furthermore, in the case where a solvent is used in the synthesis scheme (A-1), examples of the solvent that can be used include a mixed solvent of toluene and water; a mixed solvent of toluene, alcohol such as ethanol, and water; a mixed solvent of xylene and water; a mixed solvent of xylene, alcohol such as ethanol, and water; a mixed solvent of benzene and water; a mixed solvent of benzene, alcohol such as ethanol, and water; and a mixed solvent of water and an ether such as ethylene glycol dimethyl ether. Note that a mixed solvent of toluene and water, a mixed solvent of toluene, ethanol, and water, or a mixed solvent of water and an ether such as ethylene glycol dimethyl ether is further preferable.

In addition, in the reaction, the organoboron compound or boronic acid represented by Compound 2 may be a compound of organoaluminum, organozirconium, organozinc, organotin, or the like.

In the synthesis scheme (A-1), the organoboron compound or boron acid of a condensed aromatic hydrocarbon skeleton is reacted with the halide of the dibenzo[c,g]carbazole derivative or the dibenzo[c,g]carbazole derivative having a triflate group as a substituent; however, the organoboron compound or boron acid of the dibenzo[c,g]carbazole derivative may be coupled to the halide of a condensed aromatic hydrocarbon skeleton or a condensed aromatic hydrocarbon skeleton having a triflate group as a substituent.

Note that the above synthesis scheme describes a synthesis method of the dibenzo[c,g]carbazole derivative represented by the general formula (G2) as an example; however, in the case of synthesizing the dibenzo[c,g]carbazole derivative represented by the general formula (G1), a compound in which a substituent X is at the position where a substituent that has 14 to 60 carbon atoms in total and contains a condensed tricyclic to hexacyclic aromatic hydrocarbon skeleton is combined can be used instead of Compound 1.

Embodiment 2

FIG. 1 illustrates a drawing of light-emitting devices of one embodiment of the present invention. The light-emitting device of one embodiment of the present invention includes a first electrode 101, a second electrode 102, and an EL layer 103, and a hole-transport material including the above-described organic compound is used for the EL layer.

The EL layer 103 includes a light-emitting layer 113 and may also include a hole-transport layer 112. The light-emitting layer 113 includes a light-emitting material and a host material, and light emission is obtained from the light-emitting material in the light-emitting device of one embodiment of the present invention. The dibenzo[c,g]carbazole derivative material of one embodiment of the present invention may be included in any part of the EL layer 103, but is preferably used as a material for the light-emitting layer 113 or the hole-transport layer 112.

Note that FIG. 1 additionally illustrates a hole-injection layer 111, an electron-transport layer 114, and an electron-injection layer 115; however, the structure of the light-emitting device is not limited thereto.

The dibenzo[c,g]carbazole derivative of one embodiment of the present invention can be used as a host material in which light-emitting substances are dispersed in the light-emitting layer. Furthermore, in that case, a structure may be employed in which co-evaporation with an electron-transport material is performed to form an exciplex of the electron-transport material and the dibenzo[c,g]carbazole derivative of one embodiment of the present invention. Formation of the exciplex having an appropriate emission wavelength achieves efficient energy transfer to the light-emitting material and enables a light-emitting device with high efficiency and a favorable lifetime to be provided.

In addition, the dibenzo[c,g]carbazole derivative of one embodiment of the present invention has a favorable hole-transport property and thus is effectively used for the hole-transport layer 112.

Here, in the case where the hole injection is performed using an organic compound having an acceptor property, a compound included in the hole-transport layer 112 that is in contact with the hole-injection layer 111 is preferably a hole-transport material with a relatively shallow HOMO level in order to facilitate the electron extraction by the organic compound having an acceptor property. However, it is difficult to inject holes into the light-emitting layer 113 from the hole-transport material with a relatively shallow HOMO level; thus, when the light-emitting layer 113 is formed in contact with the hole-transport layer 112 made of such a hole-transport material with a relatively shallow HOMO level, carriers are accumulated at the interface therebetween, which might cause a decrease in the lifetime and efficiency of the light-emitting device. In particular, the influence tends to be large in a blue fluorescent device with a deep HOMO level.

In view of this, a layer of the hole-transport material having a HOMO level between the relatively shallow HOMO level and the HOMO level of the light-emitting layer is provided between the light-emitting layer and the hole-transport material having the shallow HOMO level that is formed in contact with the hole-transport layer, which enables smooth hole injection into the light-emitting layer and achieves improvement in the lifetime and efficiency of the light-emitting device.

That is, a structure is preferable in which the hole-transport layer 112 includes a first hole-transport layer 112-1 and a second hole-transport layer 112-2 from the hole-injection layer 111 side, and the first hole-transport layer contains a first hole-transport material whereas the second hole-transport layer contains an organic compound whose HOMO level is deeper than the HOMO level of the first hole-transport material, which enables a light-emitting device with a favorable lifetime and efficiency. Note that the HOMO level of the first hole-transport material is preferably greater than or equal to −5.4 eV, in which case electrons can be easily extracted from the organic compound having an acceptor property. Note that the difference between the HOMO level of the first hole-transport material and the HOMO level of the organic compound described in Embodiment 1 is preferably less than or equal to 0.3 eV, further preferably less than or equal to 0.2 eV, in which case holes can be easily injected from the first hole-transport layer 112-1 into the second hole-transport layer 112-2.

In addition, the hole-transport layer 112 may further include a third hole-transport layer 112-3 between the second hole-transport layer 112-2 and the light-emitting layer, and the third hole-transport layer 112-3 may contain a third hole-transport material. In this case, the HOMO level of the third hole-transport material is preferably deeper than the HOMO level described in Embodiment 1 included in the second hole-transport layer 112-2, and the difference therebetween is preferably less than or equal to 0.3 eV, further preferably less than or equal to 0.2 eV. In addition, it is further preferable that the HOMO level of the third hole-transport material be deeper than or equal to the HOMO level of the host material, in which case holes are suitably transported to the light-emitting layer, leading to a favorable lifetime and efficiency. In this case, the dibenzo[c,g]carbazole derivative of one embodiment of the present invention is suitable as the third hole-transport material used for the third hole-transport layer 112-3.

Note that in the case where the HOMO level of the light-emitting material is at the position shallower (higher) than the HOMO level of the host material, the proportion of holes injected into the light-emitting material increases depending on the position of the HOMO level of the hole-transport layer, and furthermore, the holes are trapped in the light-emitting material, which might cause a decreased lifetime due to the localization of the light-emitting region. The use of the above structure of the light-emitting device is further preferable in such a case. Examples of the device that is easily have such a structure include a blue fluorescent device. In particular, the structure of the present invention can be preferably used for an aromatic diamine compound that exhibits favorable blue fluorescence, more particularly a pyrenediamine compound and the like, so that a light-emitting device with a favorable lifetime, efficiency, and chromaticity can be obtained.

Next, examples of specific structures and materials of the above-described light-emitting device are described. As described above, the light-emitting device of one embodiment of the present invention includes, between the pair of electrodes of the first electrode 101 and the second electrode 102, the EL layer 103 including a plurality of layers; the EL layer 103 includes at least the hole-injection layer 111, the hole-transport layer 112, and the light-emitting layer 113 from the first electrode 101 side.

There is no particular limitation on the other layers included in the EL layer 103, and various layers such as a hole-injection layer, a hole-transport layer, an electron-transport layer, an electron-injection layer, a carrier-blocking layer, an exciton-blocking layer, and a charge generation layer can be employed.

The first electrode 101 is preferably formed using a metal, an alloy, or a conductive compound having a high work function (specifically, 4.0 eV or more), a mixture thereof, or the like. Specifically, for example, indium oxide-tin oxide (ITO: Indium Tin Oxide), indium oxide-tin oxide containing silicon or silicon oxide, indium oxide-zinc oxide, indium oxide containing tungsten oxide and zinc oxide (IWZO), and the like can be given. These conductive metal oxide films are usually formed by a sputtering method but may also be fabricated by application of a sol-gel method or the like. Examples of the fabrication method include a method in which an indium oxide-zinc oxide is formed by a sputtering method using a target in which 1 to 20 wt % zinc oxide is added to indium oxide. Indium oxide containing tungsten oxide and zinc oxide (IWZO) can also be formed by a sputtering method using a target containing 0.5 to 5 wt % tungsten oxide and 0.1 to 1 wt % zinc oxide with respect to indium oxide. Alternatively, gold (Au), platinum (Pt), nickel (Ni), tungsten (W), chromium (Cr), molybdenum (Mo), iron (Fe), cobalt (Co), copper (Cu), palladium (Pd), a nitride of a metal material (such as titanium nitride), and the like can be used. Graphene can also be used. Note that when a composite material described later is used for a layer in contact with the first electrode 101 in the EL layer 103, an electrode material can be selected regardless of its work function.

Figure 1B:
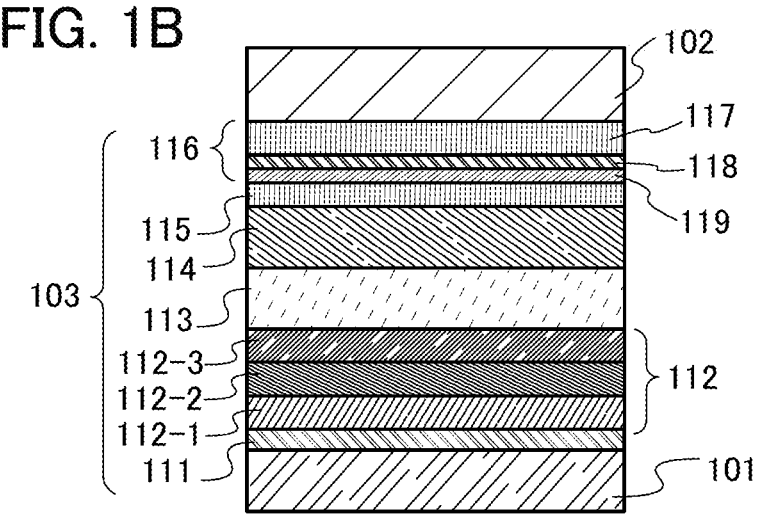

In this embodiment, two kinds of stacked-layer structures of the EL layer 103 are described: the structure including the electron-transport layer 114 and the electron-injection layer 115 in addition to the hole-injection layer 111, the hole-transport layer 112, and the light-emitting layer 113 as illustrated in FIG. 1(A); and the structure including the electron-transport layer 114, the electron-injection layer 115, and a charge generation layer 116 in addition to the hole-injection layer 111, the hole-transport layer 112, and the light-emitting layer 113 as illustrated in FIG. 1(B). Materials forming the layers are specifically described below.

The hole-injection layer 111 is a layer containing a substance having an acceptor property. The structure of one embodiment of the present invention is preferably used in the case where an organic compound having an acceptor property is used. As the organic compound having an acceptor property, a compound including an electron-withdrawing group (a halogen group or a cyano group), e.g., 7,7,8,8-tetracyano-2,3,5,6-tetrafluoroquinodimethane (abbreviation: F4-TCNQ), 3,6-difluoro-2,5,7,7,8,8-hexacyanoquinodimethane, chloranil, 2,3,6,7,10,11-hexacyano-1,4,5,8,9,12-hexaazatriphenylene (abbreviation: HAT-CN), or the like can be used. A compound in which electron-withdrawing groups are bonded to a condensed aromatic ring having a plurality of hetero atoms, like HAT-CN, is preferred as the organic compound having an acceptor property because it is thermally stable. The organic compound having an acceptor property can extract electrons from an adjacent hole-transport layer (or hole-transport material) when an electric field is applied.

In the case where the organic compound having an acceptor property is not used for the hole-injection layer 111, molybdenum oxide, vanadium oxide, ruthenium oxide, tungsten oxide, manganese oxide, or the like can be used as the substance having an acceptor property. Alternatively, the hole-injection layer 111 can be formed using phthalocyanine-based compounds such as phthalocyanine (abbreviation: $H_2Pc$) and copper phthalocyanine (CuPC); aromatic amine compounds such as 4,4'-bis[N-(4-diphenylaminophenyl)-N-phenylamino]biphenyl (abbreviation: DPAB) and N,N'-bis{4-[bis(3-methylphenyl)amino]phenyl}-N,N'-diphenyl-(1,1'-biphenyl)-4,4'-diamine (abbreviation: DNTPD); high molecular compounds such as poly(3,4-ethylenedioxythiophene)/poly(styrenesulfonic acid) (abbreviation: PEDOT/PSS); or the like.

A composite material in which a substance having a hole-transport property contains an acceptor substance can also be used for the hole-injection layer 111. Note that when the composite material in which a hole-transport substance contains an acceptor substance is used, a material used to form the electrode can be selected regardless of its work function. In other words, besides a material having a high work function, a material having a low work function can also be used for the first electrode 101. Examples of the acceptor substance include an organic compound having an acceptor property, such as 7,7,8,8-tetracyano-2,3,5,6-tetrafluoroquinodimethane (abbreviation: F4-TCNQ), chloranil, or 1,3,4,5,7,8-hexafluorotetracyano-naphthoquinodimethane (abbreviation: F6-TCNNQ), and a transition metal oxide. In addition, oxides of metals belonging to Group 4 to Group 8 of the periodic table can be used. As the oxide of a metal belonging to Group 4 to Group 8 in the periodic table, vanadium oxide, niobium oxide, tantalum oxide, chromium oxide, molybdenum oxide, tungsten oxide, manganese oxide, rhenium oxide, or the like is preferable since their acceptor property is high. Among these, molybdenum oxide is especially preferable since it is stable in the air, has a low hygroscopic property, and is easy to handle.

As the hole-transport substance used as the composite material, a variety of organic compounds such as an aromatic amine compound, a carbazole derivative, an aromatic hydrocarbon, and a high molecular compound (an oligomer, a dendrimer, a polymer, or the like) can be used. Note that the hole-transport substance used for the composite material is preferably a substance having a hole mobility of $10^{-6}$ $cm^2/Vs$ or higher. Organic compounds that can be used as the hole-transport substance in the composite material are specifically given below.

Examples of the aromatic amine compound, which can be used as the composite material, include N,N'-di(p-tolyl)-N,N'-diphenyl-p-phenylenediamine (abbreviation: DTDPPA), 4,4'-bis[N-(4-diphenylaminophenyl)-N-phenylamino]biphenyl (abbreviation: DPAB), N,N'-bis{4-[bis(3-methylphenyl)amino]phenyl}-N,N'-diphenyl-(1,1'-biphenyl)-4,4'-diamine (abbreviation: DNTPD), and 1,3,5-tris[N-(4-diphenylaminophenyl)-N-phenylamino]benzene (abbreviation: DPA3B). As the carbazole derivative, specifically, it is preferable to use 3-[N-(9-phenylcarbazol-3-yl)-N-phenylamino]-9-phenylcarbazole (abbreviation: PCzPCA1), 3,6-bis[N-(9-phenylcarbazol-3-yl)-N-phenylamino]-9-phenylcarbazole (abbreviation: PCzPCA2), 3-[N-(1-naphthyl)-N-(9-phenylcarbazol-3-yl)amino]-9-phenylcarbazole (abbreviation: PCzPCN1), 4,4'-di(N-carbazolyl)biphenyl (abbreviation: CBP), 1,3,5-tris[4-(N-carbazolyl)phenyl]benzene (abbreviation: TCPB), 9-[4-(N-carbazolyl)phenyl]-10-phenylanthracene (abbreviation: CzPA), 1,4-bis[4-(N-carbazolyl)phenyl]-2,3,5,6-tetraphenylbenzene, and the like. Examples of the aromatic hydrocarbon include 2-tert-butyl-9,10-di(2-naphthyl)anthracene (abbreviation: t-BuDNA), 2-tert-butyl-9,10-di(1-naphthyl)anthracene, 9,10-bis(3,5-diphenylphenyl)anthracene (abbreviation: DPPA), 2-tert-butyl-9,10-bis(4-phenylphenyl)anthracene (abbreviation: t-BuDBA), 9,10-di(2-naphthyl)anthracene (abbreviation: DNA), 9,10-diphenylanthracene (abbreviation: DPAnth), 2-tert-butylanthracene (abbreviation: t-BuAnth), 9,10-bis(4-methyl-1-naphthyl)anthracene (abbreviation: DMNA), 2-tert-butyl-9,10-bis[2-(1-naphthyl) phenyl]anthracene, 9,10-bis[2-(1-naphthyl)phenyl]anthracene, 2,3,6,7-tetramethyl-9,10-di(1-naphthyl)anthracene, 2,3,6,7-tetramethyl-9,10-di(2-naphthyl)anthracene, 9,9'-bianthryl, 10,10'-diphenyl-9,9'-bianthryl, 10,10'-bis(2-phenylphenyl)-9,9'-bianthryl, 10,10'-bis[(2,3,4,5,6-pentaphenyl)phenyl]-9,9'-bianthryl, anthracene, tetracene, rubrene, perylene, 2,5,8,11-tetra(tert-butyl)perylene, and the like. Alternatively, pentacene, coronene, and the like can be used. The aromatic hydrocarbon may have a vinyl skeleton. Examples of the aromatic hydrocarbon having a vinyl group include 4,4'-bis(2,2-diphenylvinyl)biphenyl (abbreviation: DPVBi) and 9,10-bis[4-(2,2-diphenylvinyl)phenyl]anthracene (abbreviation: DPVPA). Note that the organic compound of one embodiment of the present invention can also be used. In this case, F6-TCNNQ is preferably used as the acceptor substance.

Alternatively, high molecular compounds such as poly(N-vinylcarbazole) (abbreviation: PVK), poly(4-vinyltriphenylamine) (abbreviation: PVTPA), poly[N-(4-{N'-[4-(4-diphenylamino)phenyl]phenyl-N'-phenylamino}phenyl) methacrylamide] (abbreviation: PTPDMA), and poly[N,N'-bis(4-butylphenyl)-N,N'-bis(phenyl)benzidine] (abbreviation: Poly-TPD) can also be used.

The formation of the hole-injection layer 111 can improve the hole-injection property, whereby a light-emitting device with a low driving voltage can be obtained. In addition, the organic compound having an acceptor property is a material easy to use because it is easily deposited by evaporation.

The hole-transport layer 112 is formed using a hole-transport material. The hole-transport material preferably has a hole mobility higher than or equal to $1\times10^{-6}$ cm$^2$/Vs. The hole-transport layer 112 preferably contains the hole-transport material of one embodiment of the present invention. When the hole-transport layer 112 contains the dibenzo [c,g]carbazole derivative described in Embodiment 1, a light-emitting device with a long lifetime and favorable efficiency can be obtained.

In the case where the organic compound having an acceptor property is used for the hole-injection layer 111, a structure is employed in which the hole-transport layer 111 is formed of three layers of the first hole-transport layer, the second hole-transport layer, and the third transport layer; the first hole-transport layer contains the first hole-transport material with a relatively shallow HOMO level; the second hole-transport layer contains the second hole-transport material with a HOMO level between the HOMO level of the first hole-transport layer and the HOMO level of the light-emitting layer; and the third hole-transport layer contains the dibenzo[c,g]carbazole derivative of one embodiment of the present invention, whereby the light-emitting device with a long lifetime and high efficiency can be obtained.

Although the difference between the LUMO level of the organic compound having an acceptor property and the HOMO level of the first hole-transport material is not particularly limited because it depends on the strength of the acceptor property of the organic compound having an acceptor property, holes can be injected when the difference between the levels is less than or equal to approximately 1 eV. Since the LUMO level of HAT-CN is estimated to be −4.41 eV by cyclic voltammetry measurement, in the case where HAT-CN is used as the organic compound having an acceptor property, the HOMO level of the first hole-transport material is preferably greater than or equal to −5.4 eV. Note that if the HOMO level of the first hole-transport material is too high, the hole-injection property for the second hole-transport material deteriorates. In addition, since the work function of an anode such as ITO is approximately −5 eV, the use of the first hole-transport material with a HOMO level higher than −5 eV brings a disadvantage. Therefore, the HOMO level of the first hole-transport material is preferably less than or equal to −5.0 eV.

The first hole-transport layer, the second hole-transport layer, and the third hole-transport layer are described above, and thus the repeated descriptions are omitted. Note that as the hole-transport material included in each hole-transport layer, a material selected from the aforementioned materials having hole-transport properties or other various materials having hole-transport properties can be used so that the layers have an appropriate relationship.

The light-emitting layer 113 is a layer containing the host material and the light-emitting material. The light-emitting material may be fluorescent substances, phosphorescent substances, substances exhibiting thermally activated delayed fluorescence (TADF), or other light-emitting materials. Furthermore, the light-emitting layer 113 may be a single layer or be formed of a plurality of layers including different light-emitting materials. Note that one embodiment of the present invention is more preferably used in the case where the light-emitting layer 113 is a layer that exhibits fluorescence, specifically, a layer that exhibits blue fluorescence. Furthermore, the dibenzo[c,g]carbazole derivative of one embodiment of the present invention can be used as the host material, and is particularly suitable for the host material for a blue fluorescent material.

Examples of a material that can be used as a fluorescent substance in the light-emitting layer 113 are as follows. Fluorescent substances other than those given below can also be used.

For example, 5,6-bis[4-(10-phenyl-9-anthryl)phenyl]-2,2'-bipyridine (abbreviation: PAP2BPy), 5,6-bis[4'-(10-phenyl-9-anthryl)biphenyl-4-yl]-2,2'-bipyridine (abbreviation: PAPP2BPy), (N,N'-diphenyl-N,N'-bis[4-(9-phenyl-9H-fluoren-9-yl)phenyl]pyrene-1,6-diamine), N,N'-bis(3-methylphenyl)-N,N'-bis[3-(9-phenyl-9H-fluoren-9-yl)phenyl]-pyrene-1,6-diamine (abbreviation: 1,6mMemFLPAPrn), N,N'-bis[4-(9H-carbazol-9-yl)phenyl]-N,N'-diphenyl stilbene-4,4'-diamine (abbreviation: YGA2S), 4-(9H-carbazol-9-yl)-4'-(10-phenyl-9-anthryl)triphenylamine (abbreviation:

YGAPA), 4-(9H-carbazol-9-yl)-4'-(9,10-diphenyl-2-anthryl)triphenylamine (abbreviation: 2YGAPPA), N, 9-diphenyl-N-[4-(10-phenyl-9-anthryl)phenyl]-9H-carbazol-3-amine (abbreviation: PCAPA), perylene, 2,5,8,11-tetra-tert-butylperylene (abbreviation: TBP), 4-(10-phenyl-9-anthryl)-4'-(9-phenyl-9H-carbazol-3-yl)triphenylamine (abbreviation: PCBAPA), N,N''-(2-tert-butylanthracene-9,10-diyldi-4,1-phenylene)bis[N,N',N'-triphenyl-1,4-phenylenediamine] (abbreviation: DPABPA), N,9-diphenyl-N-[4-(9,10-diphenyl-2-anthryl)phenyl]-9H-carbazol-3-amine (abbreviation: 2PCAPPA), N-[4-(9,10-diphenyl-2-anthryl)phenyl]-N,N',N'-triphenyl-1,4-phenylenediamine (abbreviation: 2DPAPPA), N,N,N',N',N'',N'',N''',N'''-octaphenyldibenzo[g,p]chrysene-2,7,10,15-tetraamine (abbreviation: DBC1), coumarin 30, N-(9,10-diphenyl-2-anthryl)-N, 9-diphenyl-9H-carbazol-3-amine (abbreviation: 2PCAPA), N-[9,10-bis(1,1'-biphenyl-2-yl)-2-anthryl]-N,9-diphenyl-9H-carbazol-3-amine (abbreviation: 2PCABPhA), N-(9,10-diphenyl-2-anthryl)-N,N',N'-triphenyl-1,4-phenylenediamine (abbreviation: 2DPAPA), N-[9,10-bis(1,1'-biphenyl-2-yl)-2-anthryl]-N,N',N-triphenyl-1,4-phenylenediamine (abbreviation: 2DPABPhA), 9,10-bis(1,1'-biphenyl-2-yl)-N-[4-(9H-carbazol-9-yl)phenyl]-N-phenylanthracen-2-amine (abbreviation: 2YGABPhA), N,N,9-triphenylanthracen-9-amine (abbreviation: DPhAPhA) coumarin 545T, N,N'-diphenylquinacridone (abbreviation: DPQd), rubrene, 5,12-bis(1,1'-biphenyl-4-yl)-6,11-diphenyltetracene (abbreviation: BPT), 2-(2-{2-[4-(dimethylamino)phenyl]ethenyl}-6-methyl-4H-pyran-4-ylidene)propanedinit rile (abbreviation: DCM1), 2-{2-methyl-6-[2-(2,3,6,7-tetrahydro-1H,5H-benzo[ij]quinolizin-9-yl)ethenyl]-4H-pyran-4-ylidene}propanedinitrile (abbreviation: DCM2), N,N,N',N'-tetrakis(4-methylphenyl)tetracene-5,11-diamine (abbreviation: p-mPhTD), 7,14-diphenyl-N,N,N',N'-tetrakis(4-methylphenyl)acenaphtho[1,2-a]fluoranthene-3,10-diamine (abbreviation: p-mPhAFD), 2-{2-isopropyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTI), 2-{2-tert-butyl-6-[2-(1,1,7,7-tetramethyl-2,3,6,7-tetrahydro-1H,5H-benzo[ij]quinolizin-9-yl)ethenyl]-4H-pyran-4-ylidene}propanedinitrile (abbreviation: DCJTB), 2-(2,6-bis{2-[4-(dimethylamino)phenyl]ethenyl}-4H-pyran-4-ylidene)propanedinitrile (abbreviation: BisDCM), and 2-{2,6-bis[2-(8-methoxy-1,1,7,7-tetramethyl-2,3,6,7-tetrahydro-1H,5H-benzo[ij]quinolizin-9-yl)ethenyl]-4H-pyran-4-ylidene}propanedinitrile (abbreviation: BisDCJTM) can be given. In particular, a condensed aromatic diamine compound typified by a pyrenediamine compound such as 1,6FLPAPrn, 1,6mMemFLPAPrn, and 1,6BnfAPrn-03 is preferable because of its high hole-trapping property, high emission efficiency, and high reliability.

Examples of a material that can be used as a phosphorescent substance in the light-emitting layer 113 are as follows.

An organometallic iridium complex having a 4H-triazole skeleton, such as tris{2-[5-(2-methylphenyl)-4-(2,6-dimethylphenyl)-4H-1,2,4-triazol-3-yl-κN2]phenyl-κ C}iridium (III) (abbreviation: [Ir(mpptz-dmp)$_3$]), tris(5-methyl-3,4-diphenyl-4H-1,2,4-triazolato)iridium(III) (abbreviation: [Ir(Mptz)$_3$]), or tris[4-(3-biphenyl)-5-isopropyl-3-phenyl-4H-1,2,4-triazolato]iridium(III) (abbreviation: [Ir(iPrptz-3b)$_3$]), an organometallic iridium complex having a 1H-triazole skeleton, such as tris[3-methyl-1-(2-methylphenyl)-5-phenyl-1H-1,2,4-triazolato]iridium(III) (abbreviation: [Ir(Mptz1-mp)$_3$]) or tris(1-methyl-5-phenyl-3-propyl-1H-1,2,4-triazolato)iridium(III) (abbreviation: [Ir(Prptz1-Me)$_3$]), an organometallic iridium complex having an imidazole skeleton, such as fac-tris[1-(2,6-diisopropylphenyl)-2-phenyl-1H-imidazole]iridium(III) (abbreviation: [Ir(iPrpmi)$_3$]) or tris[3-(2,6-dimethylphenyl)-7-methylimidazo[1,2-f]phenanthridinato]iridium(III) (abbreviation: [Ir(dmpimpt-Me)$_3$]), and an organometallic iridium complex in which a phenylpyridine derivative having an electron-withdrawing group is a ligand, such as bis[2-(4',6'-difluorophenyl)pyridinato-N,C$^{2'}$]iridium(III) tetrakis(1-pyrazolyl)borate (abbreviation: FIr6), bis[2-(4',6'-difluorophenyl)pyridinato-N,C$^{2'}$]iridium(III) picolinate (abbreviation: FIrpic), bis{2-[3',5'-bis(trifluoromethyl)phenyl]pyridinato-N,C$^{2'}$}iridium(III) picolinate (abbreviation: [Ir(CF$_3$ppy)$_2$(pic)]), or bis[2-(4',6'-difluorophenyl)pyridinato-N,C$^{2'}$]iridium(III) acetylacetonate (abbreviation: FIracac) can be given. These are compounds exhibiting blue phosphorescence, and are compounds having an emission peak at 440 nm to 520 nm.

Furthermore, an organometallic iridium complex having a pyrimidine skeleton, such as tris(4-methyl-6-phenylpyrimidinato)iridium(III) (abbreviation: [Ir(mppm)$_3$]), tris(4-t-butyl-6-phenylpyrimidinato)iridium(III) (abbreviation: [Ir(t-Buppm)$_3$]), (acetylacetonato)bis(6-methyl-4-phenylpyrimidinato)iridium(III) (abbreviation: [Ir(mppm)$_2$(acac)]), (acetylacetonato)bis(6-tert-butyl-4-phenylpyrimidinato)iridium(III) (abbreviation: [Ir(tBuppm)$_2$(acac)]), (acetylacetonato)bis[6-(2-norbornyl)-4-phenylpyrimidinato]iridium(III) (abbreviation: [Ir(nbppm)$_2$(acac)]), (acetylacetonato)bis[5-methyl-6-(2-methylphenyl)-4-phenylpyrimidinato]iridium(III) (abbreviation: [Ir(mpmppm)$_2$(acac)]), or (acetylacetonato)bis(4,6-diphenylpyrimidinato)iridium(III) (abbreviation: [Ir(dppm)$_2$(acac)]), an organometallic iridium complex having a pyrazine skeleton, such as (acetylacetonato)bis(3,5-dimethyl-2-phenylpyrazinato)iridium(III) (abbreviation: [Ir(mppr-Me)$_2$(acac)]) or (acetylacetonato)bis(5-isopropyl-3-methyl-2-phenylpyrazinato)iridium(III) (abbreviation: [Ir(mppr-iPr)$_2$(acac)]), an organometallic iridium complex having a pyridine skeleton, such as tris(2-phenylpyridinato-N,C$^{2'}$)iridium(III) (abbreviation: [Ir(ppy)$_3$]), bis(2-phenylpyridinato-N,C$^{2'}$)iridium(III) acetylacetonate (abbreviation: [Ir(ppy)$_2$(acac)]), bis(benzo[h]quinolinato)iridium(III) acetyl acetonate (abbreviation: [Ir(bzq)$_2$(acac)]), tris(benzo[h]quinolinato)iridium(III) (abbreviation: [Ir(bzq)$_3$]), tris(2-phenylquinolinato-N,C$^{2'}$)iridium(III) (abbreviation: [Ir(pq)$_3$]), or bis(2-phenylquinolinato-N,C$^{2'}$)iridium(III) acetyl acetonate (abbreviation: [Ir(pq)$_2$(acac)]), and a rare earth metal complex such as tris(acetylacetonato) (monophenanthroline)terbium(III) (abbreviation: [Tb(acac)$_3$(Phen)]) can be given. These are mainly compounds exhibiting green phosphorescence, and have an emission peak at 500 nm to 600 nm. Note that an organometallic iridium complex having a pyrimidine skeleton is particularly preferable because of its distinctively high reliability and emission efficiency.

Furthermore, an organometallic iridium complex having a pyrimidine skeleton, such as (diisobutyrylmethanato)bis[4,6-bis(3-methylphenyl)pyrimidinato]iridium(III) (abbreviation: [Ir(5mdppm)$_2$(dibm)]), bis[4,6-bis(3-methylphenyl)pyrimidinato] (dipivaloylmethanato)iridium(III)

(abbreviation: [Ir(5mdppm)$_2$(dpm)]), or bis[4,6-di(naphthalen-1-yl)pyrimidinato](dipivaloylmethanato)iridium(III) (abbreviation: [Ir(d1npm)$_2$(dpm)]), an organometallic iridium complex having a pyrazine skeleton, such as (acetylacetonato)bis(2,3,5-triphenylpyrazinato)iridium(III) (abbreviation: [Ir(tppr)$_2$(acac)]), bis(2,3,5-triphenylpyrazinato)(dipivaloylmethanato)iridium(III) (abbreviation: [Ir(tppr)$_2$(dpm)]), or (acetylacetonato)bis[2,3-bis(4-fluorophenyl)quinoxalinato]iridium(III) (abbreviation: [Ir(Fdpq)$_2$(acac)]), an organometallic iridium complex having a pyridine skeleton, such as tris(1-phenylisoquinolinato-N,C$^{2'}$)iridium(III) (abbreviation: [Ir(piq)$_3$]) or bis(1-phenylisoquinolinato-N,C$^{2'}$)iridium(III) acetylacetonate (abbreviation: [Ir(piq)$_2$(acac)]), a platinum complex such as 2,3,7,8,12,13,17,18-octaethyl-21H,23H-porphyrin platinum(II) (abbreviation: PtOEP), and a rare earth metal complex such as tris(1,3-diphenyl-1,3-propanedionato) (monophenanthroline)europium(III) (abbreviation: [Eu(DBM)$_3$(Phen)]) or tris[1-(2-thenoyl)-3,3,3-trifluoroacetonato] (monophenanthroline) europium(III) (abbreviation: [Eu(TTA)$_3$(Phen)]) can be given. These are compounds exhibiting red phosphorescence, and have an emission peak at 600 nm to 700 nm. Furthermore, from the organometallic iridium complex having a pyrazine skeleton, red light emission with favorable chromaticity can be obtained.

Besides the above-described phosphorescent compounds, other known phosphorescent materials may be selected and used.

As the TADF material, a fullerene, a derivative thereof, an acridine, a derivative thereof, an eosin derivative, or the like can be used. Other examples include a metal-containing porphyrin containing magnesium (Mg), zinc (Zn), cadmium (Cd), tin (Sn), platinum (Pt), indium (In), palladium (Pd), or the like. Examples of the metal-containing porphyrin include a protoporphyrin-tin fluoride complex (SnF$_2$(Proto IX)), a mesoporphyrin-tin fluoride complex (SnF$_2$(Meso IX)), a hematoporphyrin-tin fluoride complex (SnF$_2$(Hemato IX)), a coproporphyrin tetramethyl ester-tin fluoride complex (SnF$_2$(Copro III-4Me)), an octaethylporphyrin-tin fluoride complex (SnF$_2$(OEP)), an etioporphyrin-tin fluoride complex (SnF$_2$(Etio I)), and an octaethylporphyrin-platinum chloride complex (PtCl$_2$(OEP)), which are represented by the following structural formulae.

[Chemical Formula 25]

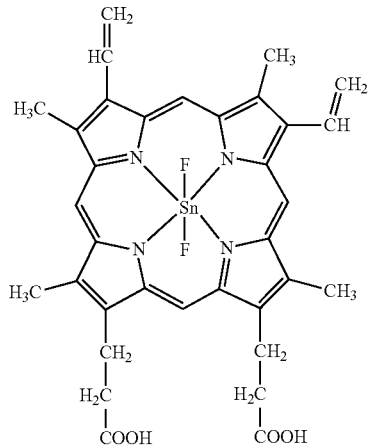

SnF$_2$(Proto IX)

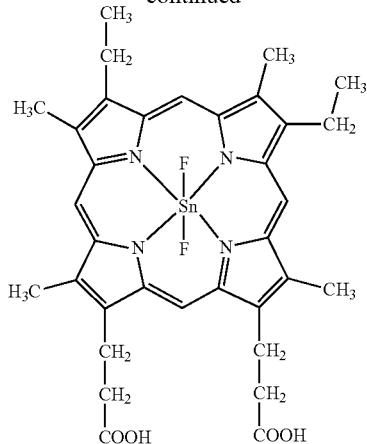

SnF$_2$(Meso IX)

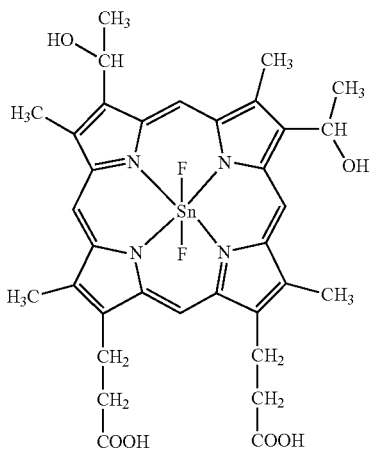

SnF$_2$(Hemato IX)

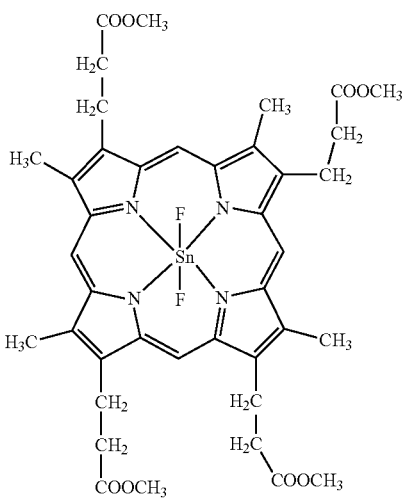

SnF$_2$(Copro III-4Me)

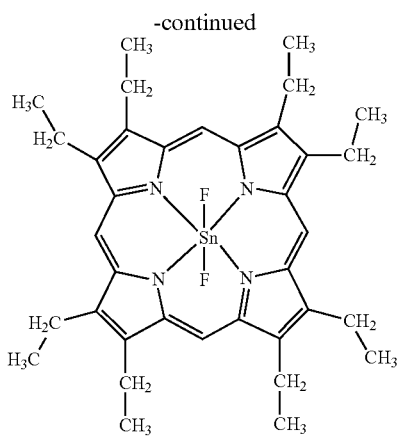

SnF₂(OEP)

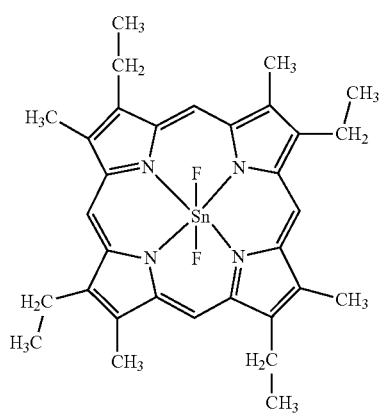

SnF₂(EtiO I)

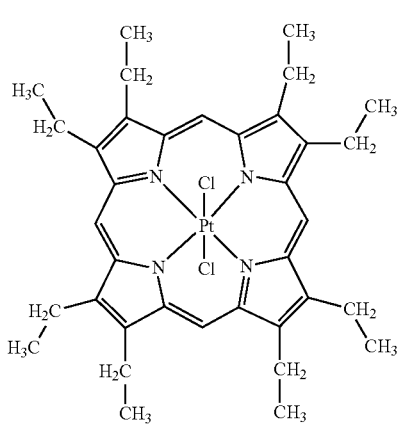

PtCl₂OEP

Alternatively, a heterocyclic compound having both a π-electron rich heteroaromatic ring and a π-electron deficient heteroaromatic ring, such as 2-(biphenyl-4-yl)-4,6-bis(12-phenylindolo[2,3-a]carbazol-11-yl)-1,3,5-triazine (abbreviation: PIC-TRZ), 9-(4,6-diphenyl-1,3,5-triazin-2-yl)-9'-phenyl-9H,9'H-3,3'-bicarbazole (abbreviation: PCCzTzn), 2-{4-[3-(N-phenyl-9H-carbazol-3-yl)-9H-carbazol-9-yl]phenyl}-4,6-diphenyl-1,3,5-triazine (abbreviation: PCCzPTzn), 2-[4-(10H-phenoxazine-10-yl)phenyl]-4,6-diphenyl-1,3,5-triazine (abbreviation: PXZ-TRZ), 3-[4-(5-phenyl-5,10-dihydrophenazin-10-yl)phenyl]-4,5-diphenyl-1,2,4-triazole (abbreviation: PPZ-3 TPT), 3-(9,9-dimethyl-9H-acridin-10-yl)-9H-xanthen-9-one (abbreviation: ACRXTN), bis[4-(9,9-dimethyl-9,10-dihydroacridine)phenyl]sulfone (abbreviation: DMAC-DPS), or 10-phenyl-10H,10'H-spiro[acridin-9,9'-anthracen]-10'-one (abbreviation: ACRSA), which are represented by the following structural formulae, can be used. The heterocyclic compound is preferable because of having both a high electron-transport property and a high hole-transport property owing to a π-electron rich heteroaromatic ring and a π-electron deficient heteroaromatic ring. Note that a substance in which the π-electron rich heteroaromatic ring and the π-electron deficient heteroaromatic ring are directly bonded to each other is particularly preferable because the donor property of the π-electron rich heteroaromatic ring and the acceptor property of the π-electron deficient heteroaromatic ring are both increased and the energy difference between the S1 level and the T1 level becomes small, so that thermally activated delayed fluorescence can be obtained with high efficiency. Note that an aromatic ring to which an electron-withdrawing group such as a cyano group is bonded may be used instead of the π-electron deficient heteroaromatic ring.

[Chemical Formula 26]

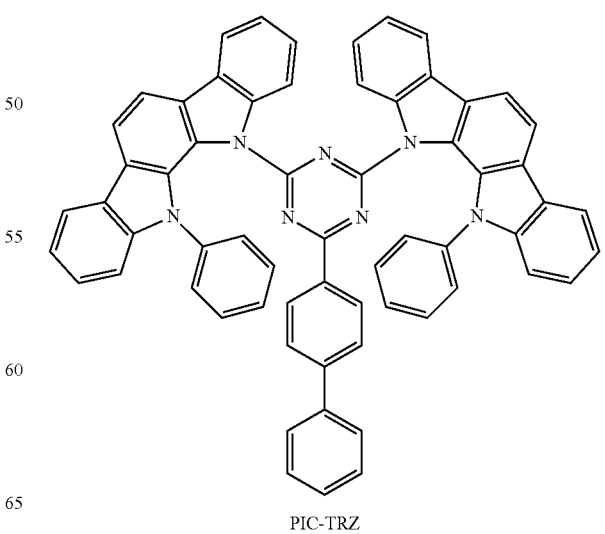

PIC-TRZ

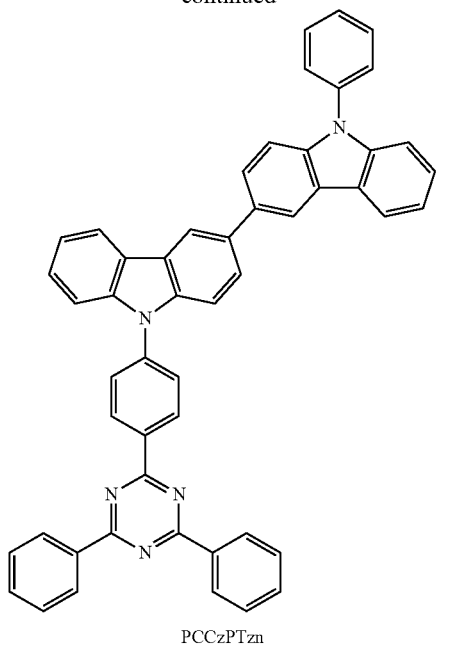

PCCzPTzn

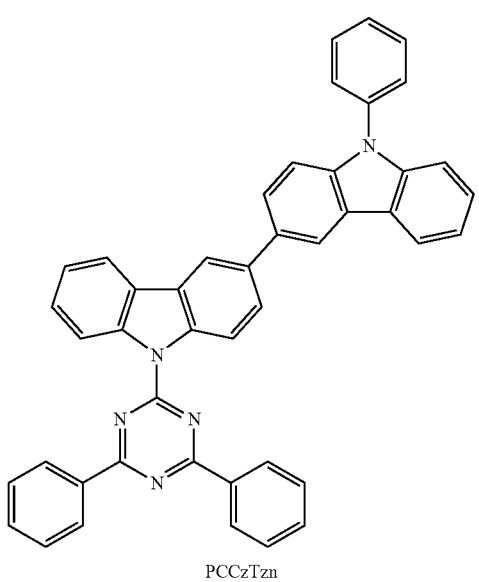

PCCzTzn

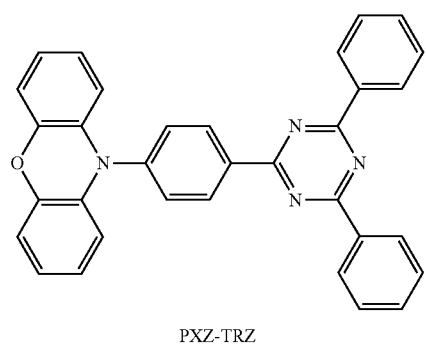

PXZ-TRZ

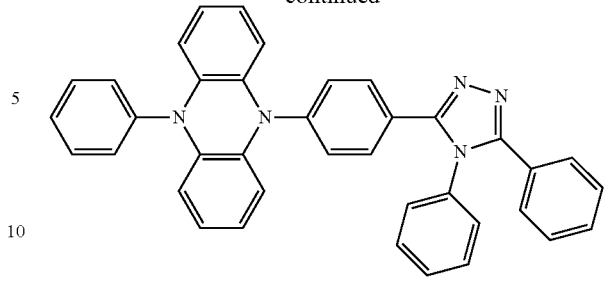

PPZ-3TPT

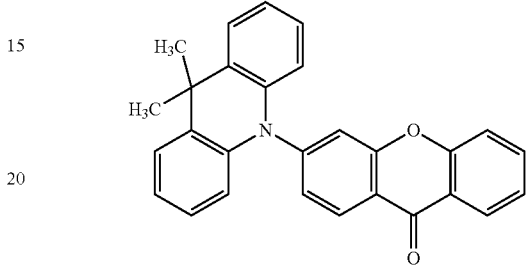

ACRXTN

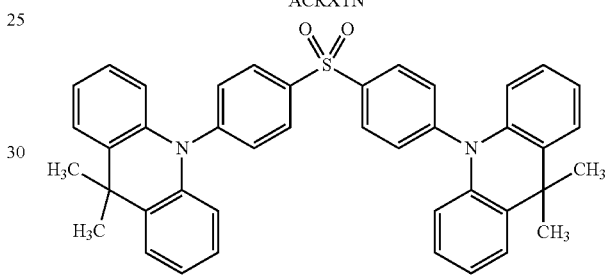

DMAC-DPS

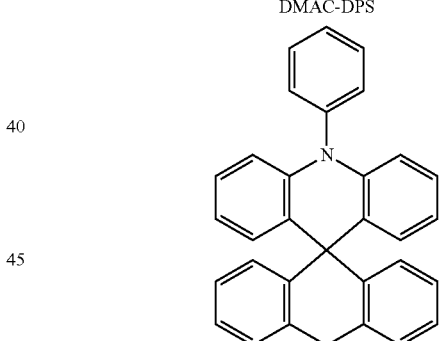

ACRSA

As the host material in the light-emitting layer, a variety of carrier-transport materials such as a material having an electron-transport property and a material having a hole-transport property can be used.

As a material having a hole-transport property, a compound having an aromatic amine skeleton, such as 4,4'-bis[N-(1-naphthyl)-N-phenylamino]biphenyl (abbreviation: NPB), N,N'-bis(3-methylphenyl)-N,N'-diphenyl-[1,1'-biphenyl]-4,4'-diamine (abbreviation: TPD), 4,4'-bis[N-(spiro-9,9'-bifluoren-2-yl)-N-phenylamino]biphenyl (abbreviation: BSPB), 4-phenyl-4'-(9-phenylfluoren-9-yl)triphenylamine (abbreviation: BPAFLP), 4-phenyl-3'-(9-phenylfluoren-9-yl)triphenylamine (abbreviation: mBPAFLP), 4-phenyl-4'-(9-phenyl-9H-carbazol-3-yl)triphenylamine (abbreviation: PCBA1BP), 4,4'-diphenyl-4''-(9-phenyl-9H-carbazol-3-yl)triphenylamine (abbreviation: PCBBi1BP), 4-(1-naphthyl)-4'-(9-phenyl-9H-carbazol-3-yl)-triphenylamine (abbreviation: PCBANB), 4,4'-di(1-naphthyl)-4''-(9-phenyl-9H-carbazol-3-yl)triphenylamine (abbreviation: PCBNBB), 9,9-dimethyl-N-phenyl-N-[4-(9-phenyl-9H-carbazol-3-yl)phenyl]fluoren-2-amine (abbreviation: PCBAF), or N-phenyl-N-[4-(9-phenyl-9H-carbazol-3-yl)phenyl]spiro-9,9'-bifluoren-2-amine (abbreviation: PCBASF), a compound having a carbazole skeleton, such as 1,3-bis(N-carbazolyl)benzene (abbreviation: mCP), 4,4'-di (N-carbazolyl)biphenyl (abbreviation: CBP), 3,6-bis(3,5-diphenylphenyl)-9-phenylcarbazole (abbreviation: CzTP), or 3,3'-bis(9-phenyl-9H-carbazole) (abbreviation: PCCP), a compound having a thiophene skeleton, such as 4,4',4''-(benzene-1,3,5-triyl)tri(dibenzothiophene) (abbreviation: DBT3P-II), 2,8-diphenyl-4-[4-(9-phenyl-9H-fluoren-9-yl) phenyl]dibenzothiophene (abbreviation: DBTFLP-III), or 4-[4-(9-phenyl-9H-fluoren-9-yl)phenyl]-6-phenyldibenzothiophene (abbreviation: DBTFLP-IV), and a compound having a furan skeleton, such as 4,4',4''-(benzene-1,3,5-triyl) tri(dibenzofuran) (abbreviation: DBF3P-II) or 4-{3-[3-(9-phenyl-9H-fluoren-9-yl)phenyl]phenyl}dibenzofuran (abbreviation: mmDBFFLBi-II) can be given. Among the above, the compound having an aromatic amine skeleton and the compound having a carbazole skeleton are preferable because these have favorable reliability, have high hole-transport properties, and contribute to a reduction in driving voltage. The organic compound described in Embodiment 1 can also be suitably used.

As the material having an electron-transport property, for example, a metal complex such as bis(10-hydroxybenzo[h] quinolinato)beryllium(II) (abbreviation: BeBq$_2$), bis(2-methyl-8-quinolinolato)(4-phenylphenolato)aluminum(III) (abbreviation: BAlq), bis(8-quinolinolato)zinc(II) (abbreviation: Znq), bis[2-(2-benzoxazolyl)phenolato]zinc(II) (abbreviation: ZnPBO), or bis[2-(2-benzothiazolyl)phenolato] zinc(II) (abbreviation: ZnBTZ), a heterocyclic compound having a polyazole skeleton, such as 2-(4-biphenylyl)-5-(4-tert-butylphenyl)-1,3,4-oxadiazole (abbreviation: PBD), 3-(4-biphenylyl)-4-phenyl-5-(4-tert-butylphenyl)-1,2,4-triazole (abbreviation: TAZ), 1,3-bis[5-(p-tert-butylphenyl)-1, 3,4-oxadiazol-2-yl]benzene (abbreviation: OXD-7), 9-[4-(5-phenyl-1,3,4-oxadiazol-2-yl)phenyl]-9H-carbazole (abbreviation: CO11), 2,2',2''-(1,3,5-benzenetriyl)tris(1-phenyl-1H-benzimidazole) (abbreviation: TPBI), or 2-[3-(dibenzothiophen-4-yl)phenyl]-1-phenyl-1H-benzimidazole (abbreviation: mDBTBIm-II), a heterocyclic compound having a diazine skeleton, such as 2-[3-(dibenzothiophen-4-yl)phenyl]dibenzo[f,h]quinoxaline (abbreviation: 2mDBTPDBq-II), 2-[3'-(dibenzothiophen-4-yl)biphenyl-3-yl]dibenzo[f,h]quinoxaline (abbreviation: 2mDBTBPDBq-II), 2-[3-(9H-carbazol-9-yl)biphenyl-3-yl]dibenzo[f,h]quinoxaline (abbreviation: 2mCzBPDBq), 4,6-bis[3-(phenanthren-9-yl)phenyl]pyrimidine (abbreviation: 4,6mPnP2Pm), or 4,6-bis[3-(4-dibenzothienyl)phenyl]pyrimidine (abbreviation: 4,6mDBTP2Pm-II), and a heterocyclic compound having a pyridine skeleton, such as 3,5-bis [3-(9H-carbazol-9-yl)phenyl]pyridine (abbreviation: 35DCzPPy) or 1,3,5-tri[3-(3-pyridyl)phenyl]benzene (abbreviation: TmPyPB) can be given. Among the above, the heterocyclic compound having a diazine skeleton and the heterocyclic compound having a pyridine skeleton have favorable reliability and thus are preferable. In particular, the heterocyclic compound having a diazine (pyrimidine or pyrazine) skeleton has a high electron-transport property and contributes to a reduction in driving voltage.

In the case where a fluorescent substance is used as the light-emitting material, a material having an anthracene skeleton is suitable for the host material. The use of a substance having an anthracene skeleton as a host material for a fluorescent substance makes it possible to achieve a light-emitting layer with favorable emission efficiency and durability. As the substance having an anthracene skeleton that is used as the host material, a substance having a diphenylanthracene skeleton, in particular, a substance having a 9,10-diphenylanthracene skeleton, is preferable because of its chemical stability. The host material preferably has a carbazole skeleton because the hole-injection and hole-transport properties are improved; further preferably, the host material has a benzocarbazole skeleton in which a benzene ring is further condensed to carbazole because the HOMO level thereof is shallower than that of carbazole by approximately 0.1 eV and thus holes enter the host material easily. In particular, the host material having a dibenzocarbazole skeleton is preferable because its HOMO level is shallower than that of carbazole by approximately 0.1 eV so that holes enter the host material easily, the hole-transport property is improved, and the heat resistance is increased. Accordingly, a substance that has both a 9,10-diphenylanthracene skeleton and a carbazole skeleton (or a benzocarbazole skeleton or a dibenzocarbazole skeleton) is further preferable as the host material. Note that in terms of the hole-injection and hole-transport properties described above, instead of a carbazole skeleton, a benzofluorene skeleton or a dibenzo fluorene skeleton may be used. Examples of such a substance include 9-phenyl-3-[4-(10-phenyl-9-anthryl)phenyl]-9H-carbazole (abbreviation: PCzPA), 3-[4-(1-naphthyl)-phenyl]-9-phenyl-9H-carbazole (abbreviation: PCPN), 9-[4-(10-phenyl-9-anthracenyl)phenyl]-9H-carbazole (abbreviation: CzPA), 7-[4-(10-phenyl-9-anthryl)phenyl]-7H-dibenzo[c,g]carbazole (abbreviation: cgDBCzPA), 6-[3-(9,10-diphenyl-2-anthryl)phenyl]-benzo [b]naphtho[1,2-d]furan (abbreviation: 2mBnfPPA), and 9-phenyl-10-{4-(9-phenyl-9H-fluoren-9-yl)-biphenyl-4'-yl}-anthracene (abbreviation: FLPPA). In particular, CzPA, cgDBCzPA, 2mBnfPPA, and PCzPA are preferably selected because they exhibit favorable characteristics. Note that the dibenzo[c,g]carbazole derivative of one embodiment of the present invention is extremely suitable for a material for the hole-transport layer that is adjacent to the light-emitting layer of a fluorescent light-emitting device using any of these host materials.

Note that a host material may be a material of a mixture of a plurality of kinds of substances; in the case of using a mixed host material, it is preferable to mix a material having an electron-transport property with a material having a hole-transport property. When the material having an electron-transport property is mixed with the material having a hole-transport property, the transport property of the light-emitting layer 113 can be easily adjusted and a recombination region can be easily controlled. The ratio of the content of the material having a hole-transport property to the content of the material having an electron-transport property may be the material having a hole-transport property: the material having an electron-transport property=1:9 to 9:1.

These mixed host materials may form an exciplex. A combination is preferably selected so as to form an exciplex that exhibits light emission whose wavelength overlaps with the wavelength of a lowest-energy-side absorption band of a light-emitting material, because energy can be transferred smoothly and light emission can be efficiently obtained. The use of the structure is preferable because the driving voltage is also be reduced.

The electron-transport layer 114 is a layer containing a substance having an electron-transport property. As the substance having an electron-transport property, it is possible to use any of the above-listed substances having electron-transport properties that can be used as the host material.

As the electron-injection layer 115, a layer containing an alkali metal, an alkaline earth metal, or a compound thereof, such as lithium fluoride (LiF), cesium fluoride (CsF), or calcium fluoride (CaF2), may be provided between the electron-transport layer 114 and the second electrode 102. For example, an electride or a layer that is formed using a substance having an electron-transport property and that includes an alkali metal, an alkaline earth metal, or a compound thereof can be used as the electron-injection layer 115. Examples of the electride include a substance in which electrons are added at high concentration to a mixed oxide of calcium and aluminum.

Instead of the electron-injection layer 115, the charge generation layer 116 may be provided (FIG. 1(B)). The charge generation layer 116 refers to a layer capable of injecting holes into a layer in contact therewith on the cathode side and injecting electrons into a layer in contact therewith on the anode side when supplied with a potential. The charge generation layer 116 includes at least a P-type layer 117. The P-type layer 117 is preferably formed using the composite materials given above as the material that can form the hole-injection layer 111. The P-type layer 117 may be formed by stacking a film containing the above acceptor material as a material included in the composite material and a film containing the above hole-transport material. When a potential is applied to the P-type layer 117, electrons are injected into the electron-transport layer 114 and holes are injected into the second electrode 102 that is a cathode; thus, the light-emitting device operates.

Note that one or both of an electron-relay layer 118 and an electron-injection buffer layer 119 are preferably provided in the charge generation layer 116 in addition to the P-type layer 117.

The electron-relay layer 118 contains at least a substance having an electron-transport property and has a function of preventing an interaction between the electron-injection buffer layer 119 and the P-type layer 117 to transfer electrons smoothly. The LUMO level of the substance having an electron-transport property contained in the electron-relay layer 118 is preferably between the LUMO level of an acceptor substance in the P-type layer 117 and the LUMO level of a substance contained in a layer of the electron-transport layer 114 in contact with the charge generation layer 116. A specific energy level of the LUMO level of the substance having an electron-transport property used for the electron-relay layer 118 is preferably higher than or equal to −5.0 eV, further preferably higher than or equal to −5.0 eV and lower than or equal to −3.0 eV. Note that as the substance having an electron-transport property used for the electron-relay layer 118, a phthalocyanine-based material or a metal complex having a metal-oxygen bond and an aromatic ligand is preferably used.

For the electron-injection buffer layer 119, a substance having a high electron-injection property, such as an alkali metal, an alkaline earth metal, a rare earth metal, or a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)), can be used.

In the case where the electron-injection buffer layer 119 is formed so as to contain the substance having an electron-transport property and a donor substance, an organic compound such as tetrathianaphthacene (abbreviation: TTN), nickelocene, or decamethylnickelocene can be used as the donor substance, as well as an alkali metal, an alkaline earth metal, a rare earth metal, a compound thereof (an alkali metal compound (including an oxide such as lithium oxide, a halide, and a carbonate such as lithium carbonate or cesium carbonate), an alkaline earth metal compound (including an oxide, a halide, and a carbonate), or a rare earth metal compound (including an oxide, a halide, and a carbonate)). As the substance having an electron-transport property, a material similar to the above-described material included in the electron-transport layer 114 can be used.

As a substance forming the second electrode 102, a metal, an alloy, an electrically conductive compound, or a mixture thereof having a low work function (specifically, 3.8 eV or less) or the like can be used. As specific examples of such a cathode material, elements belonging to Group 1 or Group 2 of the periodic table, such as alkali metals, e.g., lithium (Li) and cesium (Cs)), magnesium (Mg), calcium (Ca), and strontium (Sr), alloys containing these (MgAg and AlLi), rare earth metals such as europium (Eu) and ytterbium (Yb), alloys containing these rare earth metals, and the like can be given. However, when the electron-injection layer is provided between the second electrode 102 and the electron-transport layer, as the second electrode 102, a variety of conductive materials such as Al, Ag, ITO, or indium oxide-tin oxide containing silicon or silicon oxide can be used regardless of their work functions. Films of these conductive materials can be formed by a dry process such as a vacuum evaporation method or a sputtering method, an inkjet method, a spin coating method, or the like. Alternatively, the films may be formed by a wet process using a sol-gel method or a wet process using a paste of a metal material.

Various methods can be used as a method for forming the EL layer 103 regardless of whether it is a dry process or a wet process. For example, a vacuum evaporation method, a gravure printing method, an offset printing method, a screen printing method, an ink-jet method, a spin coating method, or the like may be used.

Different deposition methods may be used to form the electrodes or the layers described above.

The structure of the layers provided between the first electrode 101 and the second electrode 102 is not limited to the above-described structure. However, a structure is preferable in which a light-emitting region where holes and electrons recombine is provided at a position away from the first electrode 101 and the second electrode 102 so as to prevent quenching caused by the proximity of the light-emitting region and a metal used for electrodes and carrier-injection layers.

Furthermore, in order to inhibit energy transfer from an exciton generated in the light-emitting layer, it is preferable to form the hole-transport layer and the electron-transport layer that are in contact with the light-emitting layer 113, particularly a carrier-transport layer closer to the recombination region in the light-emitting layer 113, using the light-emitting material of the light-emitting layer or a substance having a wider band gap than the light-emitting material included in the light-emitting layer.

Next, an embodiment of a light-emitting device with a structure where a plurality of light-emitting units is stacked (also referred to as a stacked-type device or a tandem device) will be described with reference to FIG. 1(C). This light-emitting device is a light-emitting device including a plurality of light-emitting units between an anode and a cathode. One light-emitting unit has substantially the same structure as that of the EL layer 103, which is illustrated in FIG. 1(A). In other words, the light-emitting device illustrated in FIG. 1(C) can be called a light-emitting device including a plurality of light-emitting units, and the light-emitting device illustrated in FIG. 1(A) or FIG. 1(B) can be called a light-emitting device including one light-emitting unit.

Figure 1C:
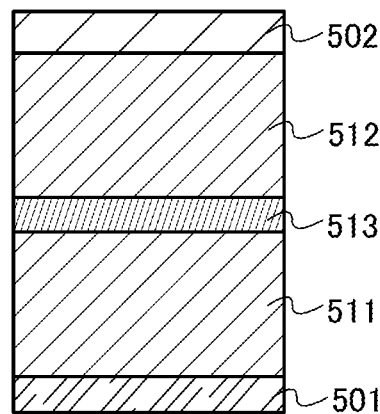

In FIG. 1(C), a first light-emitting unit 511 and a second light-emitting unit 512 are stacked between an anode 501 and a cathode 502, and a charge generation layer 513 is provided between the first light-emitting unit 511 and the second light-emitting unit 512. The anode 501 and the cathode 502 correspond, respectively, to the first electrode 101 and the second electrode 102 in FIG. 1(A), and the same material as what is given in the description for FIG. 1(A) can be used. Furthermore, the first light-emitting unit 511 and the second light-emitting unit 512 may have the same structure or different structures.

The charge generation layer 513 has a function of injecting electrons into one of the light-emitting units and injecting holes into the other of the light-emitting units when a voltage is applied to the anode 501 and the cathode 502. That is, in FIG. 1(C), any layer can be used as the charge generation layer 513 as long as the layer injects electrons into the first light-emitting unit 511 and injects holes into the second light-emitting unit 512 in the case where a voltage is applied such that the potential of the anode is higher than that of the cathode.

The charge generation layer 513 is preferably formed with a structure similar to that of the charge generation layer 116 described with reference to FIG. 1(B). A composite material of an organic compound and a metal oxide has an excellent carrier-injection property and an excellent carrier-transport property; thus, low-voltage driving and low-current driving can be achieved. Note that in the case where the anode-side surface of a light-emitting unit is in contact with the charge generation layer 513, the charge generation layer 513 can also serve as a hole-injection layer of the light-emitting unit; therefore, a hole-injection layer is not necessarily provided in the light-emitting unit.

In the case where the electron-injection buffer layer 119 is provided in the charge generation layer 513, the electron-injection buffer layer 119 serves as an electron-injection layer in the light-emitting unit on the anode side; therefore, an electron-injection layer is not necessarily formed in the light-emitting unit on the anode side.

The light-emitting device having two light-emitting units is described with reference to FIG. 1(C); however, one embodiment of the present invention can be similarly applied to a light-emitting device in which three or more light-emitting units are stacked. With a plurality of light-emitting units partitioned by the charge generation layer 513 between a pair of electrodes as in the light-emitting device according to this embodiment, it is possible to achieve a device that can emit high-luminance light with the current density kept low and has a longer lifetime. Moreover, a light-emitting apparatus that can be driven at a low voltage and has low power consumption can be achieved.

Furthermore, when emission colors of the light-emitting units are different, light emission of a desired color can be obtained from the light-emitting device as a whole. For example, in a light-emitting device having two light-emitting units, emission colors of red and green are obtained in the first light-emitting unit and an emission color of blue is obtained in the second light-emitting unit, whereby a light-emitting device that emits white light as the whole light-emitting device can be obtained.

The above-described layers and electrodes such as the EL layer 103, the first light-emitting unit 511, the second light-emitting unit 512, and the charge generation layer can be formed by a method such as an evaporation method (including a vacuum evaporation method), a droplet discharge method (also referred to as an ink-jet method), a coating method, or a gravure printing method. Those may include a low molecular material, a middle molecular material (including an oligomer and a dendrimer), or a high molecular material.

Embodiment 3

In this embodiment, a light-emitting apparatus using the light-emitting device described in Embodiment 2 will be described.

In this embodiment, a light-emitting apparatus fabricated using the light-emitting device described in Embodiment 2 will be described with reference to FIG. 2. Note that FIG. 2(A) is a top view illustrating the light-emitting apparatus, and FIG. 2(B) is a cross-sectional view taken along the dashed-dotted line A-B and the dashed-dotted line C-D in FIG. 2(A). This light-emitting apparatus includes a driver circuit portion (source line driver circuit) 601, a pixel portion 602, and a driver circuit portion (gate line driver circuit) 603, which are for controlling light emission of a light-emitting device and are illustrated with dotted lines. Furthermore, 604 denotes a sealing substrate, 605 denotes a sealant, and the inside surrounded by the sealant 605 is a space 607.

Note that a lead wiring 608 is a wiring for transmitting signals to be input to the source line driver circuit 601 and the gate line driver circuit 603 and receiving a video signal, a clock signal, a start signal, a reset signal, and the like from an FPC (flexible printed circuit) 609 serving as an external input terminal. Although only the FPC is illustrated here, a printed wiring board (PWB) may be attached to this FPC. The light-emitting apparatus in this specification includes not only the light-emitting apparatus itself but also the apparatus provided with the FPC or the PWB.

Next, a cross-sectional structure will be described with reference to FIG. 2(B). The driver circuit portion and the pixel portion are formed over an element substrate 610. Here, the source line driver circuit 601, which is the driver circuit portion, and one pixel of the pixel portion 602 are illustrated.

The element substrate 610 may be fabricated using a substrate containing glass, quartz, an organic resin, a metal, an alloy, a semiconductor, or the like, or a plastic substrate formed of FRP (Fiber Reinforced Plastic), PVF (polyvinyl fluoride), polyester, acrylic, or the like.

The structure of transistors used in pixels and driver circuits is not particularly limited. For example, an inverted staggered transistor or a staggered transistor may be used. Furthermore, top-gate transistors or bottom-gate transistors may be used. A semiconductor material used for the transistors is not particularly limited, and for example, silicon, germanium, silicon carbide, gallium nitride, or the like can be used. Alternatively, an oxide semiconductor containing at least one of indium, gallium, and zinc, such as In—Ga—Zn-based metal oxide, may be used.

There is no particular limitation on the crystallinity of a semiconductor material used for the transistors, and any of an amorphous semiconductor or a semiconductor having crystallinity (a microcrystalline semiconductor, a polycrystalline semiconductor, a single-crystal semiconductor, and a semiconductor partly including crystal regions) may be used. A semiconductor having crystallinity is preferably used, in which case deterioration of the transistor characteristics can be suppressed.

Here, an oxide semiconductor is preferably used for semiconductor devices such as the transistors provided in the pixels and driver circuits and transistors used for touch sensors described later, and the like. In particular, an oxide semiconductor having a wider band gap than silicon is preferably used. The use of an oxide semiconductor material having a wider band gap than silicon can reduce the off-state current of the transistors.

The oxide semiconductor preferably contains at least indium (In) or zinc (Zn). Further preferably, the oxide semiconductor includes an oxide represented by an In—M—Zn-based oxide (M represents a metal such as Al, Ti, Ga, Ge, Y, Zr, Sn, La, Ce, or Hf).

As a semiconductor layer, it is particularly preferable to use an oxide semiconductor film including a plurality of crystal parts whose c-axes are aligned perpendicular to a surface on which the semiconductor layer is formed or the top surface of the semiconductor layer and in which the adjacent crystal parts have no grain boundary.

The use of such a material as the semiconductor layer makes it possible to achieve a highly reliable transistor in which a change in the electrical characteristics is reduced.

Charge accumulated in a capacitor through a transistor including the above-described semiconductor layer can be retained for a long time because of the low off-state current of the transistor. The use of such a transistor in pixels allows a driver circuit to stop while the gray level of an image displayed on each display region is maintained. As a result, an electronic device with significantly reduced power consumption can be achieved.

For stable characteristics of the transistor or the like, a base film is preferably provided. The base film can be formed to be a single layer or a stacked layer using an inorganic insulating film such as a silicon oxide film, a silicon nitride film, a silicon oxynitride film, or a silicon nitride oxide film. The base film can be formed by a sputtering method, a CVD (Chemical Vapor Deposition) method (e.g., a plasma CVD method, a thermal CVD method, or an MOCVD (Metal Organic CVD) method), an ALD (Atomic Layer Deposition) method, a coating method, a printing method, or the like. Note that the base film is not necessarily provided when not needed.

Note that an FET 623 is illustrated as a transistor formed in the driver circuit portion 601. The driver circuit can be formed using various circuits such as a CMOS circuit, a PMOS circuit, and an NMOS circuit. Although a driver-integrated type in which the driver circuit is formed over the substrate is described in this embodiment, the driver circuit is not necessarily formed over the substrate and can be formed outside.

The pixel portion 602 is formed with a plurality of pixels including a switching FET 611, a current control FET 612, and a first electrode 613 electrically connected to a drain of the current control FET 612; however, without being limited thereto, a pixel portion in which three or more FETs and a capacitor are combined may be employed.

Note that an insulator 614 is formed to cover an end portion of the first electrode 613. The insulator 614 can be formed using a positive photosensitive acrylic resin film here.

In order to improve the coverage with an EL layer or the like to be formed later, the insulator 614 is formed so as to have a curved surface with curvature at its upper end portion or lower end portion. For example, in the case where positive photosensitive acrylic is used as a material for the insulator 614, only the upper end portion of the insulator 614 preferably has a curved surface with a curvature radius (0.2 μm to 3 μm). In addition, as the material for the insulator 614, either a negative photosensitive resin or a positive photosensitive resin can be used.

An EL layer 616 and a second electrode 617 are formed over the first electrode 613. Here, as a material used for the first electrode 613 functioning as an anode, a material with a high work function is desirably used. For example, a single-layer film of an ITO film, an indium tin oxide film containing silicon, an indium oxide film containing zinc oxide at 2 wt % to 20 wt %, a titanium nitride film, a chromium film, a tungsten film, a Zn film, a Pt film, or the like, a stacked layer of titanium nitride film and a film containing aluminum as its main component, a three-layer structure of a titanium nitride film, a film containing aluminum as its main component, and a titanium nitride film, or the like can be used. Note that the stacked-layer structure achieves low wiring resistance, a favorable ohmic contact, and a function as an anode.

The EL layer 616 is formed by any of a variety of methods such as an evaporation method using an evaporation mask, an inkjet method, and a spin coating method. The EL layer 616 has the structure described in Embodiment 1. Alternatively, a material included in the EL layer 616 may be a low molecular compound or a high molecular compound (including an oligomer or a dendrimer).

As a material used for the second electrode 617, which is formed over the EL layer 616 and functions as a cathode, a material with a low work function (e.g., Al, Mg, Li, Ca, or an alloy or a compound thereof (MgAg, MgIn, AlLi, or the like)) is preferably used. Note that in the case where light generated in the EL layer 616 passes through the second electrode 617, it is preferable to use, for the second electrode 617, a stacked layer of a thin metal film and a transparent conductive film (e.g., ITO, indium oxide containing zinc oxide at 2 wt % to 20 wt %, indium tin oxide containing silicon, or zinc oxide (ZnO)).

Note that a light-emitting device is formed with the first electrode 613, the EL layer 616, and the second electrode 617. The light-emitting device is the light-emitting device described in Embodiment 2. A plurality of light-emitting devices are formed in the pixel portion, and the light-emitting apparatus of this embodiment may include both the light-emitting device described in Embodiment 2 and a light-emitting device having a different structure.

The sealing substrate 604 and the element substrate 610 are attached to each other using the sealant 605, so that a structure is employed in which a light-emitting device 618 is provided in the space 607 surrounded by the element substrate 610, the sealing substrate 604, and the sealant 605. The space 607 is filled with a filler; it is filled with an inert gas (e.g., nitrogen or argon) in some cases, and filled with the sealant in some cases. The sealing substrate in which a recessed portion is formed and a desiccant is provided is preferable because deterioration due to the influence of moisture can be inhibited.

Note that an epoxy-based resin or glass frit is preferably used for the sealant 605. Furthermore, these materials are preferably materials that transmit moisture or oxygen as little as possible. For the sealing substrate 604, in addition to a glass substrate and a quartz substrate, a plastic substrate formed of FRP (Fiber Reinforced Plastics), PVF (polyvinyl fluoride), polyester, acrylic, or the like can be used.

Although not illustrated in FIG. 2, a protective film may be provided over the second electrode. As the protective film, an organic resin film or an inorganic insulating film can be formed. The protective film may be formed so as to cover an exposed portion of the sealant 605. The protective film may be provided so as to cover surfaces and side surfaces of the pair of substrates and exposed side surfaces of a sealing layer, an insulating layer, and the like.

For the protective film, a material that is less likely transmit an impurity such as water. Thus, diffusion of an impurity such as water from the outside into the inside can be effectively inhibited.

As a material included in the protective film, an oxide, a nitride, a fluoride, a sulfide, a ternary compound, a metal, a polymer, or the like can be used; for example, it is possible to use a material containing aluminum oxide, hafnium oxide, hafnium silicate, lanthanum oxide, silicon oxide, strontium titanate, tantalum oxide, titanium oxide, zinc oxide, niobium oxide, zirconium oxide, tin oxide, yttrium oxide, cerium oxide, scandium oxide, erbium oxide, vanadium oxide, indium oxide; a material containing aluminum nitride, hafnium nitride, silicon nitride, tantalum nitride, titanium nitride, niobium nitride, molybdenum nitride, zirconium nitride, gallium nitride; a material containing a nitride containing titanium and aluminum, an oxide containing titanium and aluminum, an oxide containing aluminum and zinc, a sulfide containing manganese and zinc, a sulfide containing cerium and strontium, an oxide containing erbium and aluminum, an oxide containing yttrium and zirconium, or the like.

The protective film is preferably formed using a deposition method that enables favorable step coverage. One such method is an atomic layer deposition (ALD) method. A material that can be formed by an ALD method is preferably used for the protective film. With the use of an ALD method, a dense protective film with reduced defects such as cracks and pinholes or with a uniform thickness can be formed. Furthermore, damage caused to a process member in forming the protective film can be reduced.

By an ALD method, a uniform protective film with few defects can be formed even on a surface with a complex uneven shape or upper, side, and lower surfaces of a touch panel.

As described above, the light-emitting apparatus fabricated using the light-emitting device described in Embodiment 2 can be obtained.

The light-emitting apparatus in this embodiment uses the light-emitting device described in Embodiment 2 and thus has favorable characteristics. Specifically, since the light-emitting device described in Embodiment 2 is a light-emitting device having a long lifetime, the light-emitting apparatus can have favorable reliability. Furthermore, since the light-emitting apparatus using the light-emitting device described in Embodiment 2 has favorable emission efficiency, the light-emitting apparatus can achieve low power consumption.

FIG. 3 illustrates examples of a light-emitting apparatus in which full color display is achieved by formation of a light-emitting device exhibiting white light emission and provision of coloring layers (color filters) and the like. FIG. 3(A) illustrates a substrate 1001, a base insulating film 1002, a gate insulating film 1003, gate electrodes 1006, 1007, and 1008, a first interlayer insulating film 1020, a second interlayer insulating film 1021, a peripheral portion 1042, a pixel portion 1040, a driver circuit portion 1041, first electrodes 1024W, 1024R, 1024G, and 1024B of the light-emitting devices, a partition 1025, an EL layer 1028, a second electrode 1029 of the light-emitting devices, a sealing substrate 1031, a sealant 1032, and the like.

In FIG. 3(A), coloring layers (a red coloring layer 1034R, a green coloring layer 1034G, and a blue coloring layer 1034B) are provided on a transparent base material 1033. A black layer (black matrix) 1035 may be additionally provided. The transparent base material 1033 provided with the coloring layers and the black matrix is positioned and fixed to the substrate 1001. Note that the coloring layers and the black matrix 1035 are covered with an overcoat layer 1036. In FIG. 3(A), there is light extracted to the outside without passing through the coloring layers and light extracted to the outside after passing through the coloring layers of each color. The light that does not pass through the coloring layers is white, and the light that passes through the coloring layers is red, green, and blue, so that an image can be expressed with the pixels of four colors.

FIG. 3(B) illustrates an example in which the coloring layers (the red coloring layer 1034R, the green coloring layer 1034G, and the blue coloring layer 1034B) are formed between the gate insulating film 1003 and the first interlayer insulating film 1020. The coloring layers may be provided between the substrate 1001 and the sealing substrate 1031 in this manner.

Figure 4:
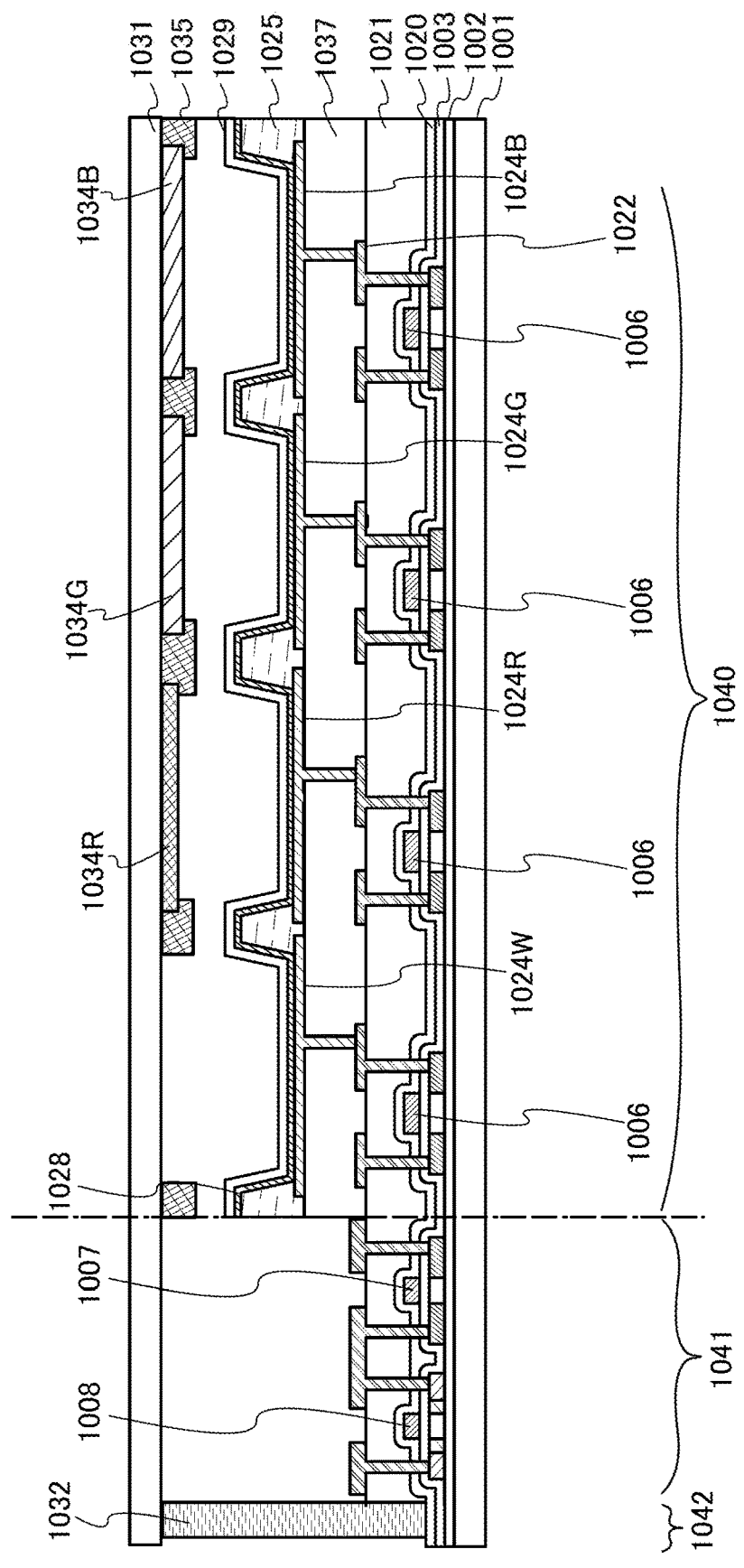
FIG. 4 is a conceptual view of an active matrix light-emitting apparatus.

The above-described light-emitting apparatus is a light-emitting apparatus having a structure in which light is extracted to the substrate 1001 side where the FETs are formed (a bottom-mission type), but may be a light-emitting apparatus having a structure in which light emission is extracted to the sealing substrate 1031 side (a top-emission type). FIG. 4 illustrates a cross-sectional view of a top-emission light-emitting apparatus. In this case, a substrate that does not transmit light can be used as the substrate 1001. The top-emission light-emitting apparatus is formed in a manner similar to that of the bottom-emission light-emitting apparatus until a connection electrode which connects the FET and the anode of the light-emitting device is formed. Then, a third interlayer insulating film 1037 is formed to cover an electrode 1022. This insulating film may have a planarization function. The third interlayer insulating film 1037 can be formed using a material similar to that for the second interlayer insulating film or using any other known materials.

The first electrodes 1024W, 1024R, 1024G, and 1024B of the light-emitting devices are each an anode here, but may each be a cathode. Furthermore, in the case of the top-emission light-emitting apparatus illustrated in FIG. 4, the first electrodes are preferably reflective electrodes. The EL layer 1028 is formed to have a device structure similar to the structure of the EL layer 103 described in Embodiment 1, with which white light emission can be obtained.

In the case of such a top-emission structure as in FIG. 4, sealing can be performed with the sealing substrate 1031 on which the coloring layers (the red coloring layer 1034R, the green coloring layer 1034G, and the blue coloring layer 1034B) are provided. The sealing substrate 1031 may be provided with the black matrix 1035 which is positioned between pixels. The coloring layers (the red coloring layer 1034R, the green coloring layer 1034G, and the blue coloring layer 1034B) and the black matrix may be covered with the overcoat layer 1036. Note that a light-transmitting substrate is used as the sealing substrate 1031. Although an example in which full color display is performed using four colors of red, green, blue, and white is shown here, there is no particular limitation and full color display may be performed using four colors of red, yellow, green, and blue or three colors of red, green, and blue.

In the top-emission light-emitting apparatus, a microcavity structure can be favorably employed. A light-emitting device with a microcavity structure can be obtained with the use of a reflective electrode as the first electrode and a semi-transmissive and semi-reflective electrode as the second electrode. The light-emitting device having a microcavity structure includes at least an EL layer between the reflective electrode and the semi-transmissive and semi-reflective electrode, and the EL layer includes at least a light-emitting layer functioning as a light-emitting region.

Note that the reflective electrode is a film having a visible light reflectivity of 40% to 100%, preferably 70% to 100%, and a resistivity of $1 \times 10^{-2}$ Ωcm or lower. In addition, the semi-transmissive and semi-reflective electrode is a film having a visible light reflectivity of 20% to 80%, preferably 40% to 70%, and a resistivity of $1 \times 10^{-2}$ Ωcm or lower.

Light emitted from the light-emitting layer included in the EL layer is reflected and resonated by the reflective electrode and the semi-transmissive and semi-reflective electrode.

In the light-emitting device, by changing thicknesses of the transparent conductive film, the above-described composite material, the carrier-transport material, and the like, the optical path length between the reflective electrode and the semi-transmissive and semi-reflective electrode can be changed. Thus, light with a wavelength that is resonated between the reflective electrode and the semi-transmissive and semi-reflective electrode can be intensified while light with a wavelength that is not resonated therebetween can be attenuated.

Note that light that is reflected back by the reflective electrode (first reflected light) considerably interferes with light that directly enters the semi-transmissive and semi-reflective electrode from the light-emitting layer (first incident light); therefore, the optical path length between the reflective electrode and the light-emitting layer is preferably adjusted to $(2n-1)\lambda/4$ (n is a natural number of 1 or larger and λ is a wavelength of light emission to be amplified). By adjusting the optical path length, the phases of the first reflected light and the first incident light can be aligned with each other and the light emitted from the light-emitting layer can be further amplified.

Note that in the above structure, the EL layer may include a plurality of light-emitting layers or may include a single light-emitting layer. In addition, the EL layer may be combined with the structure of the above-described tandem light-emitting device; for example, a plurality of EL layers each including a single or a plurality of light-emitting layer(s) may be provided in one light-emitting device with a charge generation layer sandwiched between the EL layers.

With the microcavity structure, emission intensity with a particular wavelength in the front direction can be increased, whereby power consumption can be reduced. Note that in the case of a light-emitting apparatus which displays images with subpixels of four colors of red, yellow, green, and blue, the light-emitting apparatus can have favorable characteristics because the luminance can be increased owing to yellow light emission and each subpixel can employ a microcavity structure suitable for wavelengths of the corresponding color.

The light-emitting apparatus in this embodiment uses the light-emitting device described in Embodiment 2 and thus has favorable characteristics. Specifically, since the light-emitting device described in Embodiment 2 is a light-emitting device having a long lifetime, the light-emitting apparatus can have favorable reliability. Furthermore, since the light-emitting apparatus using the light-emitting device described in Embodiment 2 has favorable emission efficiency, the light-emitting apparatus can achieve low power consumption.

Figure 5A:
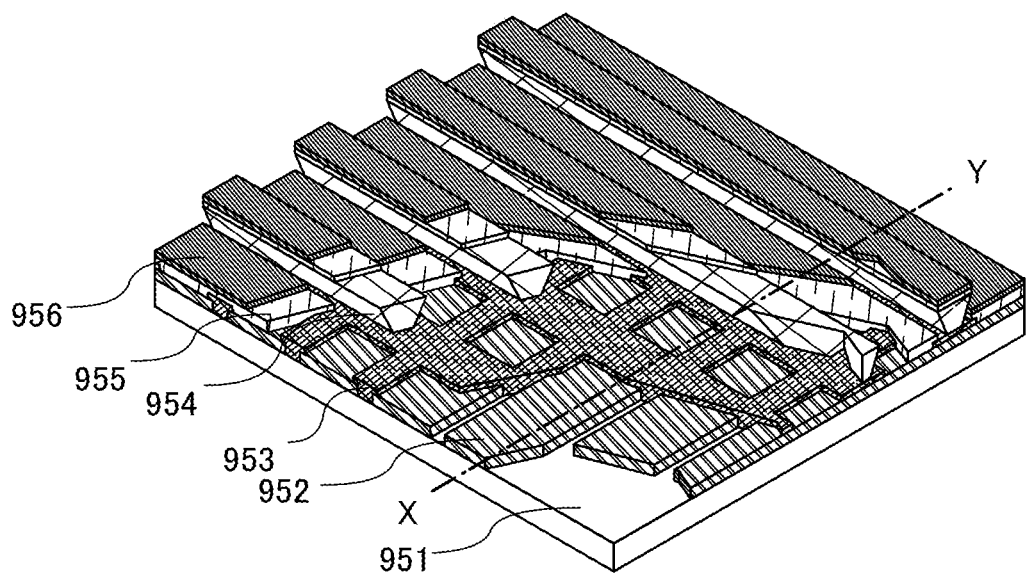
FIGS. 5A and 5B are conceptual views of a passive matrix light-emitting apparatus.
Figure 5B:
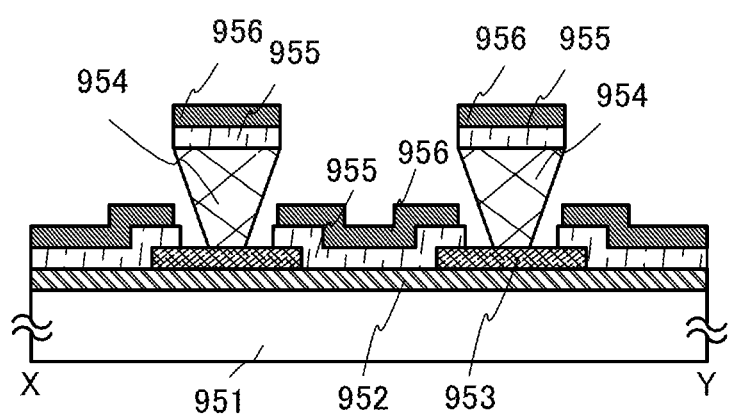

The active matrix light-emitting apparatus is described above, whereas a passive matrix light-emitting apparatus is described below. FIG. 5 illustrates a passive matrix light-emitting apparatus fabricated using the present invention. Note that FIG. 5(A) is a perspective view illustrating the light-emitting apparatus, and FIG. 5(B) is a cross-sectional view taken along the dashed-dotted line X-Y of FIG. 5(A). In FIG. 5, an EL layer 955 is provided between an electrode 952 and an electrode 956 over a substrate 951. An end portion of the electrode 952 is covered with an insulating layer 953. A partition layer 954 is provided over the insulating layer 953. Sidewalls of the partition layer 954 are aslope such that the distance between one sidewall and the other sidewall is gradually narrowed toward the surface of the substrate. That is, a cross section in the short side direction of the partition layer 954 is a trapezoidal shape, and the lower side (the side facing the same direction as the plane direction of the insulating layer 953 and touching the insulating layer 953) is shorter than the upper side (the side facing the same direction as the plane direction of the insulating layer 953, and not touching the insulating layer 953). Providing the partition layer 954 in this manner can prevent defects of the light-emitting device due to static charge or the like. The passive-matrix light-emitting apparatus also uses the light-emitting device described in Embodiment 2; thus, the light-emitting device can have favorable reliability or low power consumption.

Since many minute light-emitting devices arranged in a matrix can be controlled in the above-described light-emitting apparatus, the light-emitting apparatus can be suitably used as a display device for expressing images.

In addition, this embodiment can be freely combined with the other embodiments.

Embodiment 4

Figure 6A:
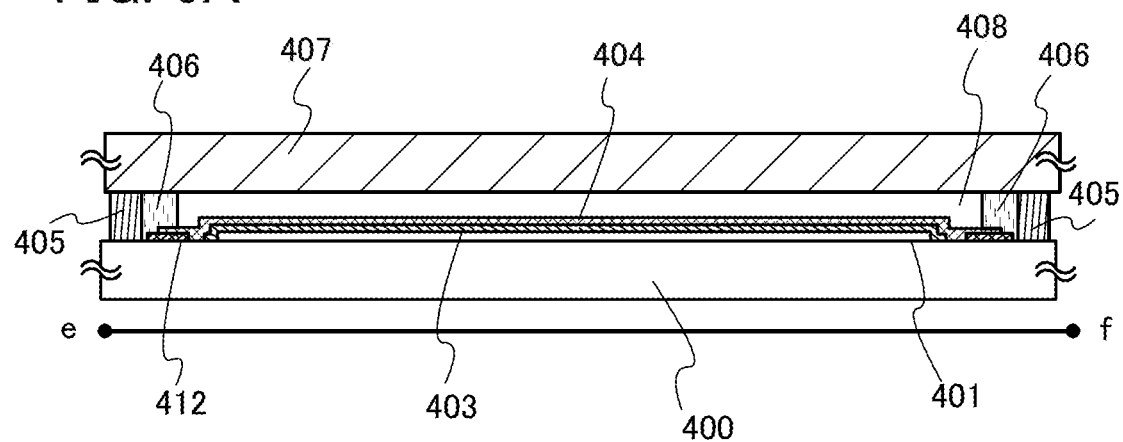
FIGS. 6A and 6B are drawings illustrating a lighting device.
Figure 6B:
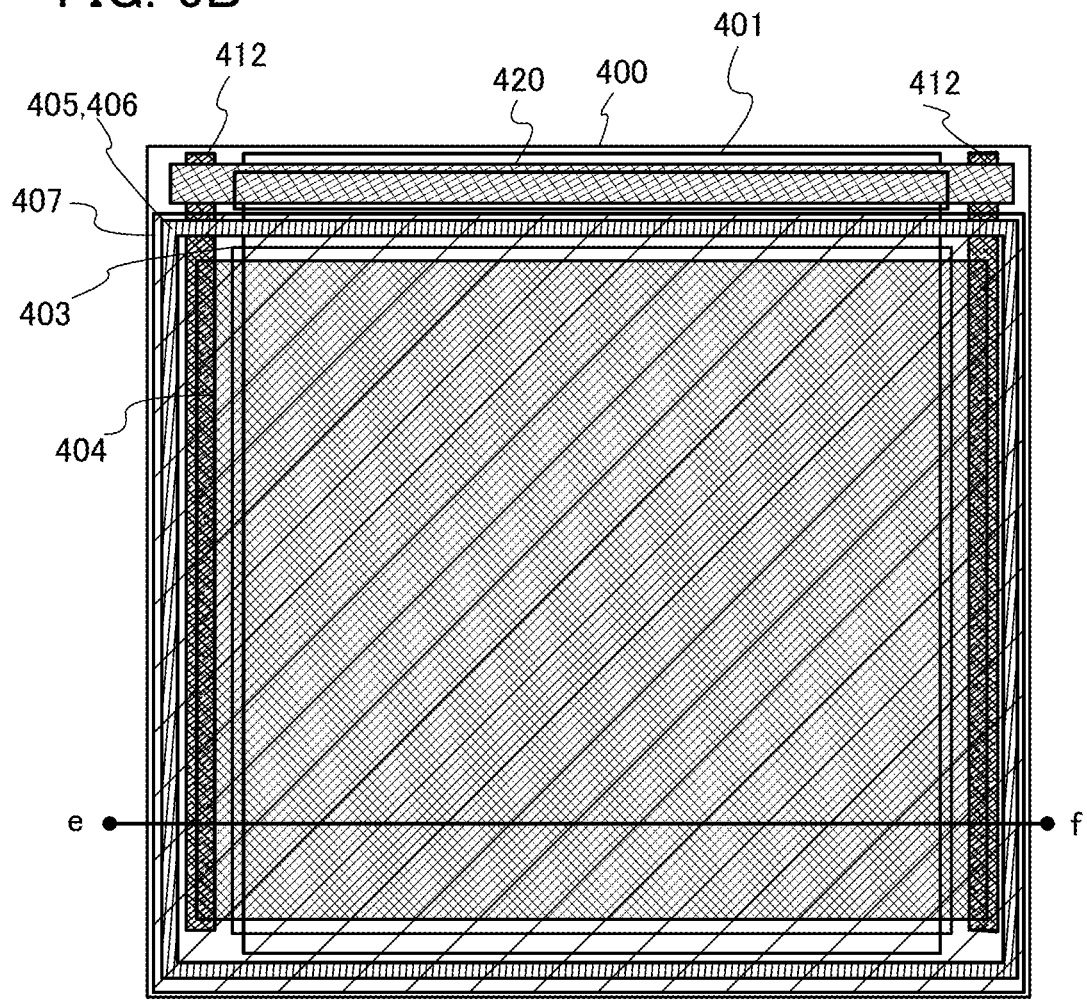

In this embodiment, an example in which the light-emitting device described in Embodiment 2 is used for a lighting device will be described with reference to FIG. 6. FIG. 6(B) is a top view of the lighting device, and FIG. 6(A) is a cross-sectional view taken along the line e-f in FIG. 6(B).

In the lighting device in this embodiment, a first electrode 401 is formed over a substrate 400 which is a support and has a light-transmitting property. The first electrode 401 corresponds to the first electrode 101 in Embodiment 1. In the case where light emission is extracted from the first electrode 401 side, the first electrode 401 is formed using a material having a light-transmitting property.

A pad 412 for supplying a voltage to a second electrode 404 is formed over the substrate 400.

An EL layer 403 is formed over the first electrode 401. The EL layer 403 has a structure corresponding to that of the EL layer 103 in Embodiment 1, or the structure in which the light-emitting units 511 and 512 are combined with the charge generation layer 513. Note that for these structures, the corresponding description can be referred to.

The second electrode 404 is formed to cover the EL layer 403. The second electrode 404 corresponds to the second electrode 102 in Embodiment 1. In the case where light-emission is extracted from the first electrode 401 side, the second electrode 404 is formed using a material having high reflectivity. The second electrode 404 is supplied with a voltage when connected to the pad 412.

As described above, the lighting device described in this embodiment includes a light-emitting device including the first electrode 401, the EL layer 403, and the second electrode 404. Since the light-emitting device is a light-emitting device with high emission efficiency, the lighting device in this embodiment can be a lighting device with low power consumption.

The substrate 400 over which the light-emitting device having the above structure is formed is fixed to a sealing substrate 407 with sealants 405 and 406 and sealing is performed, whereby the lighting device is completed. It is possible to use only either the sealant 405 or 406. In addition, the inner sealant 406 (not illustrated in FIG. 6(B)) can be mixed with a desiccant, which enables moisture to be adsorbed, resulting in improved reliability.

When parts of the pad 412 and the first electrode 401 are provided to extend to the outside of the sealants 405 and 406, those can serve as external input terminals. An IC chip 420 mounted with a converter or the like may be provided over the external input terminals.

The lighting device described in this embodiment uses the light-emitting device described in Embodiment 2 as an EL device; thus, the lighting device can have favorable reliability. Furthermore, the lighting device can have low power consumption.

Embodiment 5

In this embodiment, examples of electronic devices each partly including the light-emitting device described in Embodiment 2 are described. The light-emitting device described in Embodiment 2 is a light-emitting device having a favorable lifetime and favorable reliability. As a result, the electronic devices described in this embodiment can be electronic devices each including a light-emitting portion with favorable reliability.

Examples of electronic devices to which the light-emitting device is applied include a television devices (also referred to as TV or television receivers), monitors for computers and the like, cameras such as digital cameras and digital video cameras, digital photo frames, cellular phones (also referred to as portable telephones or portable telephone devices), portable game machines, portable information terminals, audio playback devices, and large game machines such as pin-ball machines. Specific examples of these electronic devices are shown below.

FIG. 7(A) illustrates an example of a television device. In the television device, a display portion 7103 is incorporated in a housing 7101. Here, a structure in which the housing 7101 is supported by a stand 7105 is shown. Images can be displayed on the display portion 7103, and the light-emitting devices described in Embodiment 2 are arranged in a matrix in the display portion 7103.

The television device can be operated with an operation switch of the housing 7101 or a separate remote controller 7110. With operation keys 7109 of the remote controller 7110, channels and volume can be operated and images displayed on the display portion 7103 can be operated. Furthermore, a structure may be employed in which the remote controller 7110 is provided with a display portion 7107 for displaying data output from the remote controller 7110.

Note that the television device has a structure of including a receiver, a modem, and the like. With the use of the receiver, a general television broadcast can be received, and moreover, when the television device is connected to a communication network with or without a wire via the modem, one-way (from a sender to a receiver) or two-way (between a sender and a receiver or between receivers) data communication can be performed.

FIG. 7(B1) is a computer which includes a main body 7201, a housing 7202, a display portion 7203, a keyboard 7204, an external connection port 7205, a pointing device 7206, and the like. Note that this computer is fabricated using the light-emitting devices described in Embodiment 2 arranged in a matrix in the display portion 7203. The computer in FIG. 7(B1) may be such a mode as illustrated in FIG. 7(B2). The computer in FIG. 7(B2) is provided with a second display portion 7210 instead of the keyboard 7204 and the pointing device 7206. The second display portion 7210 is of a touch-panel type, and input can be performed by operating display for input displayed on the second display portion 7210 with a finger or a dedicated pen. The second display portion 7210 can also display images other than the display for input. The display portion 7203 may also be a touch panel. Connecting the two screens with a hinge can prevent troubles such as a crack in or damage to the screens caused when the computer is stored or carried.

FIG. 7(C) illustrates an example of a portable terminal. A mobile phone includes operation buttons 7403, an external connection port 7404, a speaker 7405, a microphone 7406, and the like in addition to a display portion 7402 incorporated in a housing 7401. Note that the mobile phone includes the display portion 7402 which is fabricated by arranging the light-emitting devices described in Embodiment 2 in a matrix.

The portable terminal illustrated in FIG. 7(C) may have a structure in which information can be input by touching the display portion 7402 with a finger or the like. In this case, operations such as making a call and creating an e-mail can be performed by touching the display portion 7402 with a finger or the like.

The display portion 7402 has mainly three screen modes. The first one is a display mode mainly for displaying images, and the second one is an input mode mainly for inputting data such as text. The third one is a display+input mode in which two modes of the display mode and the input mode are combined.

For example, in the case of making a call or creating an e-mail, a text input mode mainly for inputting text is selected for the display portion 7402 so that an operation of inputting text displayed on the screen may be performed. In this case, it is preferable to display a keyboard or number buttons on almost the entire screen of the display portion 7402.

When a sensing device including a sensor for sensing inclination, such as a gyroscope sensor or an acceleration sensor, is provided inside the portable terminal, screen display of the display portion 7402 can be automatically changed by determining the orientation of the portable terminal (vertically or horizontally).

The screen modes are changed by touching the display portion 7402 or operating the operation buttons 7403 of the housing 7401. Alternatively, the screen modes can be changed depending on the kind of image displayed on the display portion 7402. For example, when a signal of an image displayed on the display portion is moving image data, the screen mode is changed to the display mode, and when the signal is text data, the screen mode is changed to the input mode.

Moreover, in the input mode, when input by the touch operation of the display portion 7402 is not performed for a certain period while a signal sensed by an optical sensor in the display portion 7402 is sensed, the screen mode may be controlled so as to be changed from the input mode to the display mode.

The display portion 7402 can also function as an image sensor. For example, an image of a palm print, a fingerprint, or the like is taken when the display portion 7402 is touched with the palm or the finger, whereby personal authentication can be performed. Furthermore, by using a backlight which emits near-infrared light or a sensing light source which emits near-infrared light in the display portion, an image of a finger vein, a palm vein, or the like can be taken.

Note that the structures described in this embodiment can be combined with any of the structures described Embodiment 1 to Embodiment 4 as appropriate.

As described above, the application range of the light-emitting apparatus including the light-emitting device described in Embodiment 2 is wide so that this light-emitting apparatus can be applied to electronic devices in a variety of fields. With the use of the light-emitting device described in Embodiment 2, an electronic device with high reliability can be obtained.

Figure 8A:
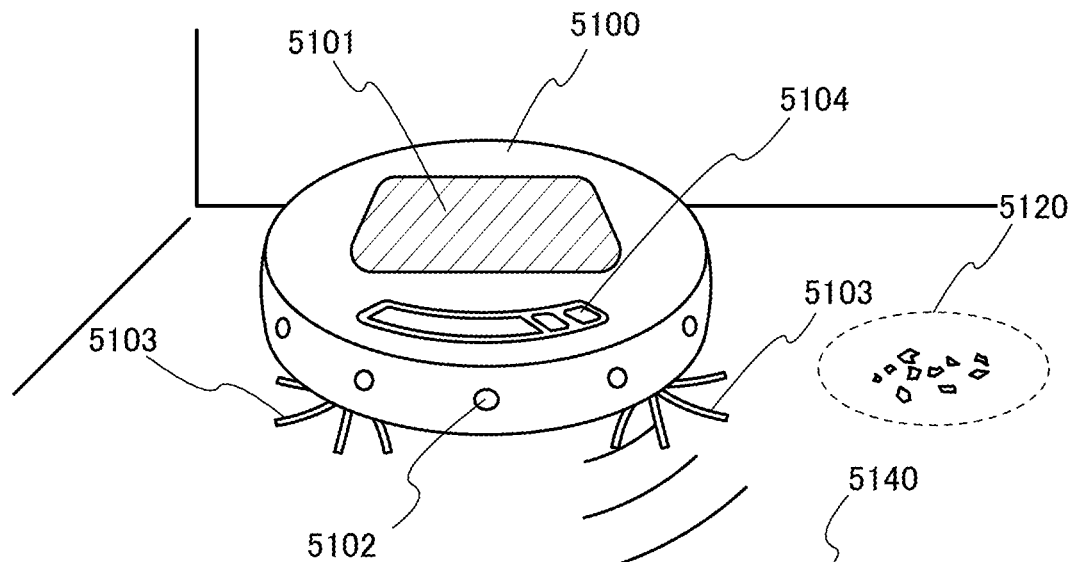
FIGS. 8A-8C are drawings illustrating electronic devices.

FIG. 8(A) is a schematic view illustrating an example of a cleaning robot.

A cleaning robot 5100 includes a display 5101 placed on its top surface, a plurality of cameras 5102 placed on its side surface, a brush 5103, and operation buttons 5104. Although not illustrated, the bottom surface of the cleaning robot 5100 is provided with a tire, an inlet, and the like. Furthermore, the cleaning robot 5100 includes various sensors such as an infrared sensor, an ultrasonic sensor, an acceleration sensor, a piezoelectric sensor, an optical sensor, and a gyroscope sensor. In addition, the cleaning robot 5100 has a wireless communication means.

The cleaning robot 5100 is self-propelled, detects dust 5120, and sucks up the dust through the inlet provided on the bottom surface.

The cleaning robot 5100 can judge whether there is an obstacle such as a wall, furniture, or a step by analyzing images taken by the cameras 5102. When an object that is likely to be caught in the brush 5103, such as a wire, is detected by image analysis, the rotation of the brush 5103 can be stopped.

The display 5101 can display the remaining capacity of a battery, the amount of vacuumed dust, and the like. The display 5101 may display a path on which the cleaning robot 5100 has run. The display 5101 may be a touch panel, and the operation buttons 5104 may be provided on the display 5101.

The cleaning robot 5100 can communicate with a portable electronic device 5140 such as a smartphone. The portable electronic device 5140 can display images taken by the cameras 5102. Accordingly, an owner of the cleaning robot 5100 can monitor the room even from the outside. The display on the display 5101 can be checked by the portable electronic device such as a smartphone.

The light-emitting apparatus of one embodiment of the present invention can be used for the display 5101.

Figure 8B:
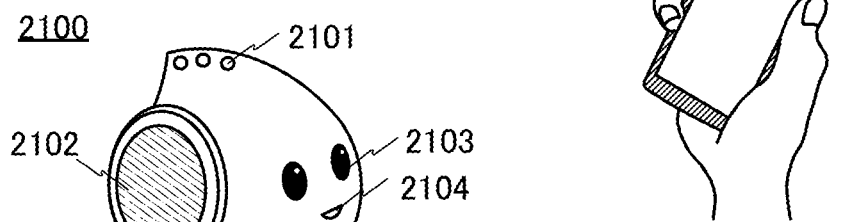

A robot 2100 illustrated in FIG. 8(B) includes an arithmetic device 2110, an illuminance sensor 2101, a microphone 2102, an upper camera 2103, a speaker 2104, a display 2105, a lower camera 2106, an obstacle sensor 2107, and a moving mechanism 2108.

The microphone 2102 has a function of detecting a speaking voice of a user, an environmental sound, and the like. The speaker 2104 also has a function of outputting sound. The robot 2100 can communicate with a user using the microphone 2102 and the speaker 2104.

The display 2105 has a function of displaying various kinds of information. The robot 2100 can display information desired by a user on the display 2105. The display 2105 may be provided with a touch panel. Moreover, the display 2105 may be a detachable information terminal, in which case charging and data communication can be performed when the display 2105 is set at the home position of the robot 2100.

The upper camera 2103 and the lower camera 2106 each have a function of taking an image of the surroundings of the robot 2100. The obstacle sensor 2107 can detect the presence of an obstacle in the direction where the robot 2100 advances with the moving mechanism 2108. The robot 2100 can move safely by recognizing the surroundings with the upper camera 2103, the lower camera 2106, and the obstacle sensor 2107. The light-emitting apparatus of one embodiment of the present invention can be used for the display 2105.

Figure 8C:
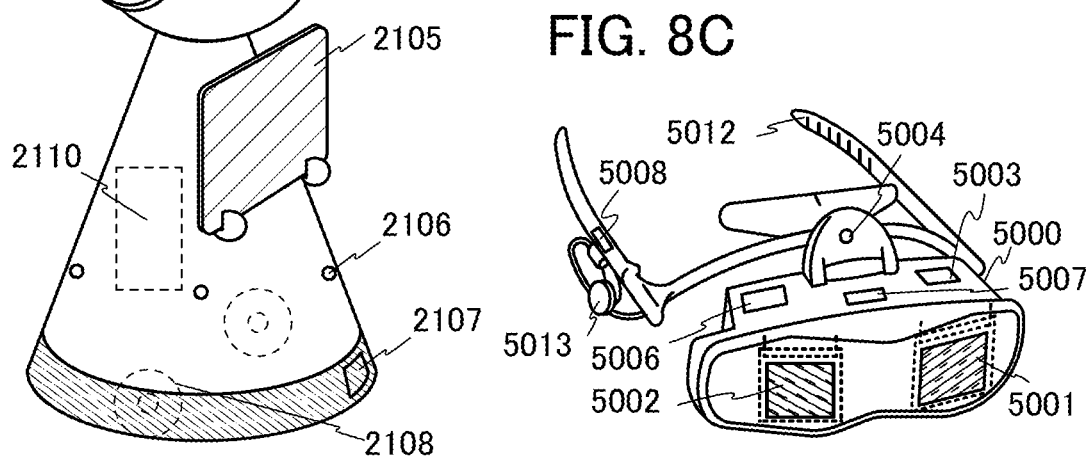

FIG. 8(C) shows an example of a goggle-type display. The goggle-type display includes, for example, a housing 5000, a display portion 5001, a speaker 5003, an LED lamp 5004, a connection terminal 5006, a sensor 5007 (a sensor having a function of measuring force, displacement, position, speed, acceleration, angular velocity, rotational frequency, distance, light, liquid, magnetism, temperature, chemical substance, sound, time, hardness, electric field, current, voltage, power, radiation, flow rate, humidity, gradient, oscillation, odor, or infrared ray), a microphone 5008, a display portion 5002, a support 5012, and an earphone 5013.

The light-emitting apparatus of one embodiment of the present invention can be used for the display portion 5001 and the second display portion 5002.

Figure 9:
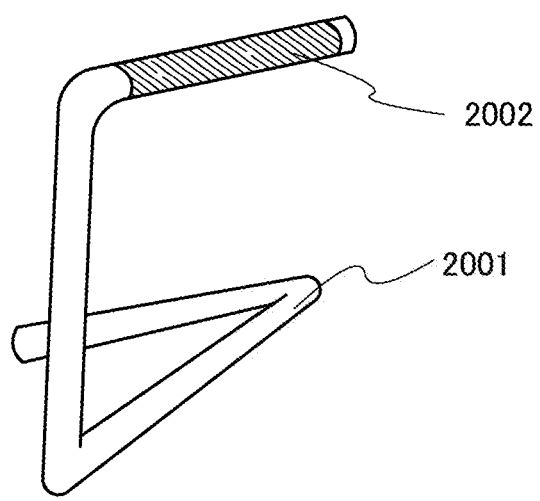
FIG. 9 is a drawing illustrating a lighting device.

FIG. 9 illustrates an example in which the light-emitting device described in Embodiment 2 is used for a table lamp which is a lighting device. The table lamp illustrated in FIG. 9 includes a housing 2001 and a light source 2002, and the lighting device described in Embodiment 4 may be used for the light source 2002.

Figure 10:
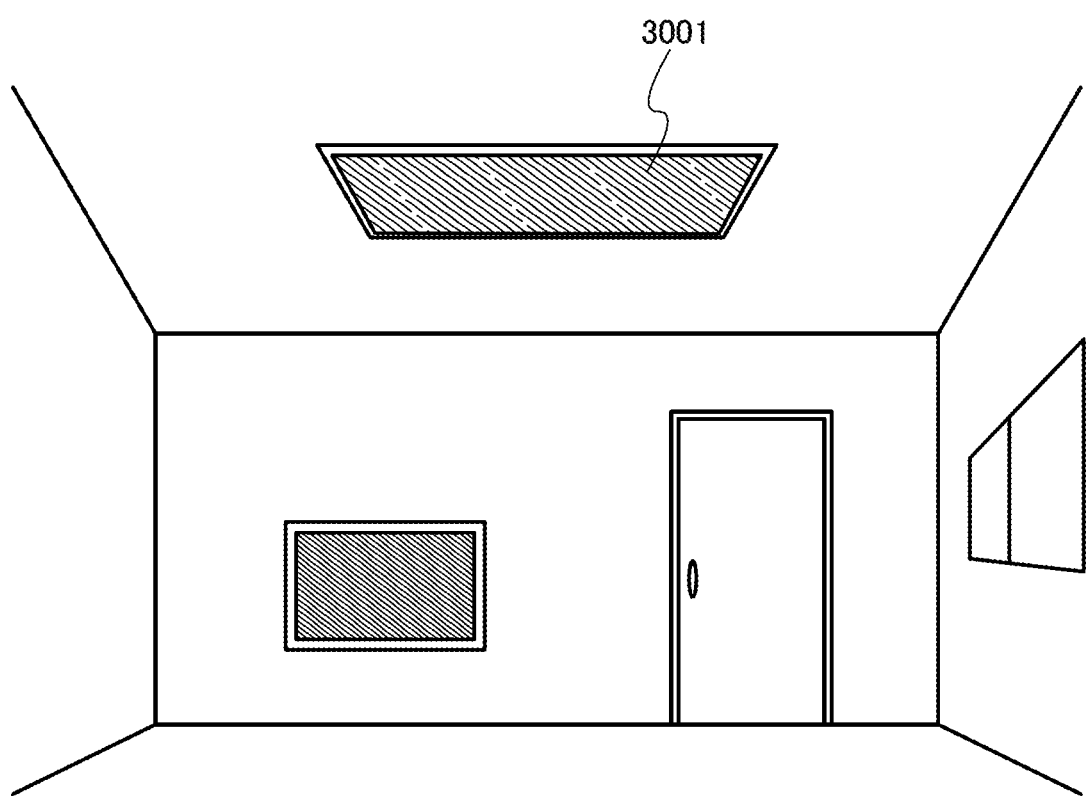
FIG. 10 is a drawing illustrating a lighting device.

FIG. 10 illustrates an example in which the light-emitting device described in Embodiment 2 is used for an indoor lighting device 3001. Since the light-emitting device described in Embodiment 2 is a light-emitting device having high reliability, the lighting device can have high reliability. Furthermore, the light-emitting device described in Embodiment 2 can have a larger area, and thus can be used for a large-area lighting device. Furthermore, the light-emitting device described in Embodiment 2 is thin, and thus can be used for a lighting device having a reduced thickness.

Figure 11:
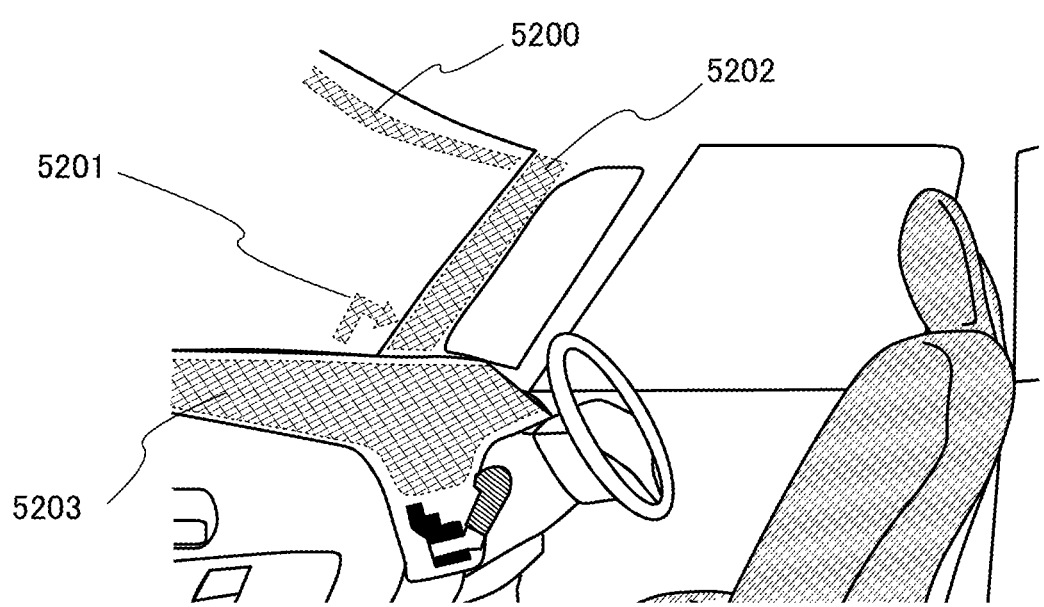
FIG. 11 is a drawing illustrating in-vehicle display devices and lighting devices.

The light-emitting device described in Embodiment 2 can also be used for a windshield or a dashboard of an automobile. FIG. 11 illustrates one mode in which the light-emitting device described in Embodiment 2 is used for a windshield and a dashboard of an automobile. The light-emitting devices described in Embodiment 2 are used for each of a display region 5200 to a display region 5203.

The display region 5200 and the display region 5201 are display apparatuses into which the light-emitting devices described in Embodiment 2 are incorporated. When the light-emitting devices described in Embodiment 2 are fabricated using electrodes having light-transmitting properties as a first electrode and a second electrode, what is called see-through display devices, through which the opposite side can be seen, can be obtained. See-through display can be provided even in the automobile windshield without hindering the vision. Note that in the case where a driving transistor or the like is provided, it is preferable to use a transistor having a light-transmitting property, such as an organic transistor using an organic semiconductor material or a transistor using an oxide semiconductor.

The display region 5202 is a display device provided in a pillar portion into which the light-emitting device described in Embodiment 2 is incorporated. The display region 5202 can compensate for the view hindered by the pillar by displaying an image taken by an imaging means provided on the outside of the automobile. Similarly, the display region 5203 provided in the dashboard portion can compensate for the view hindered by the car body by displaying an image taken by an imaging means provided on the outside of the automobile, which can enhance the safety. Showing an image so as to compensate for the area that cannot be seen makes it possible to confirm safety more naturally and comfortably.

The display region 5203 can provide a variety of kinds of information by displaying navigation data, a speedometer, a tachometer, a mileage, a fuel meter, a gearshift state, air-condition setting, and the like. The content or layout of the display can be changed freely in accordance with the preference of a user. Note that such information can also be displayed on the display region 5200 to the display region 5202. The display region 5200 to the display region 5203 can also be used as lighting devices.

Figure 12A:
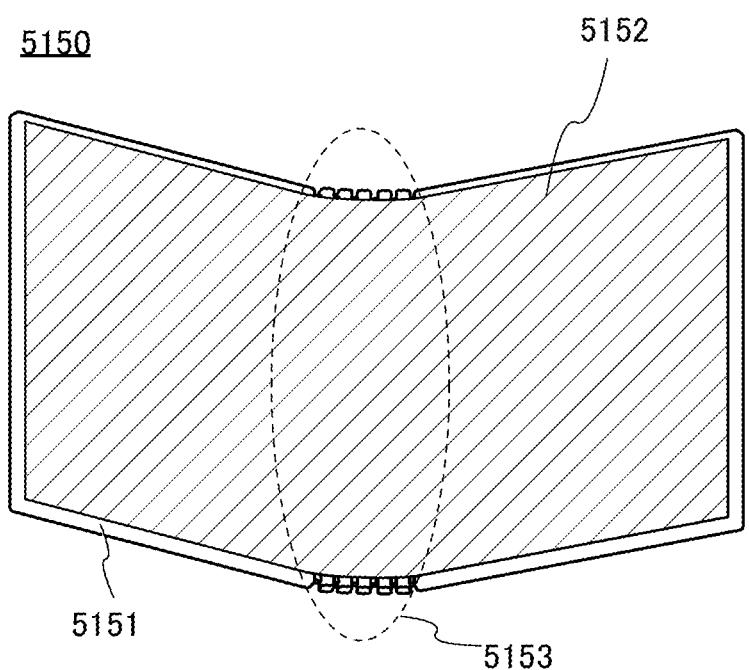
FIGS. 12A and 12B are drawings illustrating an electronic device.
Figure 12B:
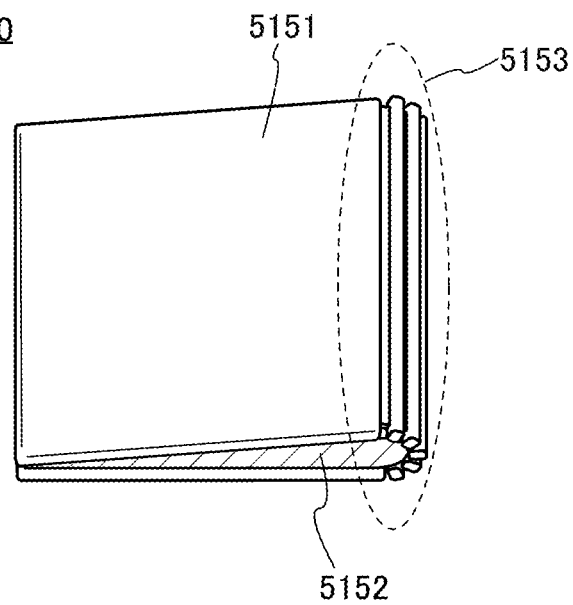

FIGS. 12(A) and 12(B) illustrate a foldable portable information terminal 5150. The foldable portable information terminal 5150 includes a housing 5151, a display region 5152, and a bend portion 5153. FIG. 12(A) illustrates the portable information terminal 5150 that is opened. FIG. 12(B) illustrates the portable information terminal 5150 that is folded. The portable information terminal 5150 is compact in size and has excellent portability when folded, despite its large display region 5152.

The display region 5152 can be folded in half with the bend portion 5153. The bend portion 5153 is formed of a stretchable member and a plurality of supporting members. When the display region is folded, the stretchable member stretches and the bend portion 5153 has a curvature radius of 2 mm or more, preferably 3 mm or more.

Note that the display region 5152 may be a touch panel (an input/output device) including a touch sensor (an input device). The light-emitting apparatus of one embodiment of the present invention can be used for the display region 5152.

Figure 13A:
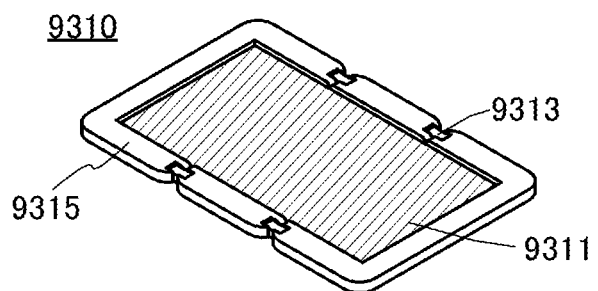
FIGS. 13A-13C are drawings illustrating an electronic device.
Figure 13B:
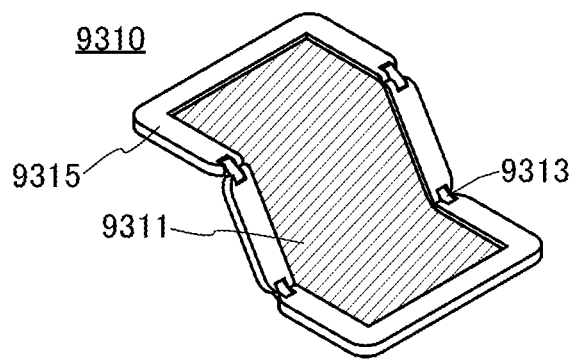
Figure 13C:
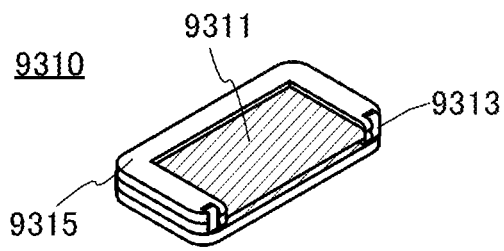

FIGS. 13(A) to 13(C) illustrate a foldable portable information terminal 9310. FIG. 13(A) illustrates the portable information terminal 9310 that is opened. FIG. 13(B) illustrates the portable information terminal 9310 which is in the state of being changed from one of an opened state and a folded state to the other. FIG. 13(C) illustrates the portable information terminal 9310 that is folded. The portable information terminal 9310 is excellent in portability when folded, and is excellent in display browsability when opened because of a seamless large display region.

A display panel 9311 is supported by three housings 9315 joined together by hinges 9313. Note that the display panel 9311 may be a touch panel (an input/output device) including a touch sensor (an input device). By folding the display panel 9311 at the hinges 9313 between two housings 9315, the portable information terminal 9310 can be reversibly changed in shape from the opened state to the folded state. The light-emitting apparatus of one embodiment of the present invention can be used for the display panel 9311. In the folded portable information terminal 9310, the display region positioned at a side surface of the display panel 9311 can display information icons, shortcuts of frequently used applications or programs, and the like, and confirmation of information and start of an application can be smoothly performed.

EXAMPLE 1

Synthesis Example 1

In this synthesis example, a synthesis method of 7-phenyl-5-[4-(10-phenyl-9-anthryl)phenyl]dibenzo[c,g]carbazole (abbreviation: PCgDBCPA), which is the organic compound of one embodiment of the present invention, will be described in detail. The structural formula of PcgDBCPA is shown below.

[Chemical Formula 27]

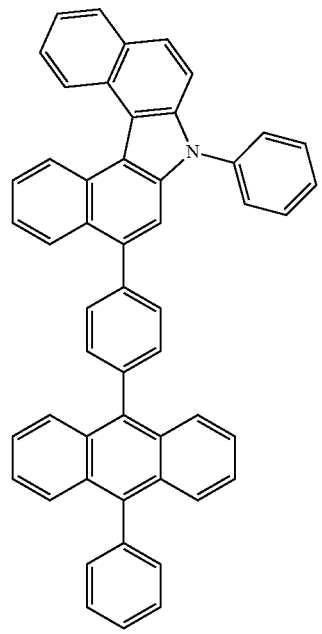

In a 200-mL three-neck flask were put 2.3 g (5.5 mmol) of 5-bromo-7-phenyldibenzo[c,g]carbazole, 2.5 g (6.7 mmol) of 4-(10-phenyl-9-anthryl)phenylboronic acid, 0.63 g (1.5 mmol) of S-phos, 2.9 g (14 mmol) of tripotassium phosphate, and 55 mL of toluene. This mixture was degassed by being stirred under reduced pressure, and the air in the flask was replaced with nitrogen. To this mixture was added 0.33 g (0.57 mmol) of bis(dibenzylideneacetone)palladium (0), the mixture was stirred at 80° C. under a nitrogen stream for seven hours, stirred at 100° C. for 13 hours, and then refluxed at 130° C. for 23 hours. After the reflux, a precipitated solid was separated by suction filtration. The obtained filtrate was separated into an aqueous layer and an organic layer, the aqueous layer was subjected to extraction with toluene, and the extracted solution was added to the organic layer. The organic layer was washed with a saturated aqueous solution of sodium hydrogen carbonate and saturated saline solution, and dried with magnesium sulfate. This mixture was subjected to gravity filtration and the filtrate was concentrated, whereby a solid was obtained. The obtained solid was purified twice by silica gel column chromatography (toluene:hexane=1:3), washed with methanol, and then recrystallized with toluene, whereby 2.5 g of a pale yellow powder, which was the target substance, was obtained in a yield of 68%. The synthesis scheme is shown below.

[Chemical Formula 28]

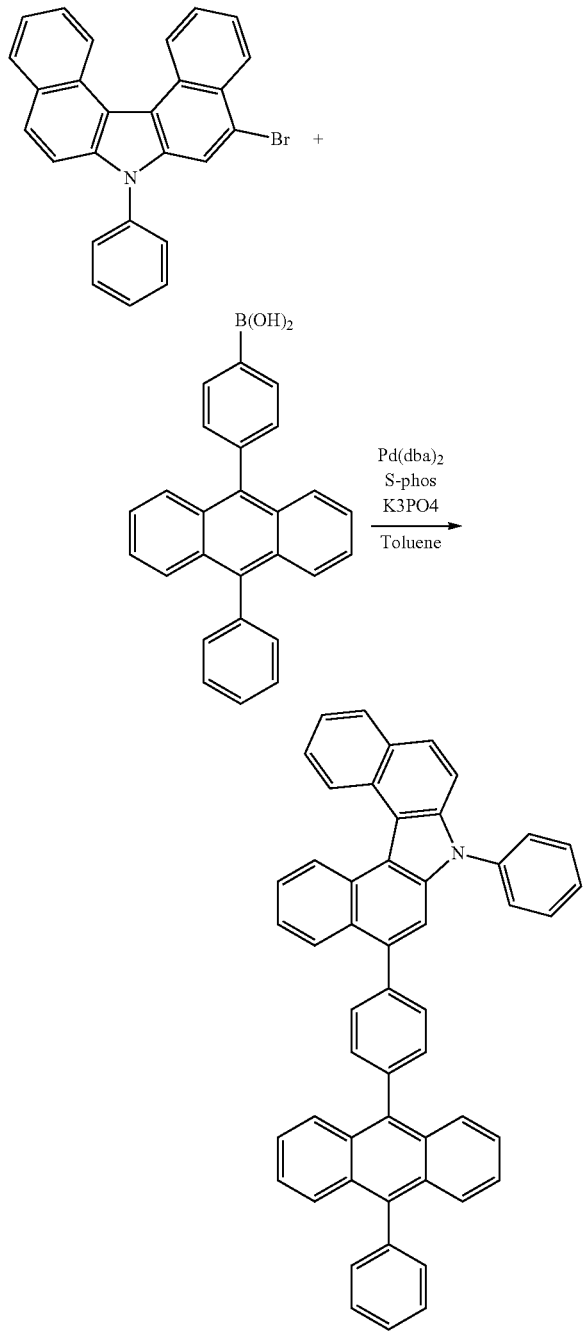

By the train sublimation method, 2.5 g of the obtained pale yellow powder was purified by sublimation. The sublimation purification was performed by heating at 340° C. under the conditions where the pressure was 2.8 Pa and the argon flow rate was 15 mL/min. After the sublimation purification, 2.2 g of the pale yellow powder was obtained at a collection rate of 87%.

Figure 14A:
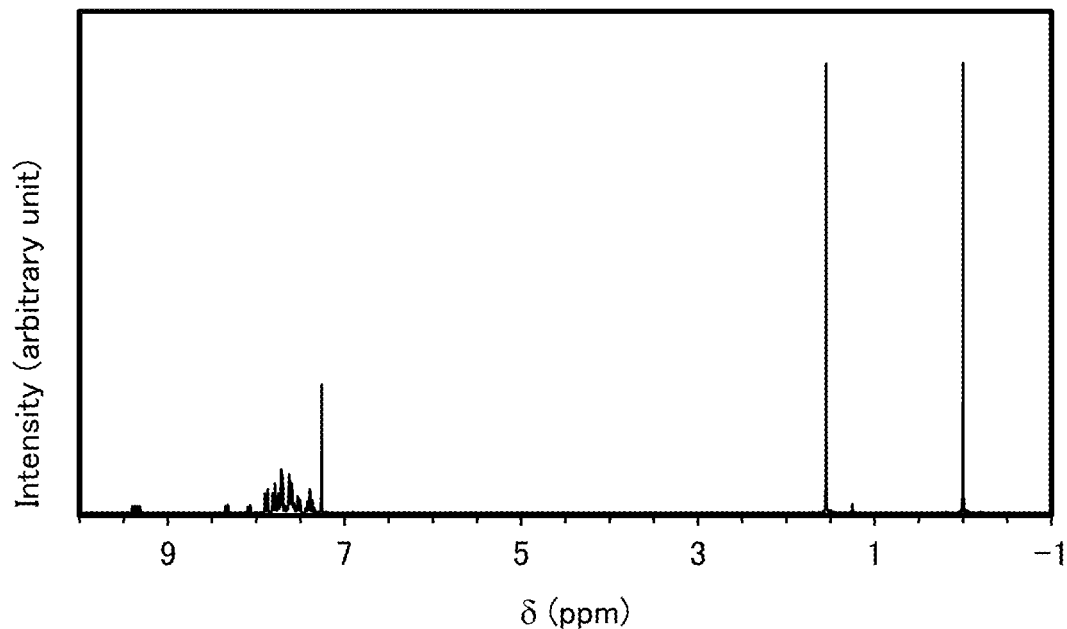
FIGS. 14A and 14B are $^1$H NMR spectra of PcgDBCPA.
Figure 14B:
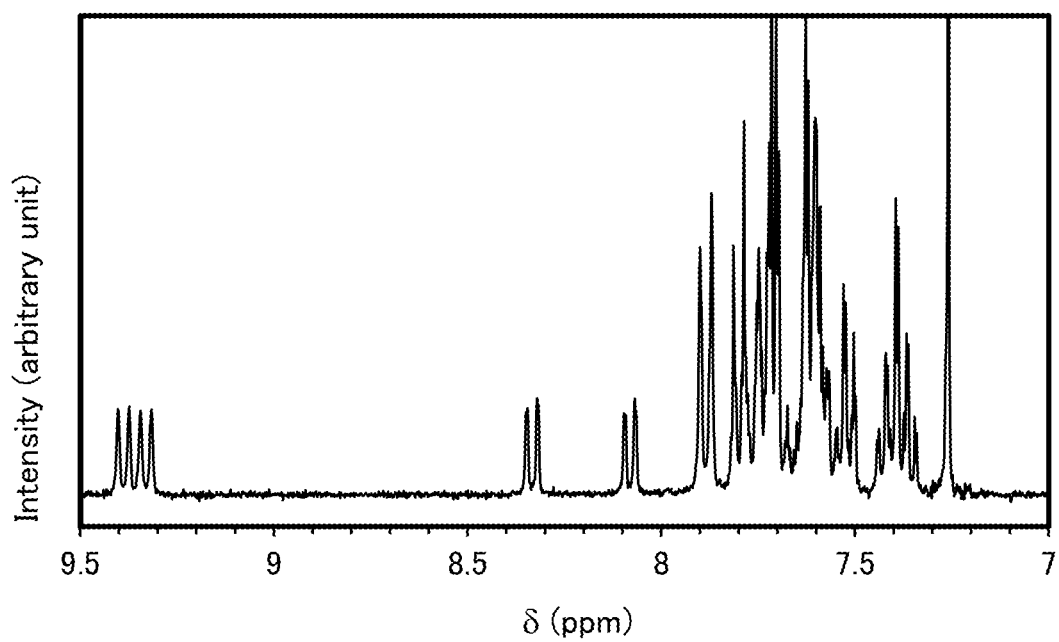

FIG. 14 shows $^1$H NMR charts of the obtained compound, and numerical data is shown below. The results show that PcgDBCPA, which is the dibenzo[c,g]carbazole derivative of one embodiment of the present invention, was obtained in this synthesis example.

$^1$H NMR (CDCl$_3$, 300 MHz): δ=7.34-7.7.44 (m, 4H), 7.50-7.90 (m, 25H), 8.08 (d, J=8.4 Hz, 1H), 8.33 (d, J=7.5 Hz, 1H), 9.33 (d, J=8.4 Hz, 1H), 9.39 (d, J=8.7 Hz, 1H).

Figure 15A:
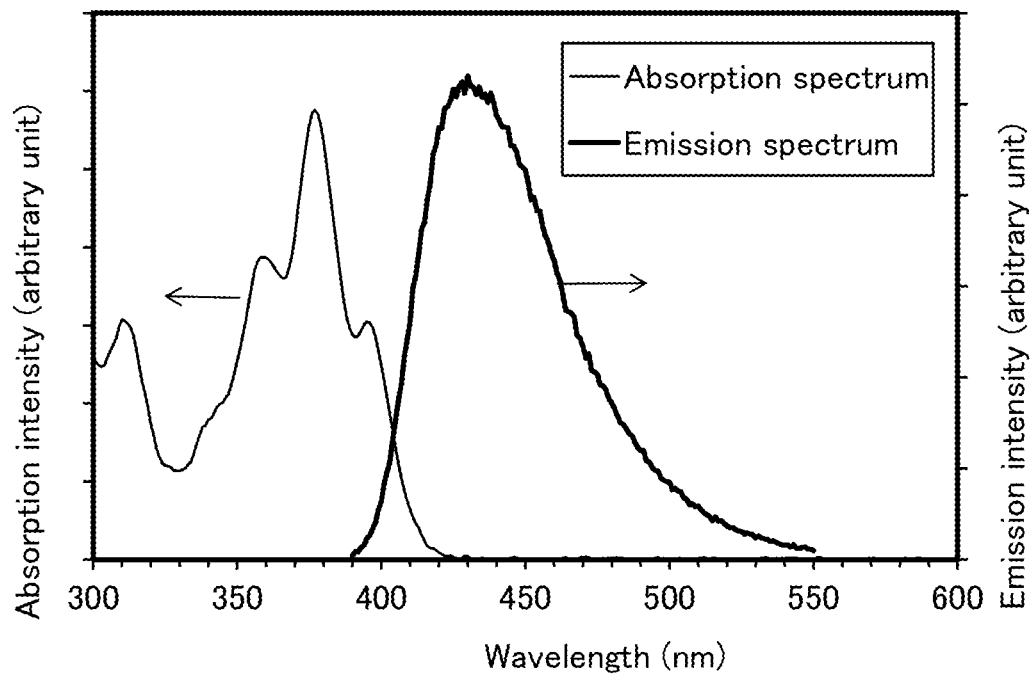
FIGS. 15A and 15B are absorption spectra and emission spectra of PcgDBCPA.
Figure 15B:
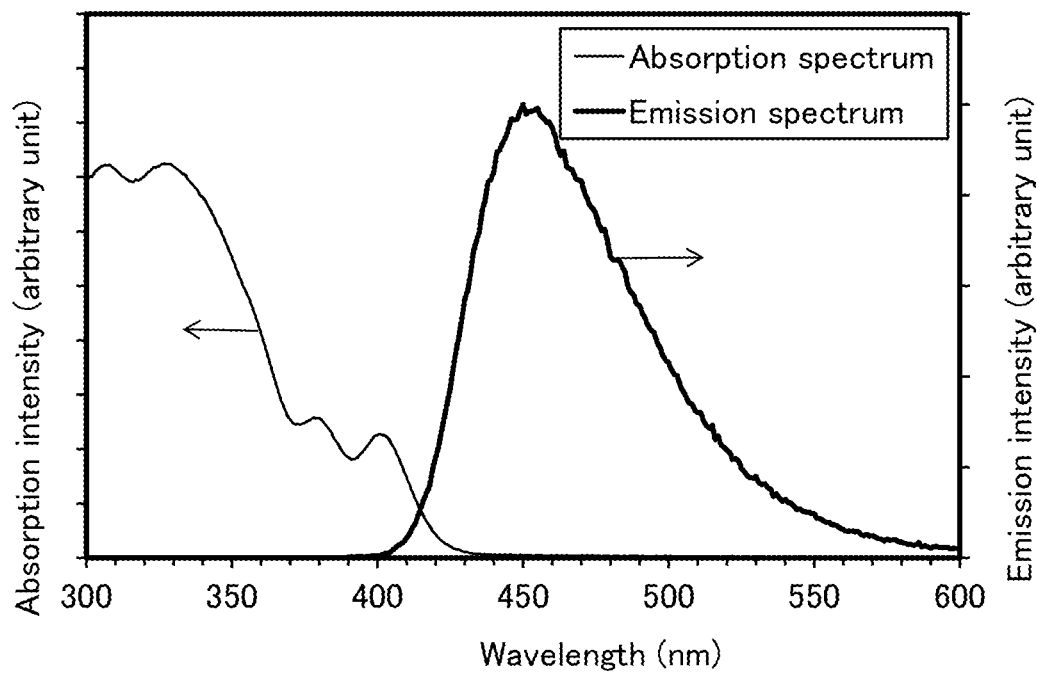

FIG. 15(A) shows an absorption spectrum and an emission spectrum of PcgDBCPA in a toluene solution. In addition, FIG. 15(B) shows an absorption spectrum and an emission spectrum of a thin film. The solid thin film was fabricated over a quartz substrate by a vacuum evaporation method. The absorption spectrum in the solution was measured using an ultraviolet-visible light spectrophotometer (V550, manufactured by JASCO Corporation), and the absorption spectrum of PcgDBCPA in the solution shown in FIG. 15(A) was obtained by subtracting the absorption spectrum of toluene measured when only toluene was put in a quartz cell from the absorption spectrum of PcgDBCPA in the toluene solution. In addition, the absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.).

As shown in FIG. 15(A), in the case of PcgDBCPA in the toluene solution, absorption peaks were observed at around 399 nm, 377 nm, 359 nm, and 310 nm, and an emission wavelength peak was observed at around 430 nm (excitation wavelength: 378 nm). Furthermore, as shown in FIG. 15(B), in the case of the thin film of PcgDBCPA, the absorption peaks were observed at around 403 nm, 379 nm, 361 nm, and 314 nm, and the emission wavelength peak was observed at around 453 nm (excitation wavelength: 380 nm). In addition, PcgDBCPA was confirmed to emit blue light. The above results show that the compound of one embodiment of the present invention can be used as a host for a light-emitting substance or a substance that exhibits fluorescence in the visible region.

Furthermore, the thin film of PcgDBCPA was found to have a good film quality with little change in shape, hardly being aggregated even under air.

The HOMO level and the LUMO level of PcgDBCPA were calculated on the basis of a cyclic voltammetry (CV) measurement. The calculation method is shown below.

An electrochemical analyzer (model number: ALS model 600A or 600C, manufactured by BAS Inc.) was used as a measurement apparatus. To prepare a solution for the CV measurement, dehydrated dimethylformamide (DMF) (produced by Sigma-Aldrich Inc., 99.8%, catalog No. 22705-6) was used as a solvent, tetra-n-butylammonium perchlorate (n-Bu$_4$NClO$_4$) (produced by Tokyo Chemical Industry Co., Ltd., catalog No. T0836) as a supporting electrolyte was dissolved at a concentration of 100 mmol/L, and the object to be measured was also dissolved at a concentration of 2 mmol/L. A platinum electrode (PTE platinum electrode, manufactured by BAS Inc.) was used as a working electrode, another platinum electrode (Pt counter electrode for VC-3 (5 cm), manufactured by BAS Inc.) was used as an auxiliary electrode, and an Ag/Ag$^+$ electrode (RE7 reference electrode for non-aqueous solvent, manufactured by BAS Inc.) was used as a reference electrode. Note that the measurement was performed at room temperature (20° C. to 25° C.). In addition, the scan speed in the CV measurement was fixed to 0.1 V/sec, and an oxidation potential Ea [V] and a reduction potential Ec [V] with respect to the reference electrode were measured. Ea is an intermediate potential of an oxidation-reduction wave, and Ec is an intermediate potential of a reduction-oxidation wave. Here, since the potential energy of the reference electrode used in this example with respect to the vacuum level is known to be −4.94 [eV], the HOMO level and the LUMO level can be calculated by the following formulae: HOMO level [eV]=− 4.94−Ea and LUMO level [eV]=−4.94−Ec.

Furthermore, CV measurement was repeated 100 times, and the oxidation-reduction wave in the hundredth cycle was compared with the oxidation-reduction wave in the first cycle to examine the electrical stability of the compound.

As a result, the HOMO level was found to be −5.67 eV in the measurement of the oxidation potential Ea[V] of PcgDBCPA. In contrast, the LUMO level was found to be −2.71 eV in the measurement of the reduction potential Ec[V].

EXAMPLE 2

Synthesis Example 2

In this synthesis example, a synthesis method of 7-phenyl-5-[4-(9-phenanthryl)phenyl]dibenzo[c,g]carbazole (abbreviation: PcgDBCPPn), which is the organic compound of one embodiment of the present invention, will be described in detail. The structural formula of PcgDBCPPn is shown below.

[Chemical Formula 29]

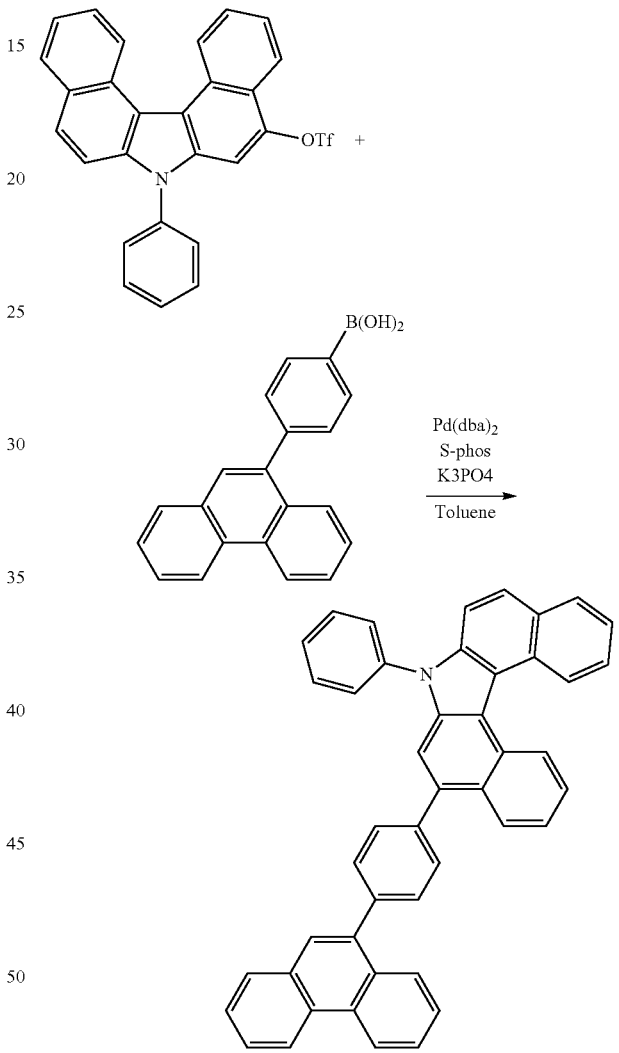

To a 100-mL three-neck flask were added 2.0 g (4.0 mmol) of trifluoromethane sulfonate (7-phenyldibenzo[c,g]carbazole-5-yl), 1.5 g (4.9 mmol) of 4-(9-phenanthryl)phenylboronic acid, 0.65 g (1.6 mmol) of S-phos, 1.9 g (9.0 mmol) of tripotassium phosphate, and 40 mL of toluene. This mixture was degassed by being stirred under reduced pressure, and the air in the flask was replaced with nitrogen. To this mixture was added 0.38 g (0.66 mmol) of bis(dibenzylideneacetone)palladium(0), the mixture was stirred at 80° C. under a nitrogen stream for 21 hours, and then stirred at 120° C. for 56 hours. After the stirring, water was added to the obtained mixture to separate an aqueous layer and an organic layer, and the aqueous layer was subjected to extraction with toluene. The obtained extracted solution and the organic layer were combined, washed with saturated saline solution, and dried with magnesium sulfate. The obtained mixture was subjected to gravity filtration and the filtrate was concentrated, whereby a solid was obtained. The obtained solid was purified twice by silica gel column chromatography (toluene:hexane=1:3), whereby a solid was obtained. The obtained solid was recrystallized with toluene, whereby 1.1 g of a pale yellow powder, which was the target substance, was obtained in a yield of 47%. The synthesis scheme is shown below.

[Chemical Formula 30]

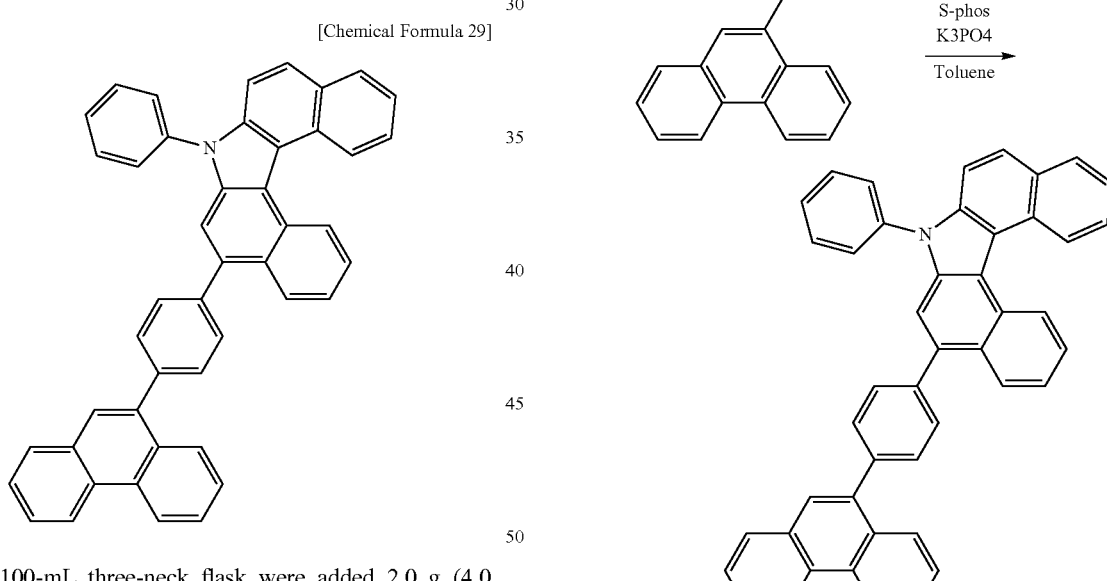

By the train sublimation method, 1.1 g of the obtained pale yellow powder was purified by sublimation. The sublimation purification was performed by heating at 300° C. under the conditions where the pressure was 3.1 Pa and the argon flow rate was 5.0 mL/min. After the sublimation purification, 1.0 g of the pale yellow powder was obtained at a collection rate of 95%.

Figure 16A:
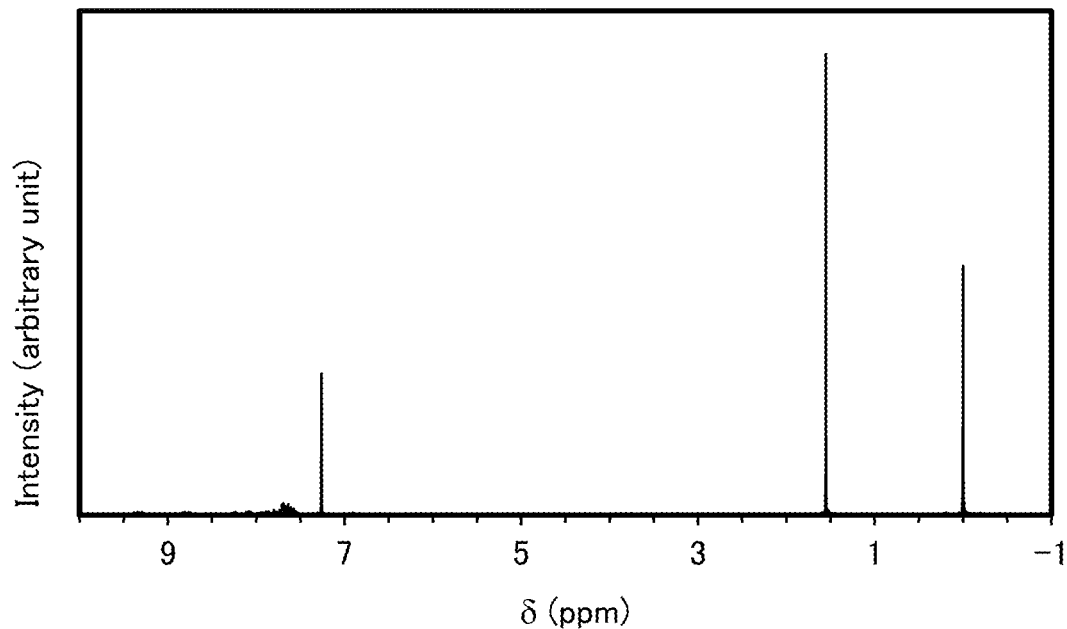
FIGS. 16A and 16B are $^1$H NMR spectra of PcgDBCPPn.
Figure 16B:
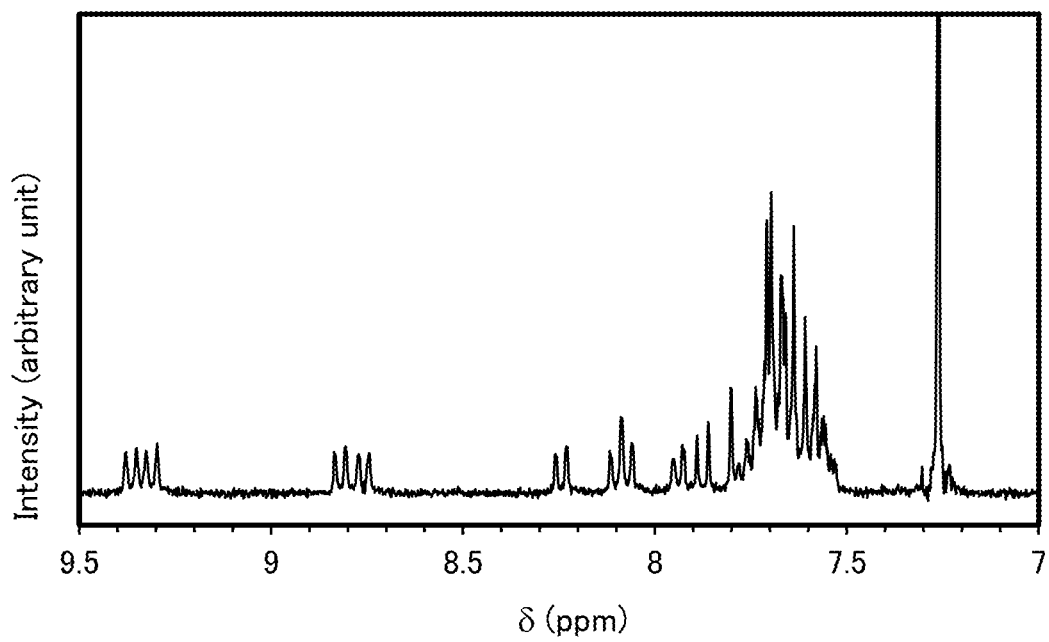

FIG. 16 shows $^1$H NMR charts of the obtained compound, and numerical data is shown below. The results show that PcgDBCPPn, which is the dibenzo[c,g]carbazole derivative of one embodiment of the present invention, was obtained in this synthesis example.

$^1$H NMR (CDCl$_3$, 300 MHz): δ=7.53-7.80 (m, 20H), 7.88 (d, J=9.0 Hz, 1H), 7.94 (d, J=7.2 Hz, 1H), 8.09 (t, J=8.4 Hz, 2H), 8.25 (d, J=8.4 Hz, 1H), 8.76 (d, J=8.4 Hz, 1H), 8.82 (d, J=8.7 Hz, 1H), 9.31 (d, J=8.7 Hz, 1H), 9.36 (d, J=8.4 Hz, 1H).

Figure 17A:
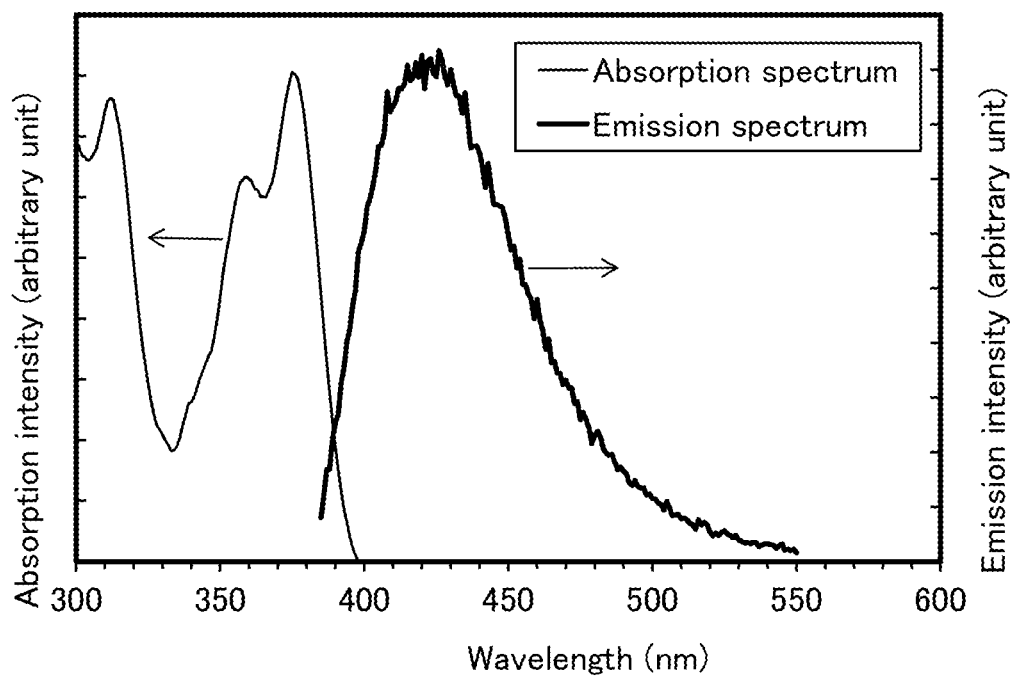
FIGS. 17A and 17B are absorption spectra and emission spectra of PcgDBCPPn.
Figure 17B:
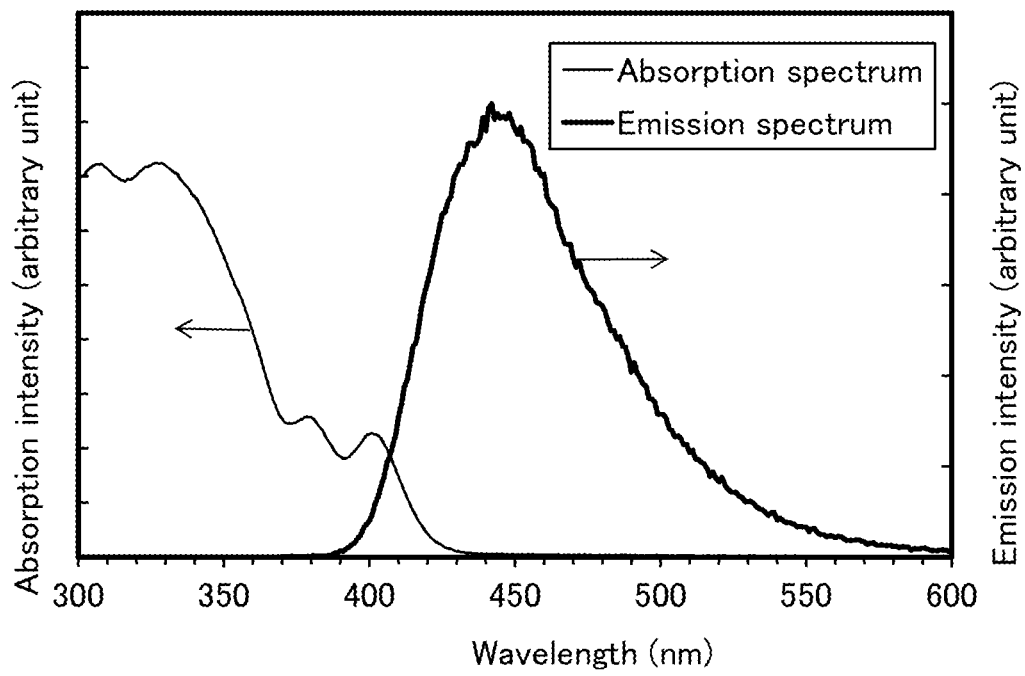

FIG. 17(A) shows an absorption spectrum and an emission spectrum of PcgDBCPPn in a toluene solution. In addition, FIG. 17(B) shows an absorption spectrum and an emission spectrum of a thin film. The solid thin film was fabricated over a quartz substrate by a vacuum evaporation method. The absorption spectrum in the solution was measured using an ultraviolet-visible light spectrophotometer (V550, manufactured by JASCO Corporation), and the absorption spectrum of PcgDBCPPn in the solution shown in FIG. 17(A) was obtained by subtracting the absorption spectrum of toluene measured when only toluene was put in a quartz cell from the absorption spectrum of PcgDBCPPn in the toluene solution. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.).

As shown in FIG. 17, in the case of PcgDBCPPn in the toluene solution, absorption peaks were observed at around 375 nm, 359 nm, and 312 nm, and an emission wavelength peak was observed at around 426 nm (excitation wavelength: 376 nm). Furthermore, as shown in FIG. 17, in the case of the thin film of PcgDBCPPn, the absorption peaks were observed at around 380 nm, 365 nm, and 315 nm, and the emission wavelength peak was observed at around 445 nm (excitation wavelength: 365 nm). PcgDBCPPn was confirmed to emit blue light. The compound of one embodiment of the present invention can be used as a host for a light-emitting substance or a substance that exhibits fluorescence in the visible region.

Furthermore, the thin film of PcgDBCPPn was found to have a good film quality with little change in shape, hardly being aggregated even under air.

The HOMO level and the LUMO level of PcgDBCPPn were calculated on the basis of a cyclic voltammetry (CV) measurement. Since the calculation method is similar to the method described in Example 1, the description thereof is omitted. Example 1 should be referred to.

As a result, the HOMO level was found to be −5.67 eV in the measurement of the oxidation potential Ea[V] of PcgDBCPPn. In contrast, the LUMO level was found to be −2.43 eV in the measurement of the reduction potential Ec[V]. In addition, when the oxidation-reduction wave was repeatedly measured and the waveform of the first cycle was compared with that of the hundredth cycle, 86% of the peak intensity was maintained in the Ea measurement, and 96% of the peak intensity was maintained in the Ec measurement, which confirmed that PcgDBCPPn had extremely high resistance to oxidation and reduction.

EXAMPLE 3

In this example, a light-emitting device 1 and a light-emitting device 2, which are one embodiment of the present invention described in Embodiment 2, and a comparative light-emitting device 1 will be described. The structural formulae of organic compounds used in the light-emitting device 1, the light-emitting device 2, and the comparative light-emitting device 1 are shown below.

[Chemical Formula 31]

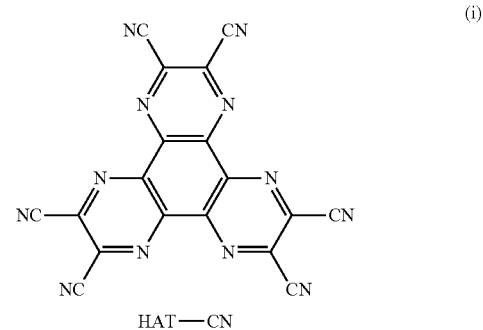

HAT—CN

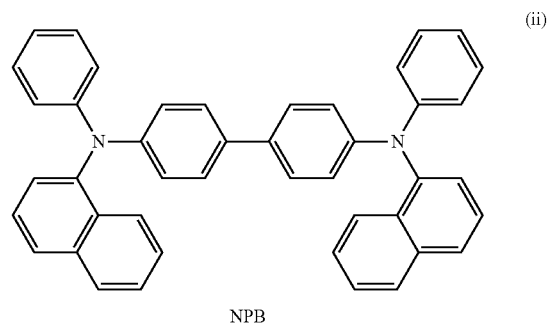

NPB

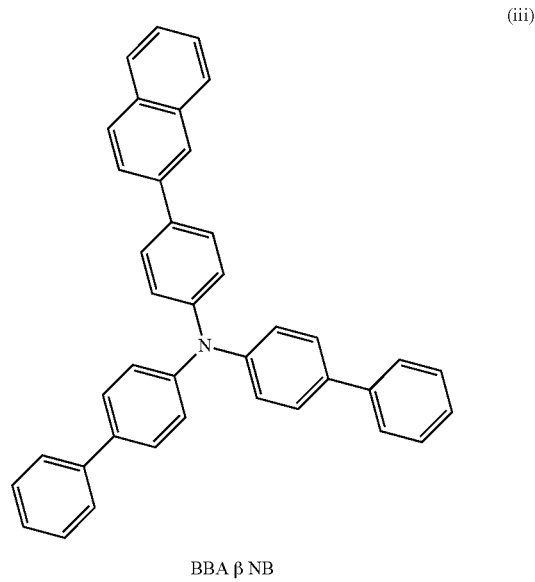

BBAβNB

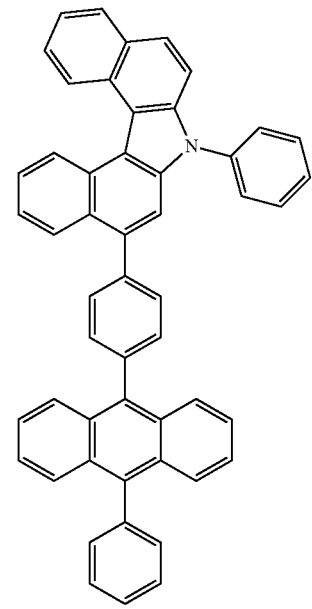
PcgDBCPA
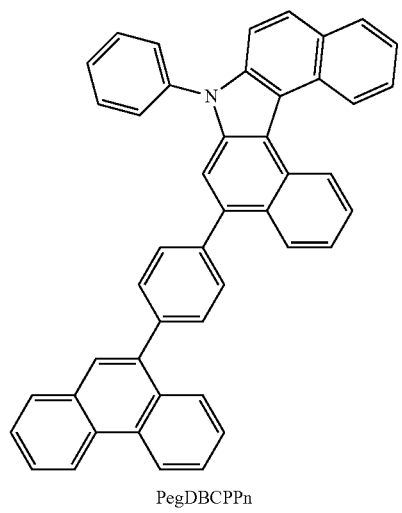
PegDBCPPn
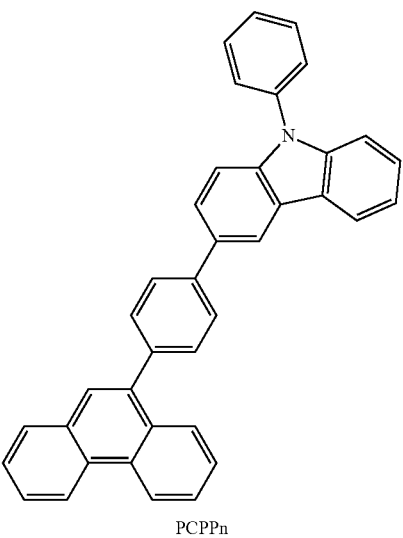
PCPPn
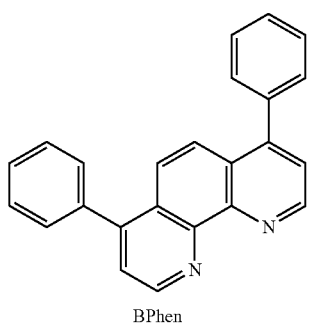
BPhen
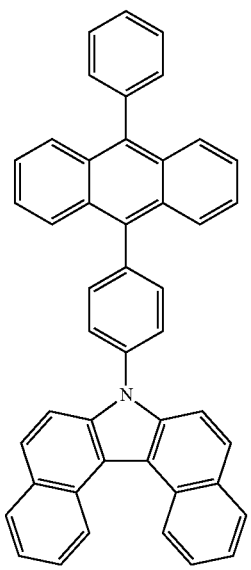
cgDBCzPA -continued (viii)

1,6mMemFLPAPm (Fabricating Method of Light-Emitting Device 1)

First, a film of indium tin oxide containing silicon oxide (ITSO) was formed over a glass substrate by a sputtering method, so that the first electrode 101 was formed. Note that the thickness was 70 nm and the electrode area was 2 mm×2 mm.

Next, in pretreatment for forming the light-emitting device over the substrate, the substrate surface was washed with water and baked at 200° C. for one hour, and then subjected to UV ozone treatment for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Then, the substrate over which the first electrode 101 was formed was fixed to a substrate holder provided in the vacuum evaporation apparatus so that the surface over which the first electrode 101 was formed faced downward, and over the first electrode 101, 2,3,6,7,10,11-hexacyano-1,4,5,8,9,12-hexaazatriphenylene (abbreviation: HAT-CN) represented by the above structural formula (i) was evaporated to a thickness of 5 nm by an evaporation method using resistance heating, so that the hole-injection layer 111 was formed.

Next, 4,4'-bis[N-(1-naphthyl)-N-phenylamino]biphenyl (abbreviation: NPB) represented by the above structural formula (ii) was evaporated to a thickness of 10 nm over the hole-injection layer 111 to form the first hole-transport layer 112-1; 4-(2-naphthyl)-4',4''-diphenyltriphenylamine (abbreviation: BBAβNB) represented by the above structural formula (iii) was evaporated to a thickness of 10 nm over the first hole-transport layer 112-1 to form the second hole-transport layer 112-2; and 7-phenyl-5-[4-(10-phenyl-9-anthryl)phenyl]dibenzo[c,g]carbazole (abbreviation: PcgDBCPA) represented by the above structural formula (iv) was evaporated to a thickness of 10 nm over the second hole-transport layer 112-2 to form the third hole-transport layer 112-3.

Next, 7-[4-(10-phenyl-9-anthryl)phenyl]-7H-dibenzo[c,g]carbazol e (abbreviation: cgDBCzPA) represented by the above structural formula (vii) and N,N'-bis(3-methylphenyl)-N,N'-bis[3-(9-phenyl-9H-fluoren-9-yl)phenyl]-pylene-1,6-diamine (abbreviation: 1,6mMemFLPAPrn) represented by the above structural formula (viii) were co-evaporated to a thickness of 25 nm to have a weight ratio of 1:0.03 (=cgDBCzPA: 1,6mMemFLPAPrn), whereby the light-emitting layer 113 was formed.

After that, over the light-emitting layer 113, cgDBCzPA was evaporated to a thickness of 10 nm, and bathophenanthroline (abbreviation: BPhen) represented by the above structural formula (ix) was evaporated to a thickness of 15 nm, whereby the electron-transport layer 114 was formed.

After the formation of the electron-transport layer 114, lithium fluoride (LiF) was evaporated to a thickness of 1 nm to form the electron-injection layer 115, and aluminum was evaporated to a thickness of 200 nm to form the second electrode 102, whereby the light-emitting device 1 of this example was fabricated.

(Fabricating Method of Light-Emitting Device 2)

The light-emitting device 2 was fabricated in a manner similar to that of the light-emitting device 1 except that PcgDBCPA used in the third hole-transport layer 112-3 of the light-emitting device 1 was replaced with 7-phenyl-5-[4-(9-phenanthryl)phenyl]dibenzo[c,g]carbazole (abbreviation: PcgDBCPPn) represented by the above structural formula (v).

(Fabricating Method of Comparative Light-Emitting Device 1)

The comparative light-emitting device 1 was fabricated in a manner similar to that of the light-emitting device 1 except that PcgDBCPA used in the third hole-transport layer 112-3 of the light-emitting device 1 was replaced with 3-[4-(9-phenanthryl)-phenyl]-9-phenyl-9H-carbazole (abbreviation: PCPPn).

The device structures of the light-emitting device 1, the light-emitting device 2, and the comparative light-emitting device 1 are listed in the following table.

TABLE 1

| | Hole injection layer | Hole-transport layer | | | Light-emitting layer | Electron-transport layer | | Electron-injection layer |
|---|---|---|---|---|---|---|---|---|
| | | 1 | 2 | 3 | | | | |
| | 5 nm | 10 nm | 10 nm | 10 nm | 25 nm | 10 nm | 15 nm | 1 nm |
| Light-emitting device 1 | HAT-CN | NPB | BBAβNB | *1 | cgDBCzPA: 1,6mMeinFLPAPrn (1:0.03) | cgDBCzPA | BPhen | LiF |
| Light-emitting device 2 | | | | | | | | |

TABLE 1-continued

|  | Hole injection layer | Hole-transport layer | | | Light-emitting layer | Electron-transport layer | | Electron-injection layer |
| --- | --- | --- | --- | --- | --- | --- | --- | --- |
|  |  | 1 | 2 | 3 |  | | | |
|  | 5 nm | 10 nm | 10 nm | 10 nm | 25 nm | 10 nm | 15 nm | 1 nm |
| Comparative light-emitting device 1 | | | | | | | | |

*1 Light-emitting device 1: PcgDBCPA. Light-emitting device 2: PcgDBCPA. Comparative light-emitting device 1: PCPPn Each of the light-emitting device 1, the light-emitting device 2, and the comparative light-emitting device 1 was subjected to sealing with a glass substrate (a sealant was applied to surround the device, followed by UV treatment and one-hour heat treatment at 80° C. at the time of sealing) in a glove box containing a nitrogen atmosphere so that the light-emitting device is not exposed to the air, and then the initial characteristics and reliabilities of these light-emitting devices were measured. Note that the measurement was carried out at room temperature.

Figure 18:
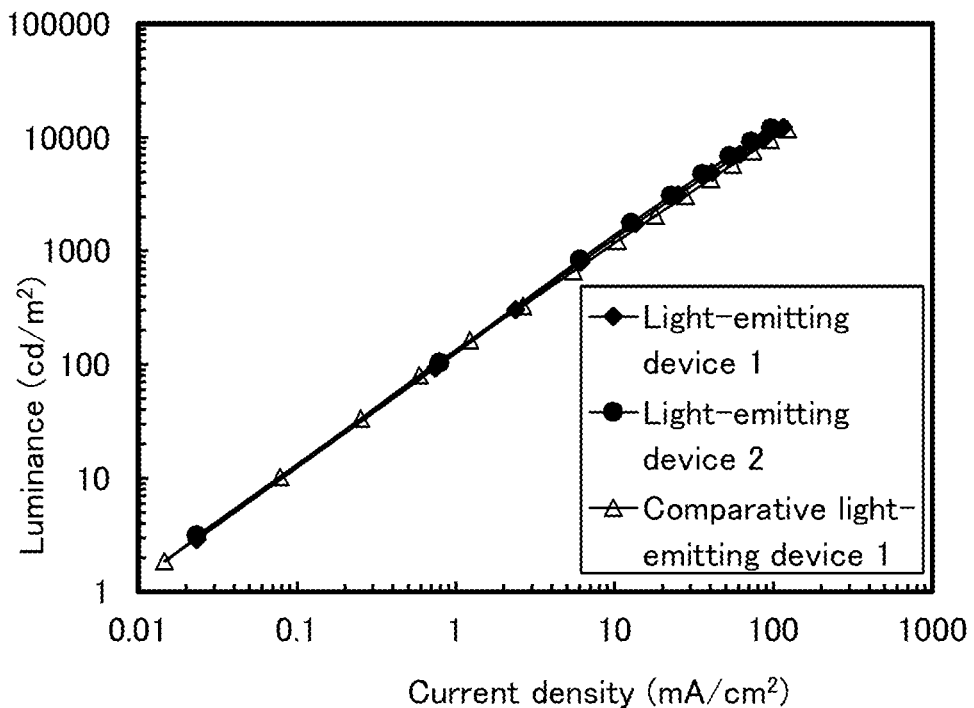
FIG. 18 is luminance-current density characteristics of a light-emitting device 1, a light-emitting device 2, and a comparative light-emitting device 1.
Figure 19:
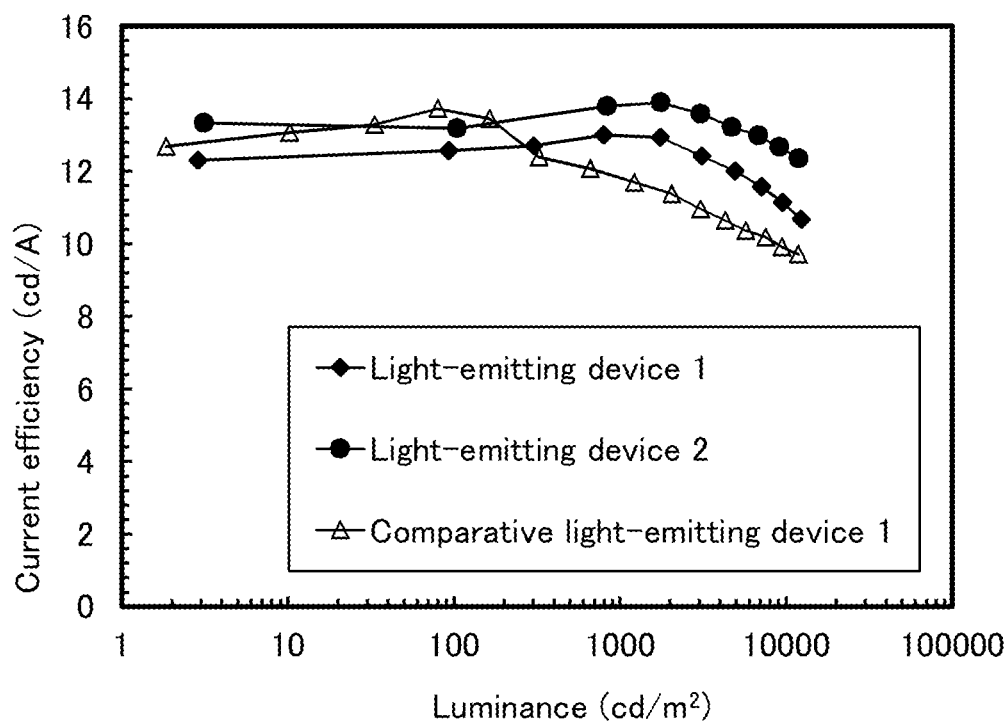
FIG. 19 is current efficiency-luminance characteristics of the light-emitting device 1, the light-emitting device 2, and the comparative light-emitting device 1.
Figure 20:
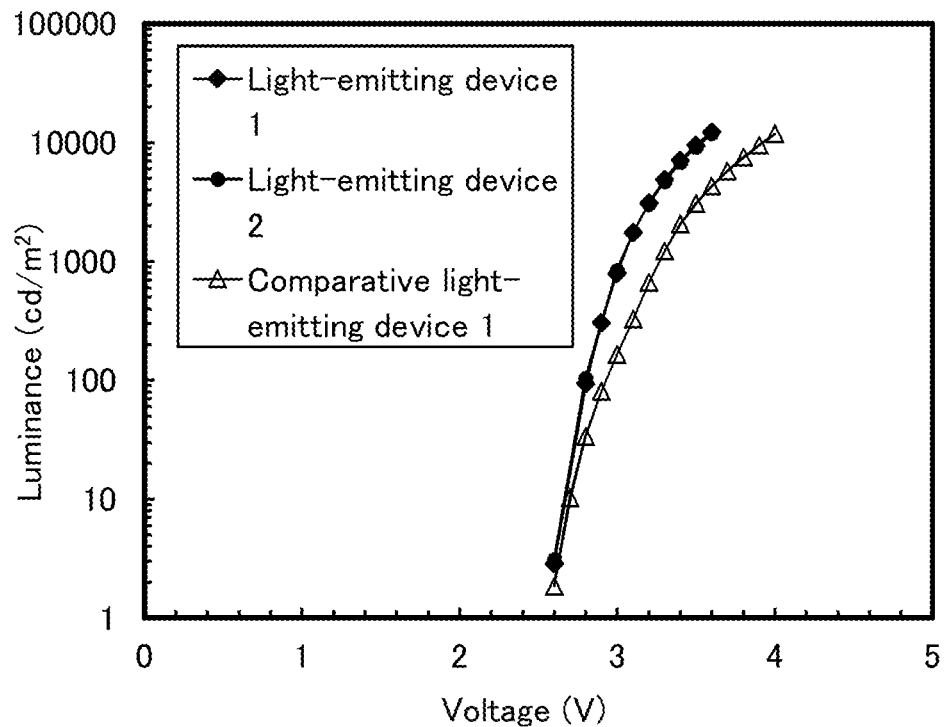
FIG. 20 is luminance-voltage characteristics of the light-emitting device 1, the light-emitting device 2, and the comparative light-emitting device 1.
Figure 21:
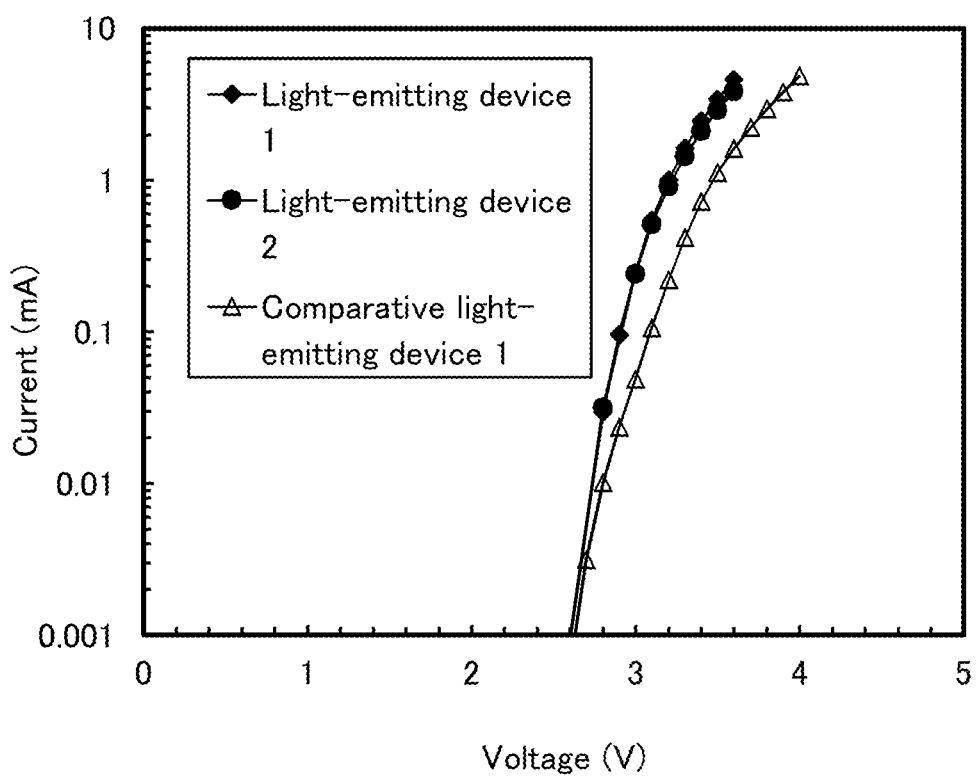
FIG. 21 is current-voltage characteristics of the light-emitting device 1, the light-emitting device 2, and the comparative light-emitting device 1.
Figure 22:
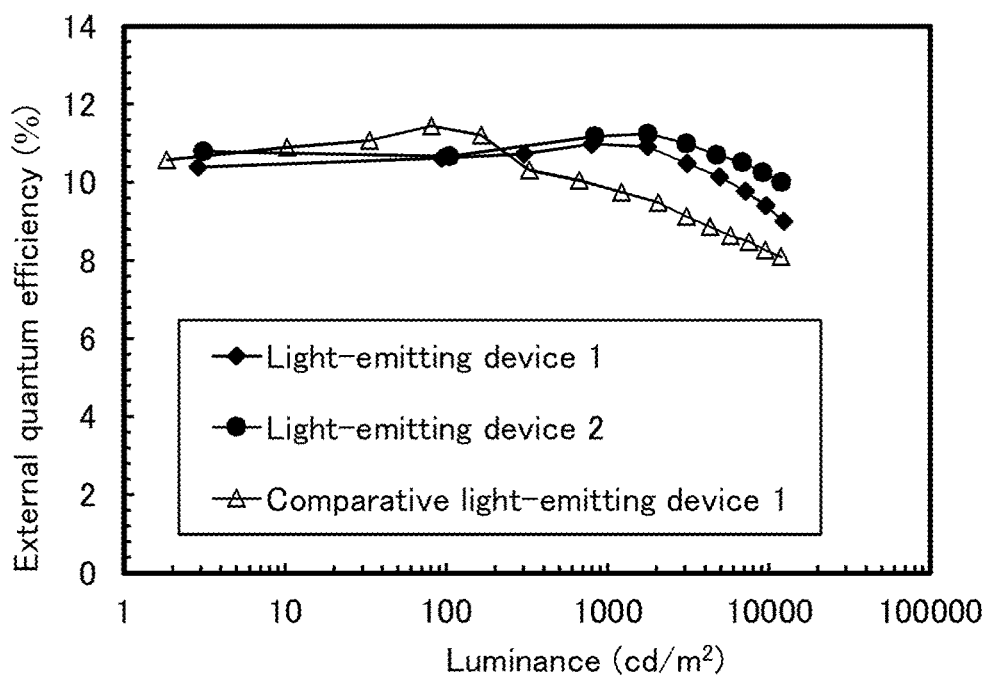
FIG. 22 is external quantum efficiency-luminance characteristics of the light-emitting device 1, the light-emitting device 2, and the comparative light-emitting device 1.
Figure 23:
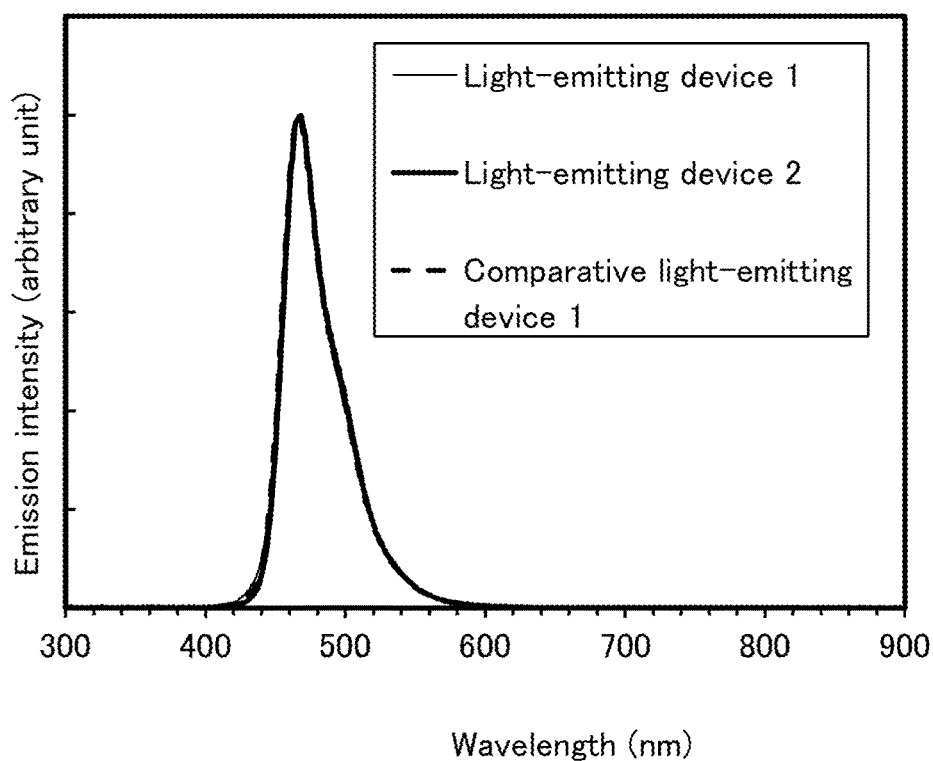
FIG. 23 is emission spectra of the light-emitting device 1, the light-emitting device 2, and the comparative light-emitting device 1.

FIG. 18 shows the luminance-current density characteristics of the light-emitting device 1, the light-emitting device 2, and the comparative light-emitting device 1; FIG. 19, the current efficiency-luminance characteristics; FIG. 20, the luminance-voltage characteristics; FIG. 21, the current-voltage characteristics; FIG. 22, the external quantum efficiency-luminance characteristics; and FIG. 23, the emission spectra. In addition, Table 2 shows the main characteristics of the light-emitting devices at around 1000 cd/m$^2$.

TABLE 2

|  | Voltage (V) | Current (mA) | Current density (mA/cm$^2$) | Chromaticity x | Chromaticity y | Current efficiency (cd/A) | External quantum efficiency (%) |
| --- | --- | --- | --- | --- | --- | --- | --- |
| Light-emitting device 1 | 3.0 | 0.24 | 6.1 | 0.14 | 0.17 | 13.0 | 11.0 |
| Light-emitting device 2 | 3.0 | 0.24 | 6.0 | 0.14 | 0.18 | 13.8 | 11.2 |
| Comparative light-emitting device 1 | 3.3 | 0.42 | 10.4 | 0.14 | 0.17 | 11.7 | 9.7 |

It was found from FIG. 18 to FIG. 23 and Table 2 that the light-emitting device 1 and the light-emitting device 2 that are one embodiment of the present invention were blue light-emitting devices with favorable characteristics such as driving voltage and emission efficiency.

Figure 24:
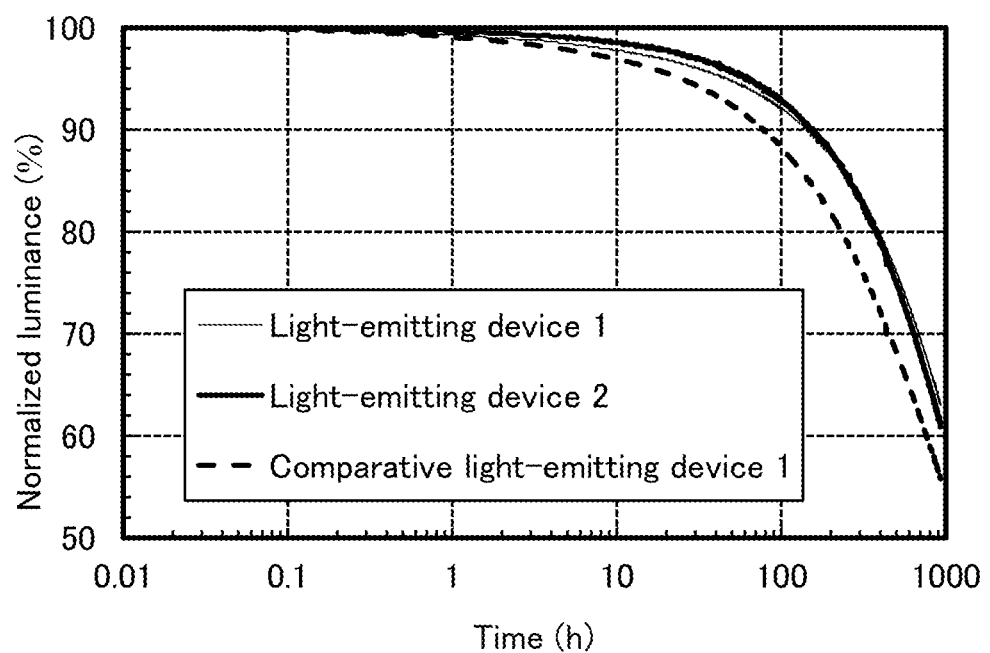
FIG. 24 is normalized luminance-temporal change characteristics of the light-emitting device 1, the light-emitting device 2, and the comparative light-emitting device 1.

FIG. 24 is a graph showing a change in luminance over driving time at a current density of 50 mA/cm². As shown in FIG. 24, the light-emitting device 1 and the light-emitting device 2 that are one embodiment of the present invention were found to be light-emitting devices with favorable lifetime with a small reduction in luminance over the accumulated driving time.

EXAMPLE 4

In this example, a light-emitting device 3 of one embodiment of the present invention described in Embodiment 2, a comparative light-emitting device 2, and a comparative light-emitting device 3 will be described. The structural formulae of organic compounds used in the light-emitting device 3, the comparative light-emitting device 2, and the comparative light-emitting device 3 are shown below.

[Chemical Formula 32]

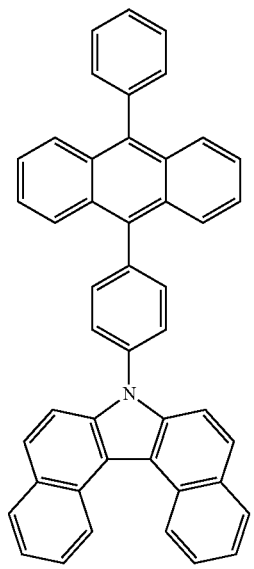

cgDBCzPA
(vii)

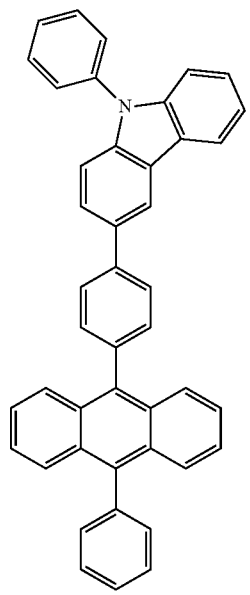

PCzPA
(x)

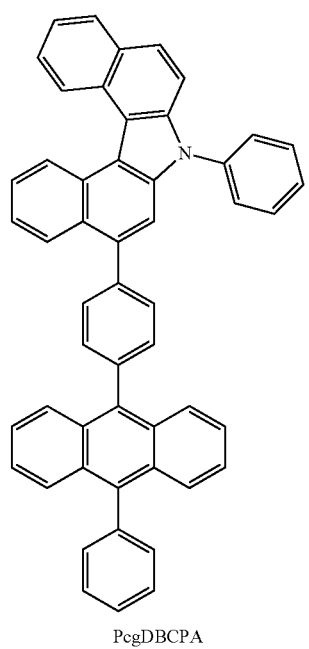

PcgDBCPA
(iv)

-continued (ix)

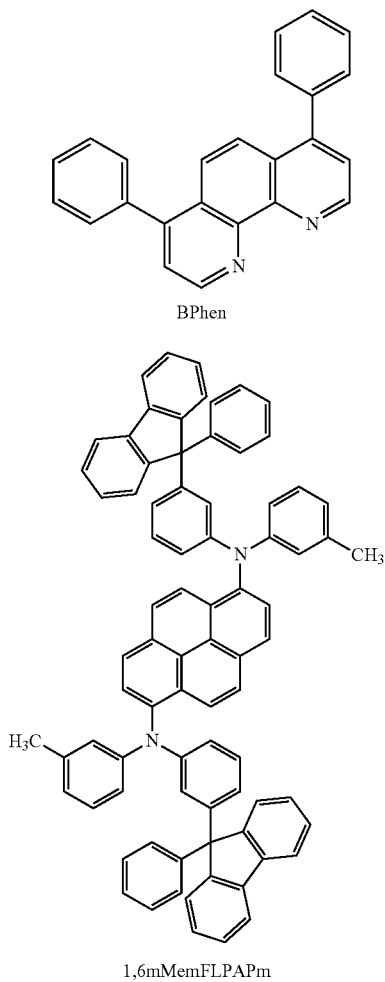

BPhen (viii)

1,6mMemFLPAPrn (Fabricating Method of Light-Emitting Device 3)

First, a film of indium tin oxide containing silicon oxide (ITSO) was formed over a glass substrate by a sputtering method, so that the first electrode 101 was formed. Note that the thickness was 70 nm and the electrode area was 2 mm×2 mm.

Next, in pretreatment for forming the light-emitting device over the substrate, the substrate surface was washed with water and baked at 200° C. for one hour, and then subjected to UV ozone treatment for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and 9-phenyl-3-[4-(10-phenyl-9-anthryl)phenyl]-9H-carbazole (abbreviation: PCzPA) represented by the above structural formula (x) and molybdenum(VI) oxide were co-evaporated over the first electrode 101 to have a weight ratio of 4:2 (=PCzPA: molybdenum oxide) to a thickness of 10 nm by an evaporation method using resistance heating, whereby the hole-injection layer 111 was formed.

Next, over the hole-injection layer 111, PCzPA was evaporated to a thickness of 30 nm to form the hole-transport layer 112.

Next, 7-phenyl-5-[4-(10-phenyl-9-anthryl)phenyl] dibenzo[c,g]carbazole (abbreviation: PcgDBCPA) represented by the above structural formula (iv) and N,N'-bis(3-methylphenyl)-N,N'-bis[3-(9-phenyl-9H-fluoren-9-yl) phenyl]-pylene-1,6-diamine (abbreviation: 1,6mMemFLPAPrn) represented by the above structural formula (viii) were co-evaporated to a thickness of 25 nm to have a weight ratio of 1:0.05 (=PcgDBCPA: 1,6mMemFL-PAPrn), whereby the light-emitting layer 113 was formed.

After that, over the light-emitting layer 113, PcgDBCPA was evaporated to a thickness of 10 nm, and bathophenanthroline (abbreviation: BPhen) represented by the above structural formula (ix) was evaporated to a thickness of 15 nm, whereby the electron-transport layer 114 was formed.

After the formation of the electron-transport layer 114, lithium fluoride (LiF) was evaporated to a thickness of 1 nm to form the electron-injection layer 115, and then aluminum was evaporated to a thickness of 200 nm to form the second electrode 102, whereby the light-emitting device 3 of this example was fabricated.

(Fabricating Method of Comparative Light-Emitting Device 2)

The comparative light-emitting device 2 was fabricated in a manner similar to that of the light-emitting device 3 except that PcgDBCPA used in the light-emitting layer 113 and the electron-transport layer 114 of the light-emitting device 3 was replaced with 7-[4-(10-phenyl-9-anthryl)phenyl]-7H-dibenzo[c,g]carbazole (abbreviation: cgDBCzPA) represented by the above structural formula (vii) and the weight ratio of cgDBCzPA to 1,6mMemFLPAPrn in the light-emitting layer was 1:0.03 (=cgDBCzPA: 1,6mMemFLPA-Prn).

(Fabricating Method of Comparative Light-Emitting Device 3)

The comparative light-emitting device 3 was fabricated in a manner similar to that of the light-emitting device 3 except that PcgDBCPA used in the light-emitting layer 113 and the electron-transport layer 114 of the light-emitting device 3 was replaced with PCzPA, and the weight ratio of PCzPA to 1,6mMemFLPAPrn in the light-emitting layer was 1:0.03 (=cgDBCzPA: 1,6mMemFLPAPrn).

The device structures of the light-emitting device 3, the comparative light-emitting device 2, and the comparative light-emitting device 3 are listed in the following table.

TABLE 3

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 inn |
| Light-emitting device 3 | PCzPA: MoOx (4:2) | PCzPA | PcgDBCPA: 1,6mMemFLPAPrn (1:0.05) | PcgDBCPA | BPhea | LiF |

TABLE 3-continued

|  | Hole-injection layer | Hole-transport layer | Light-emitting layer | Electron-transport layer | | Electron-injection layer |
| --- | --- | --- | --- | --- | --- | --- |
|  | 10 nm | 30 nm | 25 nm | 10 nm | 15 nm | 1 nm |
| Comparative light-emitting device 2 |  |  | cgDBCzPA 1,6mMemFLPAPrn (1:0.03) | cgDBCzPA |  |  |
| Comparative light-emitting device 3 |  |  | PCzPA: 1,6mMemFLPAPrn (1:0.03) | PCzPA |  |  |

Each of the light-emitting device 3, the comparative light-emitting device 2, and the comparative light-emitting device 3 was subjected to sealing with a glass substrate (a sealant was applied to surround the device, followed by UV treatment and one-hour heat treatment at 80° C. at the time of sealing) in a glove box containing a nitrogen atmosphere so that the light-emitting device is not exposed to the air, and then the initial characteristics and reliabilities of these light-emitting devices were measured. Note that the measurement was carried out at room temperature.

Figure 25:
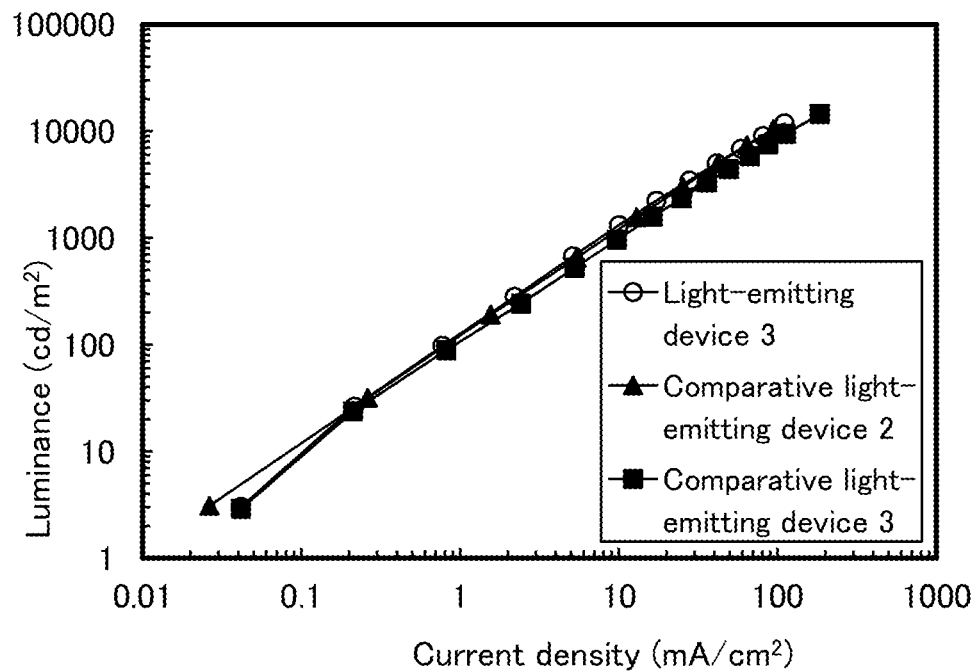
FIG. 25 is luminance-current density characteristics of a light-emitting device 3, a comparative light-emitting device 2, and a comparative light-emitting device 3.
Figure 26:
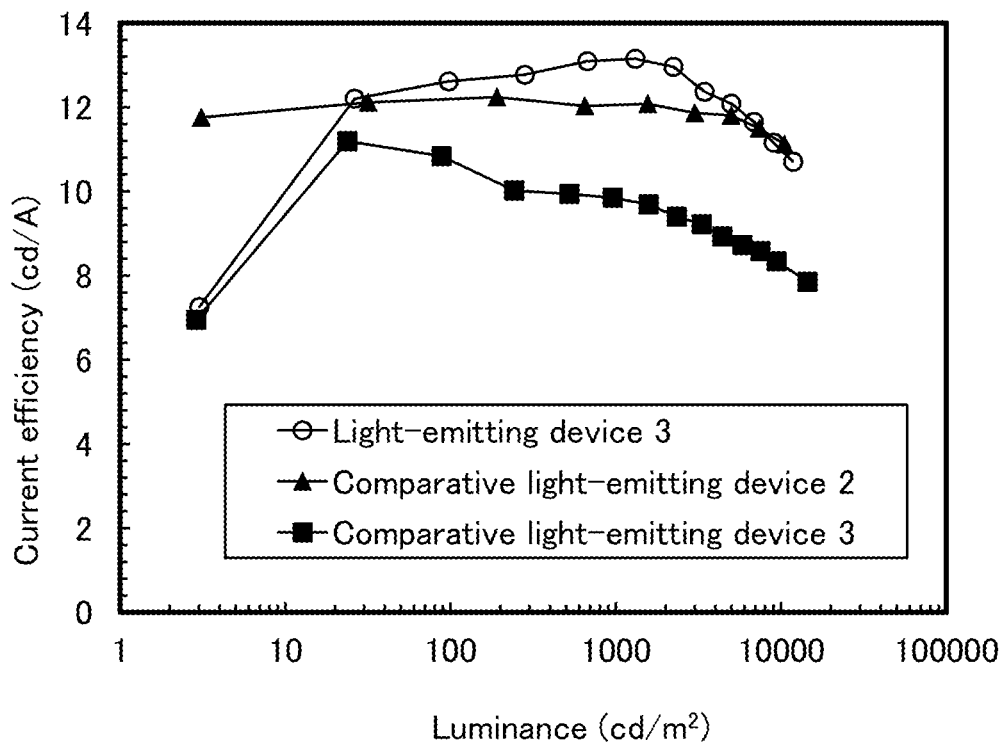
FIG. 26 is current efficiency-luminance characteristics of the light-emitting device 3, the comparative light-emitting device 2, and the comparative light-emitting device 3.
Figure 27:
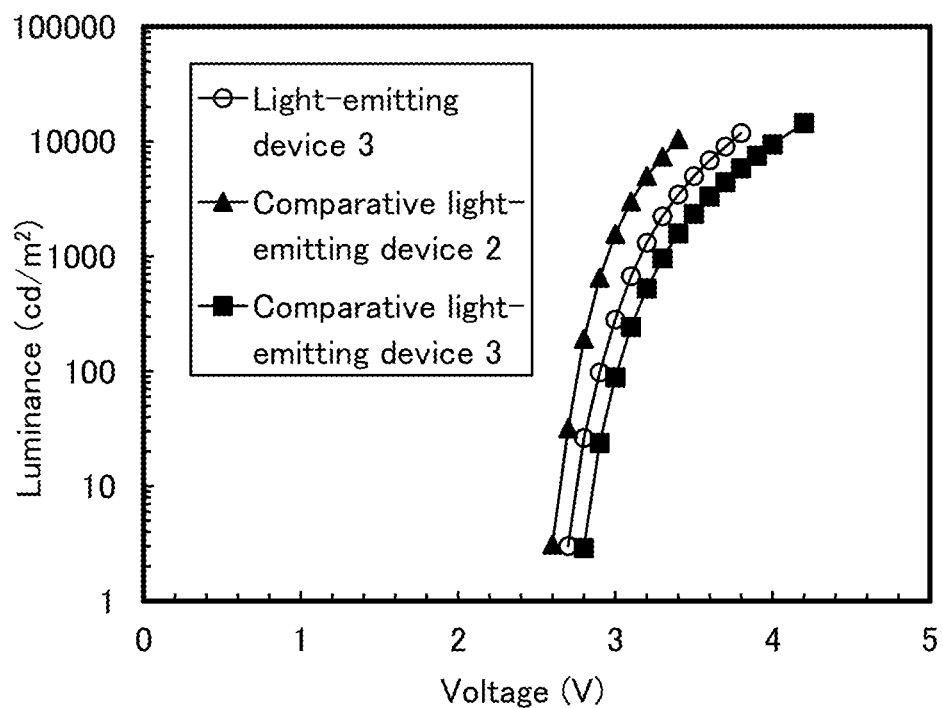
FIG. 27 is luminance-voltage characteristics of the light-emitting device 3, the comparative light-emitting device 2, and the comparative light-emitting device 3.
Figure 28:
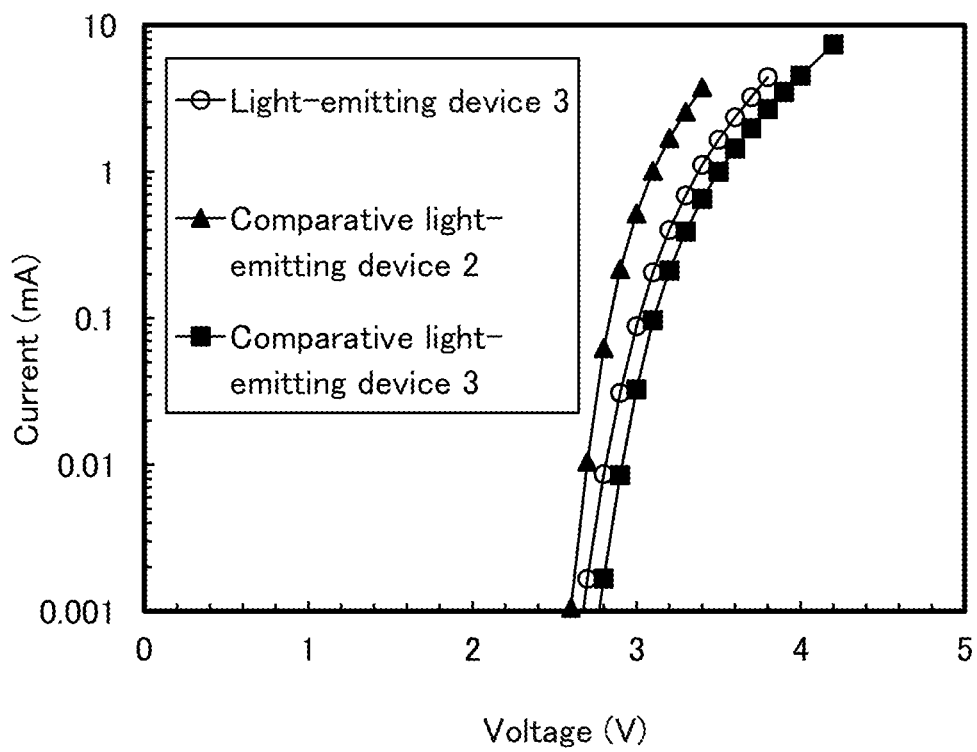
FIG. 28 is current-voltage characteristics of the light-emitting device 3, the comparative light-emitting device 2, and the comparative light-emitting device 3.
Figure 29:
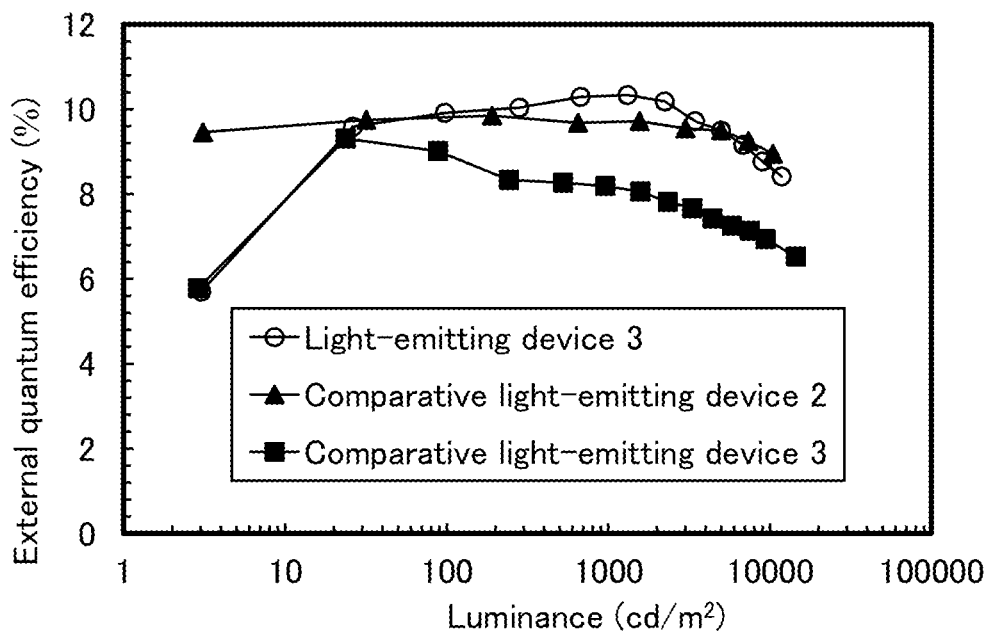
FIG. 29 is external quantum efficiency-luminance characteristics of the light-emitting device 3, the comparative light-emitting device 2, and the comparative light-emitting device 3.
Figure 30:
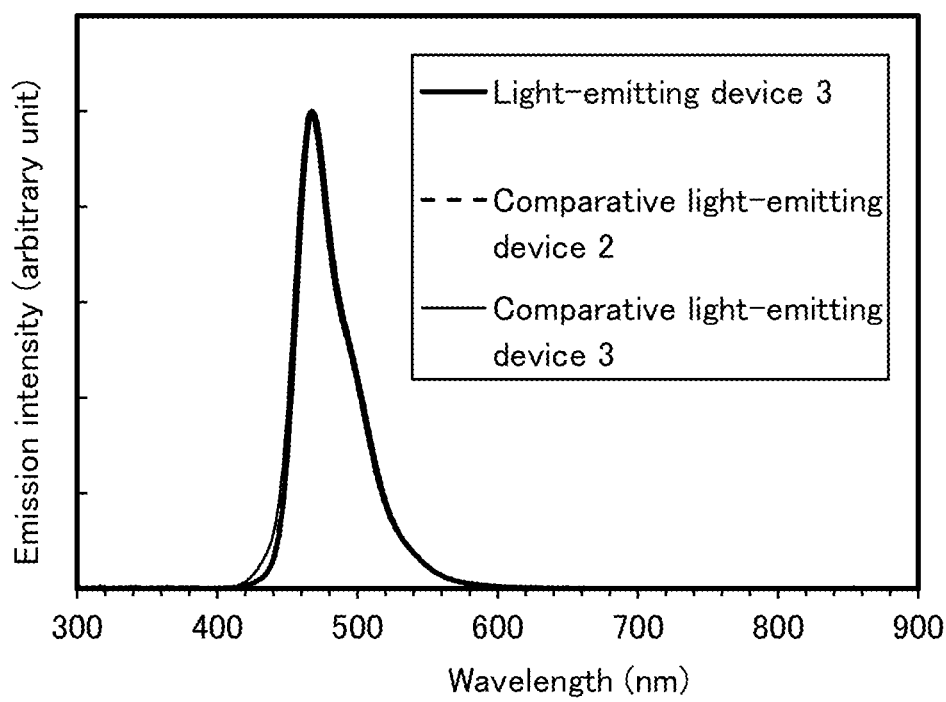
FIG. 30 is emission spectra of the light-emitting device 3, the comparative light-emitting device 2, and the comparative light-emitting device 3.

FIG. 25 shows the luminance-current density characteristics of the light-emitting device 3, the comparative light-emitting device 2, and the comparative light-emitting device 3; FIG. 26, the current efficiency-luminance characteristics; FIG. 27, the luminance-voltage characteristics; FIG. 28, the current-voltage characteristics; FIG. 29, the external quantum efficiency-luminance characteristics; and FIG. 30, the emission spectra. In addition, Table 4 shows the main characteristics of the light-emitting devices at around 1000 cd/m$^2$.

TABLE 4

|  | Voltage (V) | Current (mA) | Current density (mA/cm$^2$) | Chromaticity x | Chromaticity y | Current efficiency (cd/A) | External quantum efficiency (%) |
| --- | --- | --- | --- | --- | --- | --- | --- |
| Light-emitting device 3 | 3.2 | 0.40 | 10.0 | 0.14 | 0.19 | 13.1 | 10.3 |
| Comparative light-emitting device 2 | 2.9 | 0.22 | 5.4 | 0.14 | 0.18 | 12.0 | 9.7 |
| Comparative light-emitting device 3 | 3.3 | 0.39 | 9.7 | 0.14 | 0.17 | 9.8 | 8.2 |

It was found from FIG. 25 to FIG. 30 and Table 4 that the light-emitting device 3 of one embodiment of the present invention was a blue light-emitting device with favorable characteristics such as driving voltage and emission efficiency.

EXAMPLE 5

Synthesis Example 3

In this example, a synthesis method of 7-phenyl-5-(10-phenyl-9-anthryl)dibenzo[c,g]carbazole (abbreviation: PcgDBCPhA) will be described in detail. The structural formula of PcgDBCPhA is shown below.

[Chemical Formula 33]

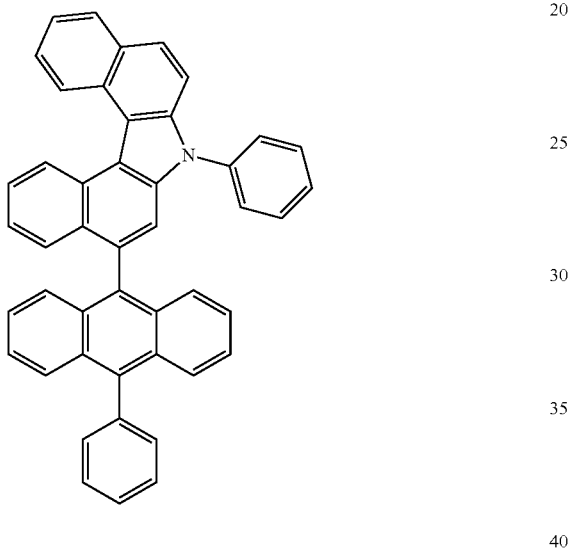

To a 100-mL three-neck flask were added 1.3 g (3.0 mmol) of 5-bromo-7-phenyldibenzo[c,g]carbazole, 1.8 g (6.0 mmol) of 10-phenylanthracen-9-boronic acid, 0.60 g (2.0 mmol) of tris(2-methylphenyl)phosphine, 0.88 g (6.4 mmol) of potassium carbonate, 30 mL of toluene, 3 mL of ethanol, and 3 mL of water. This mixture was degassed by being stirred under reduced pressure, and the air in the flask was replaced with nitrogen. To this mixture was added 0.21 g (0.93 mmol) of palladium(II) acetate and the mixture was stirred at 80° C. under a nitrogen stream for 35 hours. After the stirring, water was added to this mixture, and an aqueous layer was subjected to extraction with toluene so that the aqueous layer and an organic layer were separated from each other. The obtained organic layer was washed with water and a saturated saline solution, and dried with magnesium sulfate. This mixture was subjected to gravity filtration and the obtained filtrate was concentrated, whereby a solid was obtained. The obtained solid was purified by silica gel column chromatography (toluene:hexane=1:4) and a high-performance liquid chromatography (chloroform). The obtained solid was washed with ethyl acetate, whereby 0.86 g of a white powder, which was the target substance, was obtained in a yield of 48%. The synthesis scheme of is shown below.

[Chemical Formula 34]

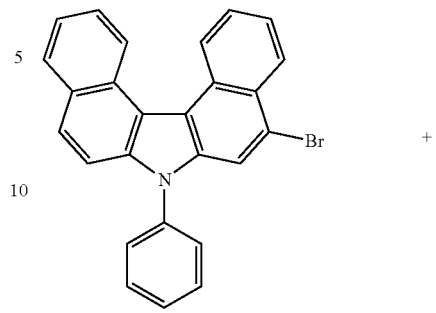

By a train sublimation method, 0.85 g of the obtained white powder was purified by sublimation. The sublimation purification was performed by heating at 360° C. for 17 hours and then at 370° C. for four hours under the conditions where the pressure was 4.2 Pa and the argon flow rate was 5 mL/min. After the sublimation purification, 0.70 g of a pale yellow powder was obtained at a collection rate of 82%.

Figure 31A:
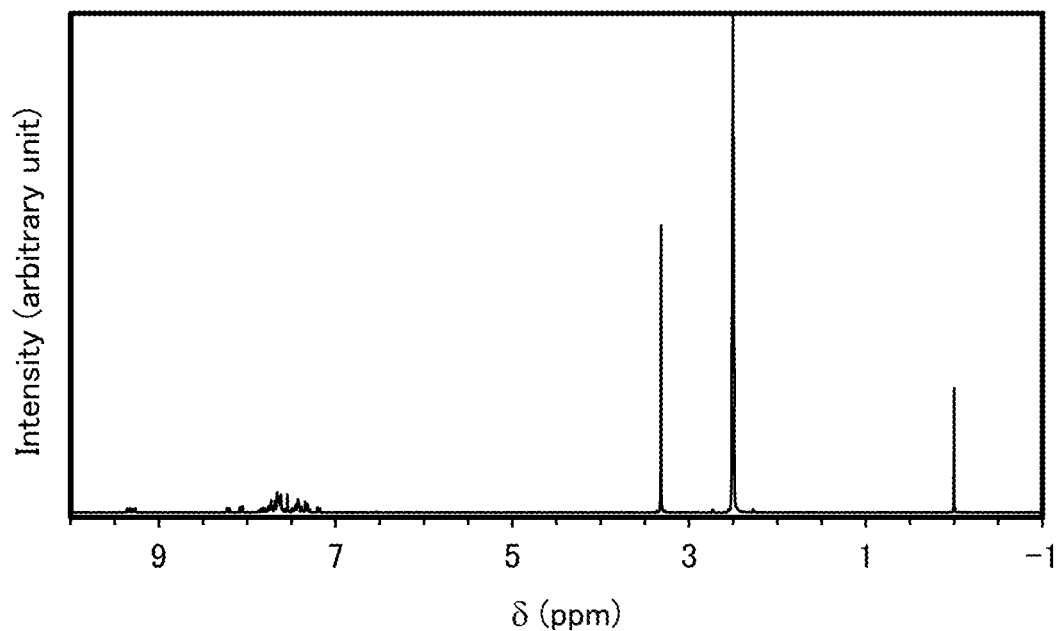
FIGS. 31A and 31B are $^1$H NMR spectra of PcgDBCPhA.
Figure 31B:
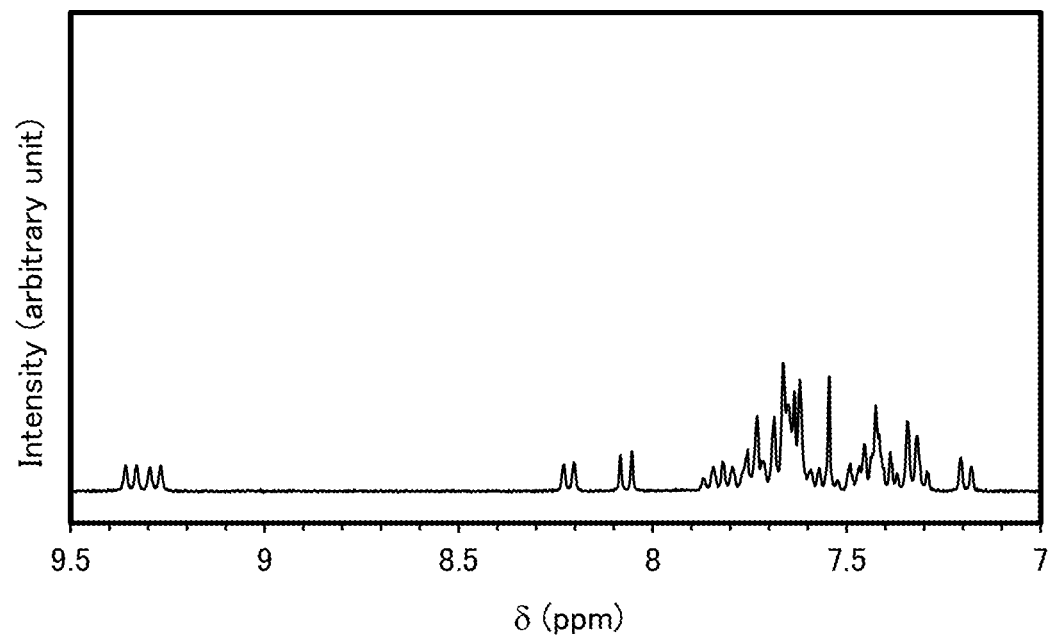

FIGS. 31(A) and 31(B) show $^1$H NMR charts of the obtained compound, and the numerical data is shown below. Note that FIG. 31(B) is a graph where the range from 7 ppm to 9.5 ppm in FIG. 31(A) is enlarged. This indicates that PcgDBCPhA, which is the organic compound of one embodiment of the present invention, was obtained in this synthesis example.

$^1$H NMR (DMSO-d6, 300 MHz): δ=7.19 (d, J=7.8 Hz, 1H), 7.29-7.87 (m, 24H), 8.07 (d, J=8.7 Hz, 1H), 8.22 (d, J=7.8 Hz, 1H), 9.28 (d, J=8.4 Hz, 1H), 9.34 (d, J=8.7 Hz, 1H).

Figure 32:
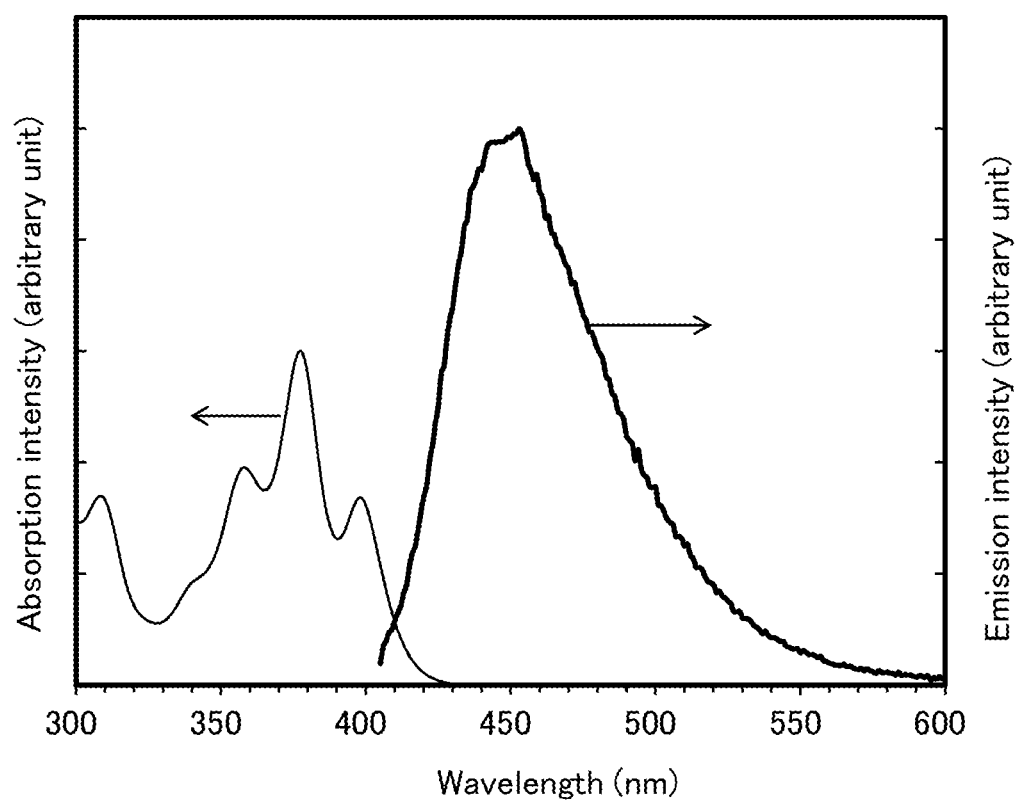
FIG. 32 is an absorption spectrum and an emission spectrum of PcgDBCPhA in a solution state.
Figure 33:
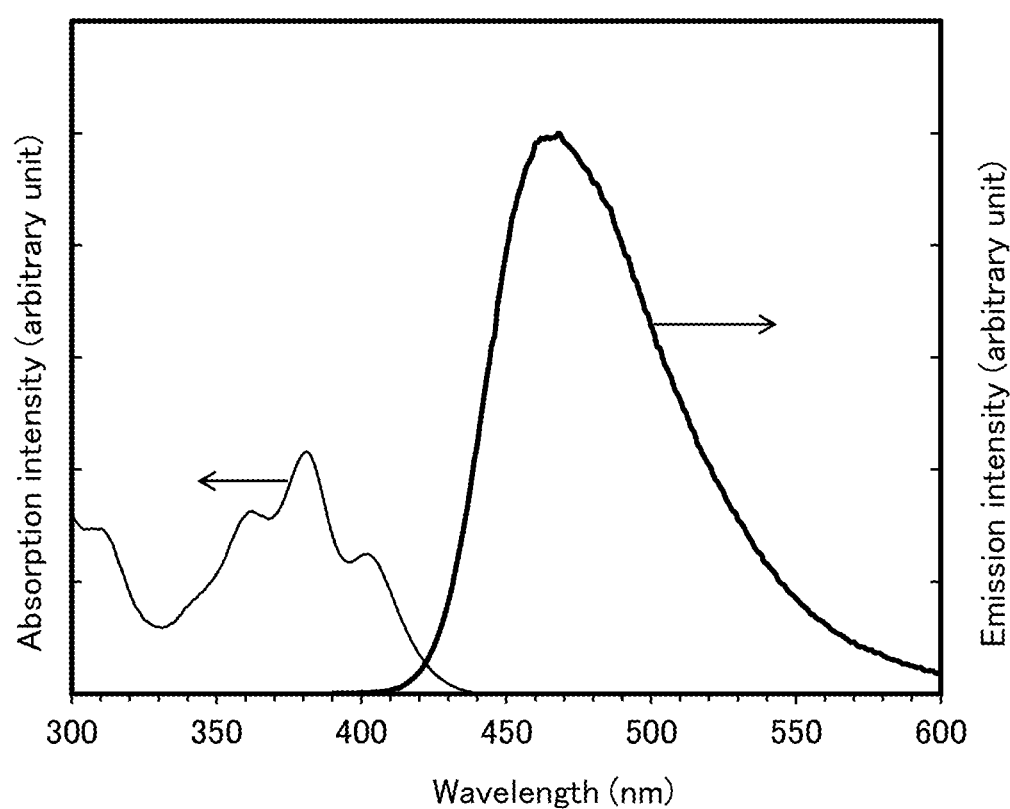
FIG. 33 is an absorption spectrum and an emission spectrum of PcgDBCPhA in a thin film state.

Next, FIG. 32 shows an absorption spectrum and an emission spectrum of PcgDBCPhA in a toluene solution. In addition, FIG. 33 shows an absorption spectrum and an emission spectrum of a thin film. The solid thin film was formed over a quartz substrate by a vacuum evaporation method. The absorption spectrum in the solution was measured with an ultraviolet-visible spectrophotometer (V550, produced by JASCO Corporation). The absorption spectrum of PcgDBCPhA in the toluene solution shown in FIG. 32 was obtained by subtracting an absorption spectrum of toluene measured when only toluene was put in a quartz cell from the absorption spectrum of PcgDBCPhA in the toluene solution. The absorption spectrum of the thin film was measured using a spectrophotometer (U4100 Spectrophotometer, manufactured by Hitachi High-Technologies Corporation). The emission spectra were measured using a fluorescence spectrophotometer (FS920 manufactured by Hamamatsu Photonics K.K.).

As shown in FIG. 32, in the case of PcgDBCPhA in the toluene solution, absorption peaks were observed at around 398 nm, 377 nm, 358 nm, and 308 nm, and an emission wavelength peak was observed at around 452 nm (excitation wavelength: 398 nm). Furthermore, as shown in FIG. 33, in the case of the thin film of PcgDBCPhA, the absorption peaks were observed at around 402 nm, 381 nm, 362 nm, 342 nm, and 310 nm, and the emission wavelength peak was observed at around 468 nm (excitation wavelength: 380 nm). PcgDBCPhA was confirmed to emit blue light. The compound of one embodiment of the present invention can be used as a host for a light-emitting substance or a substance that exhibits fluorescence in the visible region.

Furthermore, the thin film of PcgDBCPhA was found to have a good film quality with little change in shape, hardly being aggregated even under air.

The HOMO level and the LUMO level of PcgDBCPhA were calculated on the basis of a cyclic voltammetry (CV) measurement. Since the calculation method is similar to the method described in Example 1, the description thereof is omitted. Example 1 should be referred to.

As a result, the HOMO level was found to be −5.70 eV in the measurement of the oxidation potential Ea[V] of PcgDBCPhA. In contrast, the LUMO level was found to be −2.73 eV in the measurement of the reduction potential Ec[V].

EXAMPLE 6

In this example, a light-emitting device 4 of one embodiment of the present invention described in Embodiment 2 will be described. The structural formulae of organic compounds used for the light-emitting device 4 are shown below.

[Chemical Formula 35]

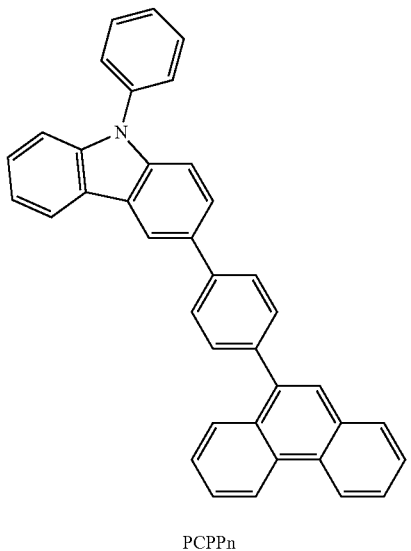

PCPPn

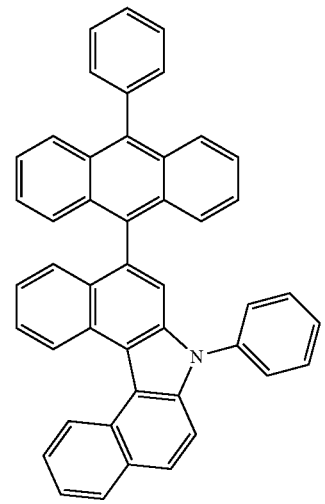

PcgDBCPhA

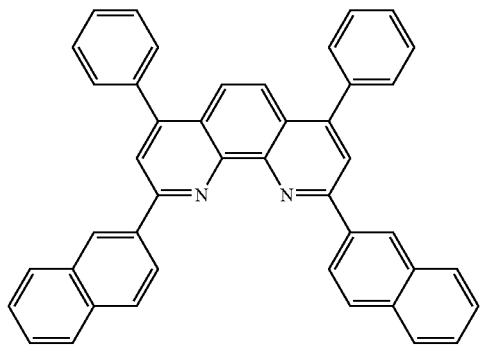

NBPhen (Fabricating Method of Light-Emitting Device 4)

First, a film of indium tin oxide containing silicon oxide (ITSO) was formed over a glass substrate by a sputtering method, so that the first electrode 101 was formed. Note that the thickness was 70 nm and the electrode area was 2 mm×2 mm.

Next, in pretreatment for forming the light-emitting device over the substrate, the substrate surface was washed with water and baked at 200° C. for one hour, and then subjected to UV ozone treatment for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and 3-[4-(9-phenanthryl)-phenyl]-9-phenyl-9H-carbazole (abbreviation: PCPPn) represented by the structural formula (xi) and molybdenum(VI) oxide were co-evaporated over the first electrode to have a weight ratio of 4:2 (=PCPPn: molybdenum oxide) to a thickness of 10 nm by an evaporation method using resistance heating, whereby the hole-injection layer 111 was formed.

Next, over the hole-injection layer 111, PCPPn was evaporated to a thickness of 30 nm to form the hole-transport layer 112.

Next, 7-phenyl-5-(10-phenyl-9-anthryl)dibenzo[c,g]carbazole (abbreviation: PcgDBCPhA) represented by the above structural formula (xii) was evaporated to a thickness of 25 nm, whereby the light-emitting layer 113 was formed.

After that, over the light-emitting layer 113, 2,9-bis(naphthalen-2-yl)-4,7-diphenyl-1,10-phenanthroline (abbreviation: NBPhen) represented by the above structural formula (xiii) was evaporated to a thickness of 25 nm, whereby the electron-transport layer 114 was formed.

After the formation of the electron-transport layer 114, lithium fluoride (LiF) was evaporated to a thickness of 1 nm to form the electron-injection layer 115, and aluminum was evaporated to a thickness of 200 nm to form the second electrode 102, whereby the light-emitting device 4 of this example was fabricated.

The device structure of the light-emitting device 4 is listed in the following table.

TABLE 5

|  | Hole-injection layer 10 nm | Hole-transport layer 30 nm | Light-emitting layer 25 nm | Electron-transport layer 25 nm | Electron-injection layer 1 nm |
|---|---|---|---|---|---|
| Light-emitting device 4 | PCPPn: MoOx (4:2) | PCPPn | PcgDBCPhA | NBPhen | LiF |

The light-emitting device 4 was subjected to sealing with a glass substrate (a sealant was applied to surround the device, followed by UV treatment and one-hour heat treatment at 80° C. at the time of sealing) in a glove box containing a nitrogen atmosphere so that the light-emitting device is not exposed to the air, and then the initial characteristics and reliability of this light-emitting device were measured. Note that the measurement was carried out at room temperature.

Figure 34:
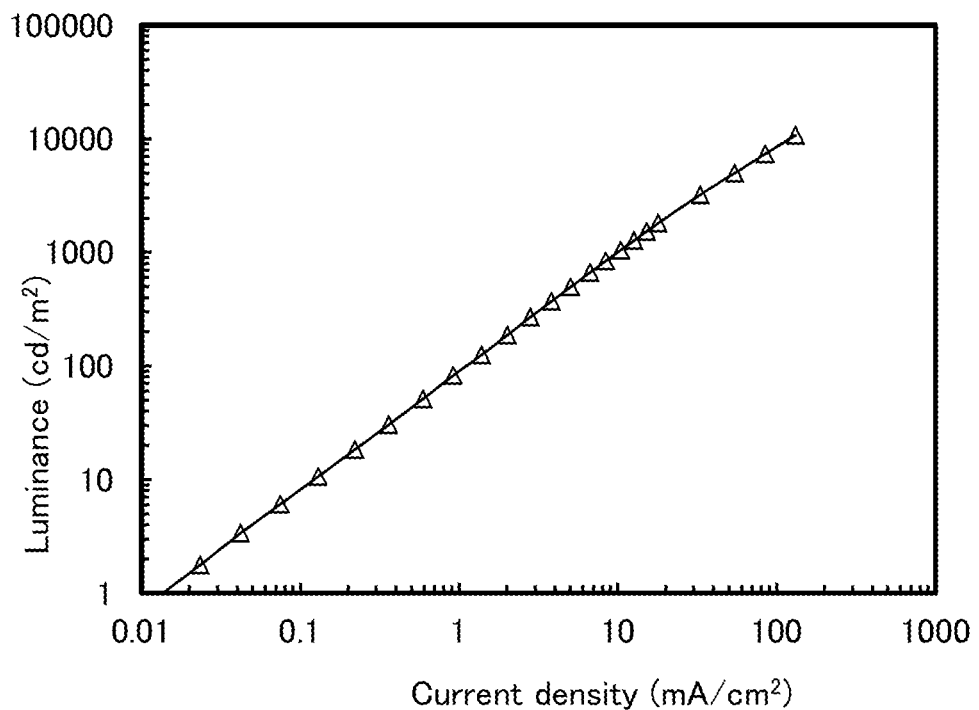
FIG. 34 is luminance-current density characteristics of a light-emitting device 4.
Figure 35:
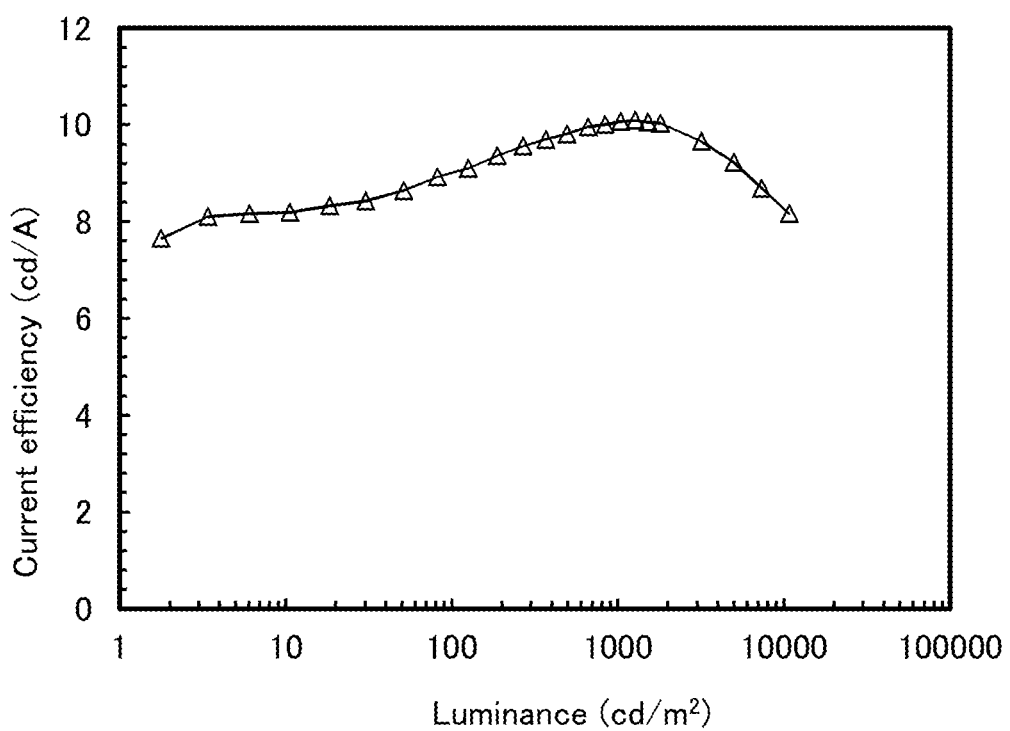
FIG. 35 is current efficiency-luminance characteristics of the light-emitting device 4.
Figure 36:
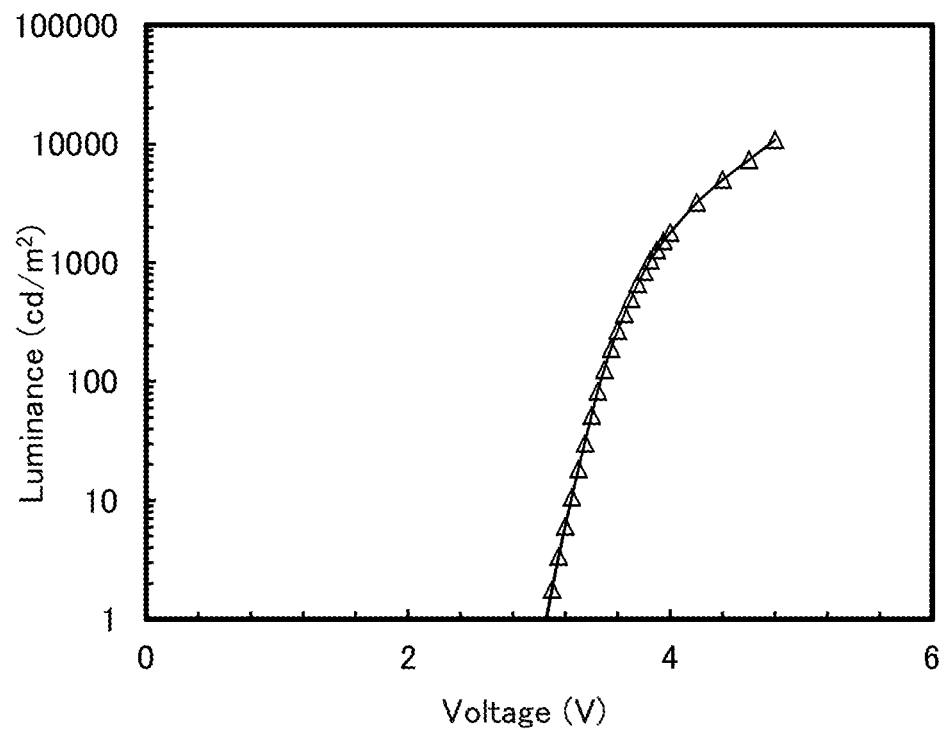
FIG. 36 is luminance-voltage characteristics of the light-emitting device 4.
Figure 37:
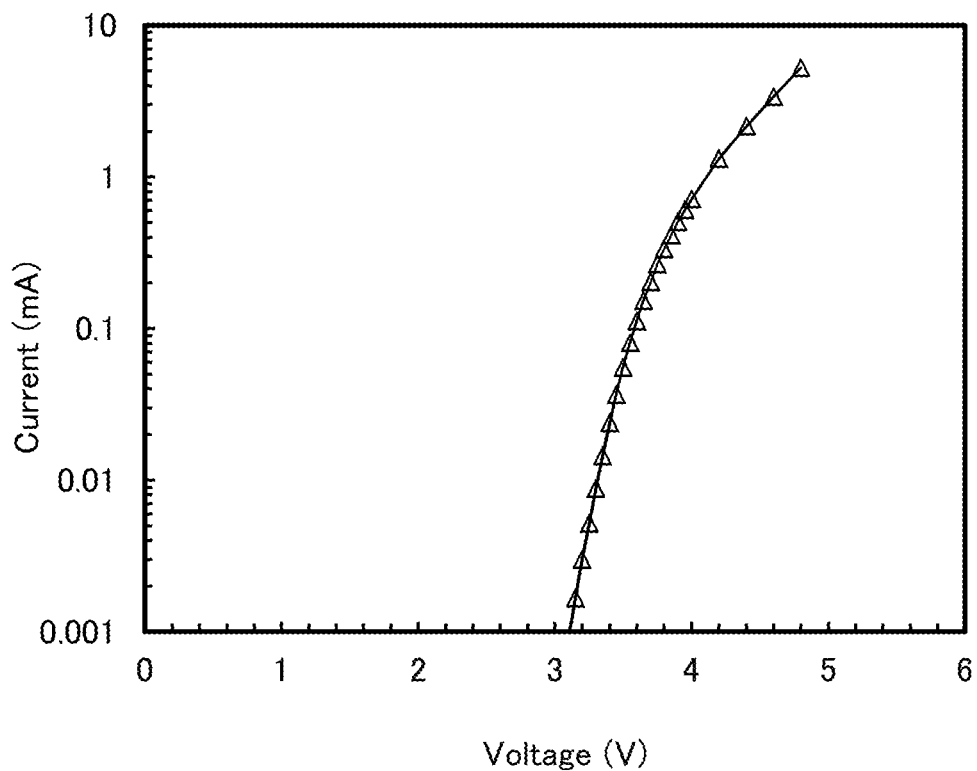
FIG. 37 is current-voltage characteristics of the light-emitting device 4.
Figure 38:
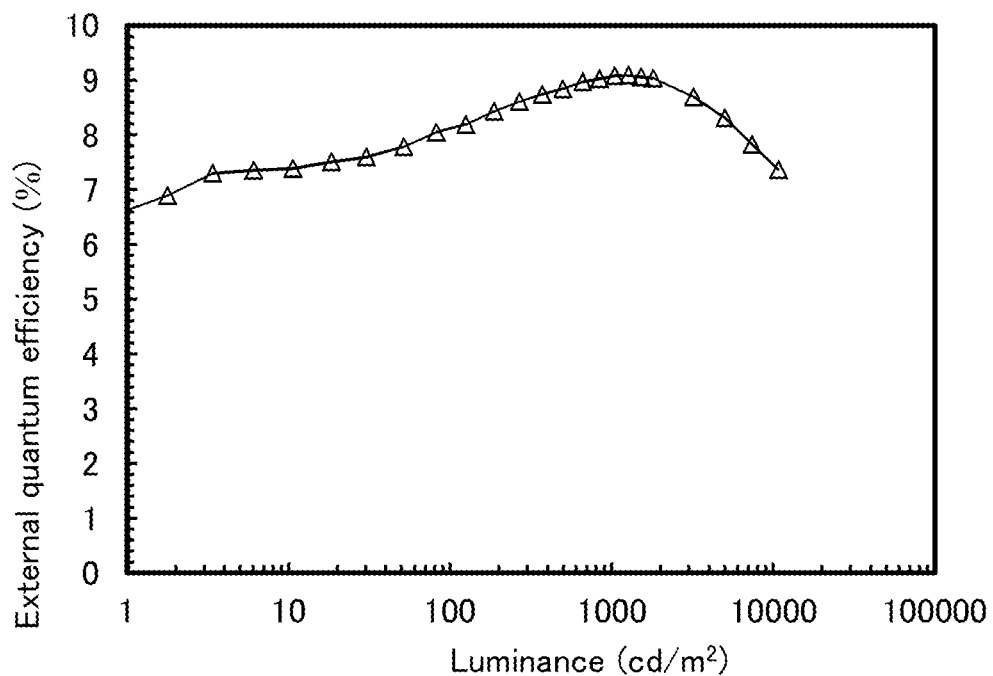
FIG. 38 is external quantum efficiency-luminance characteristics of the light-emitting device 4.
Figure 39:
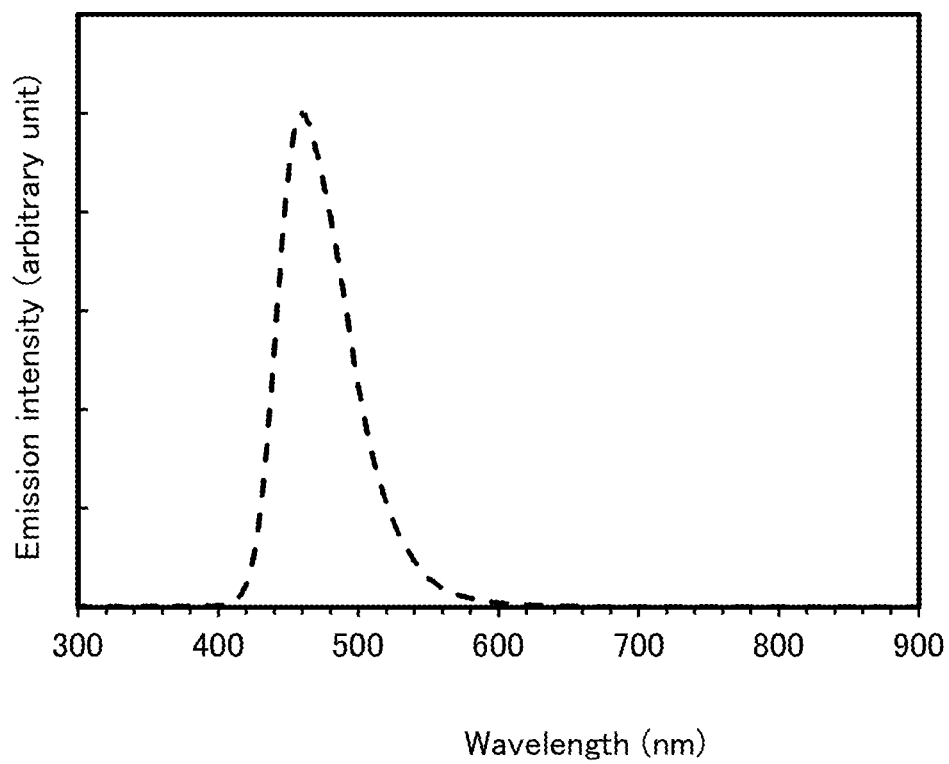
FIG. 39 is an emission spectrum of the light-emitting device 4.
Figure 40:
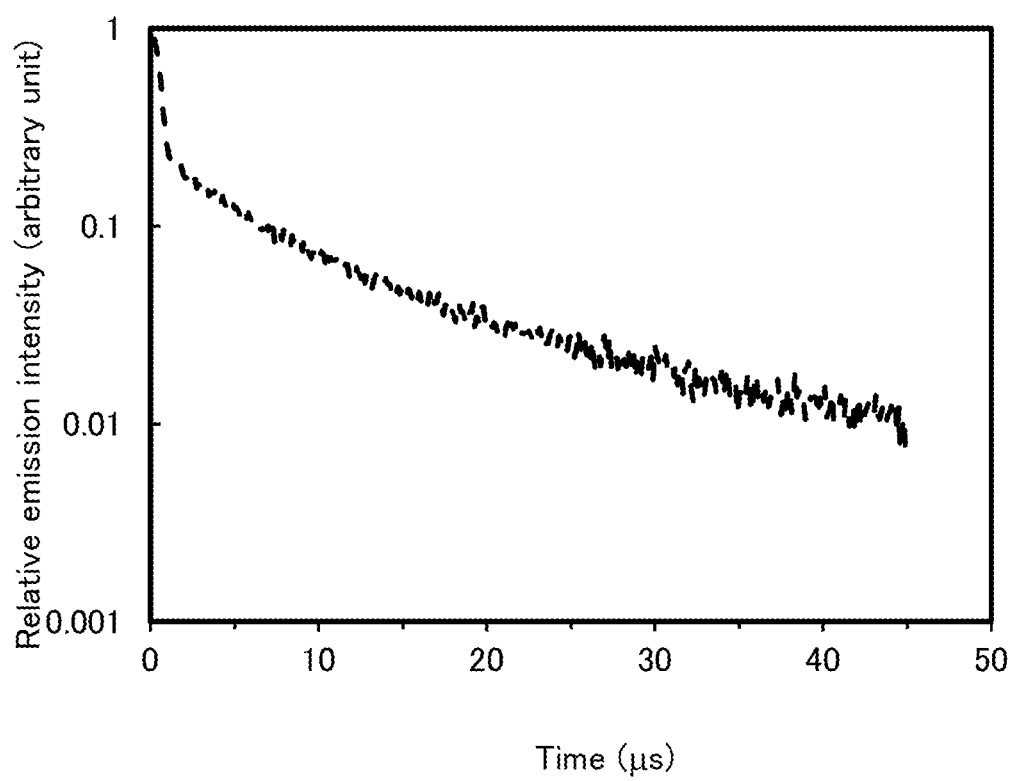
FIG. 40 is the measurement results of transient EL of the light-emitting device 4.

FIG. 34 shows the luminance-current density characteristics of the light-emitting device 4; FIG. 35, the current efficiency-luminance characteristics; FIG. 36, the luminance-voltage characteristics; FIG. 37, the current-voltage characteristics; FIG. 38, the external quantum efficiency-luminance characteristics; FIG. 39, the emission spectrum; and FIG. 40, the transient EL characteristics. Table 6 shows the main characteristics of the light-emitting device at around 1000 cd/m².

TABLE 6

|  | Voltage (V) | Current (mA) | Current density (mA/cm²) | Chromaticity x | Chromaticity y | Current efficiency (cd/A) | External quantum efficiency (%) |
|---|---|---|---|---|---|---|---|
| Light-emitting device 4 | 3.9 | 0.41 | 10.4 | 0.14 | 0.14 | 10.1 | 9.1 |

It was found from FIG. 34 to FIG. 40 and Table 6 that the light-emitting device 4 of one embodiment of the present invention was a blue light-emitting device with favorable characteristics. It was also found from FIG. 40 that the proportion of delayed fluorescence components in EL emission in the light-emitting device 4 was as high as 23.9%.

EXAMPLE 7

In this example, a light-emitting device 5 of one embodiment of the present invention described in Embodiment 2 will be described. The structural formulae of organic compounds used in the light-emitting device 5 are shown below.

[Chemical Formula 36]

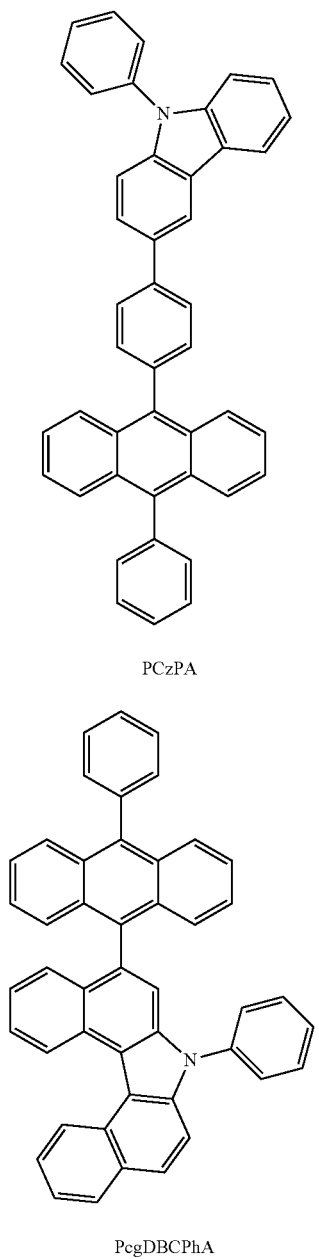

PCzPA (x)

PcgDBCPhA (xii)

-continued

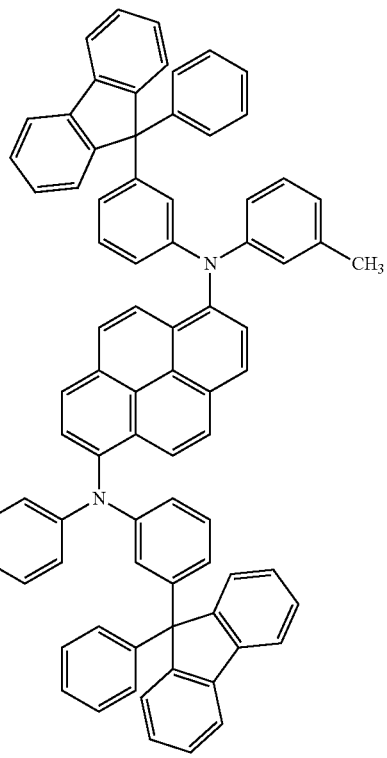

1,6mMemFLAPrn (viii)

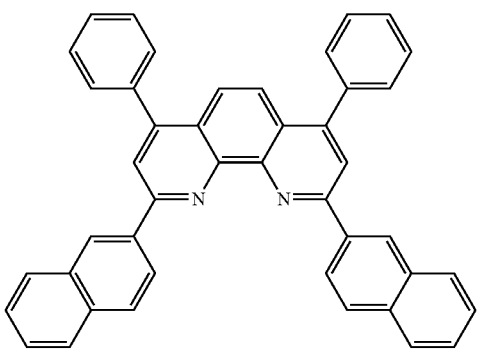

NBPhen (xiii)

(Fabricating Method of Light-Emitting Device 5)

First, a film of indium tin oxide containing silicon oxide (ITSO) was formed over a glass substrate by a sputtering method, so that the first electrode 101 was formed. Note that the thickness was 70 nm and the electrode area was 2 mm×2 mm.

Next, in pretreatment for forming the light-emitting device over the substrate, the substrate surface was washed with water and baked at 200° C. for one hour, and then subjected to UV ozone treatment for 370 seconds.

After that, the substrate was transferred into a vacuum evaporation apparatus in which the pressure was reduced to about $10^{-4}$ Pa, vacuum baking at 170° C. for 30 minutes was performed in a heating chamber in the vacuum evaporation apparatus, and then the substrate was naturally cooled down for about 30 minutes.

Next, the substrate over which the first electrode 101 was formed was fixed to a substrate holder provided in the vacuum evaporation apparatus so that the surface over which the first electrode 101 was formed faced downward, and 9-phenyl-3-[4-(10-phenyl-9-anthryl)phenyl]-9H-carbazole (abbreviation: PCzPA) represented by the above structural formula (x) and molybdenum(VI) oxide were co-evaporated over the first electrode 101 to have a weight ratio of 4:2 (=PCzPA: molybdenum oxide) to a thickness of 10 nm by an evaporation method using resistance heating, whereby the hole-injection layer 111 was formed.

Next, over the hole-injection layer 111, PCzPA was evaporated to a thickness of 30 nm to form the hole-transport layer 112.

Next, 7-phenyl-5-(10-phenyl-9-anthryl)-7H-dibenzo[c,g]carbazole (abbreviation: PcgDBCPhA) represented by the above structural formula (xii) and N,N'-bis(3-methylphenyl)-N,N'-bis[3-(9-phenyl-9H-fluoren-9-yl)phenyl]-pylene-1,6-diamine (abbreviation: 1,6mMemFLPAPrn) represented by the above structural formula (viii) were co-evaporated to a thickness of 25 nm, to have a weight ratio of 1:0.05 (=PcgDBCPhA: 1,6mMemFLPAPrn), whereby the light-emitting layer 113 was formed.

After that, over the light-emitting layer 113, PcgDBCPhA was evaporated to a thickness of 10 nm, and 2,9-bis(naphthalen-2-yl)-4,7-diphenyl-1,10-phenanthroline (abbreviation: NBPhen) represented by the above structural formula (xiii) was evaporated to a thickness of 15 nm, whereby the electron-transport layer 114 was formed.

After the formation of the electron-transport layer 114, lithium fluoride (LiF) was evaporated to a thickness of 1 nm to form the electron-injection layer 115, and aluminum was evaporated to a thickness of 200 nm to form the second electrode 102, whereby the light-emitting device 5 of this example was fabricated.

The device structure of the light-emitting device 5 is listed in the following table.

TABLE 7

| | Hole-injection layer | Hole-transport layer | Light-emitting layer | Electron-transport layer | | Electron-injection layer |
|---|---|---|---|---|---|---|
| | 10 nm | 30 nm | 25 nm | 10 nm | 15 nm | 1 nm |
| Light-emitting device 5 | PCzPA: MoOx (4:2) | PCzPA | PcgDBCPhA: 1,6mMemFLPAPrn (1:0.05) | PcgDBCPhA | NBPhen | LiF |

The light-emitting device 5 was subjected to sealing with a glass substrate (a sealant was applied to surround the device, followed by UV treatment and one-hour heat treatment at 80° C. at the time of sealing) in a glove box containing a nitrogen atmosphere so that the light-emitting device is not exposed to the air, and then the initial characteristics and reliability of this light-emitting device were measured. Note that the measurement was carried out at room temperature.

Figures 41, 42:
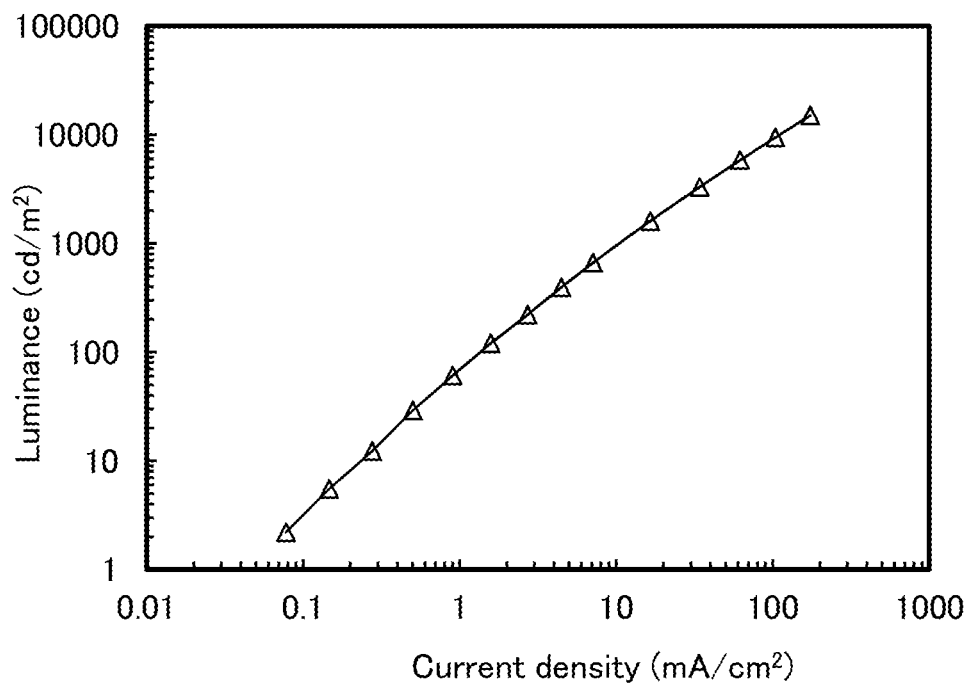
FIG. 41 is luminance-current density characteristics of a light-emitting device 5.
FIG. 42 is current efficiency-luminance characteristics of the light-emitting device 5.
Figure 43:
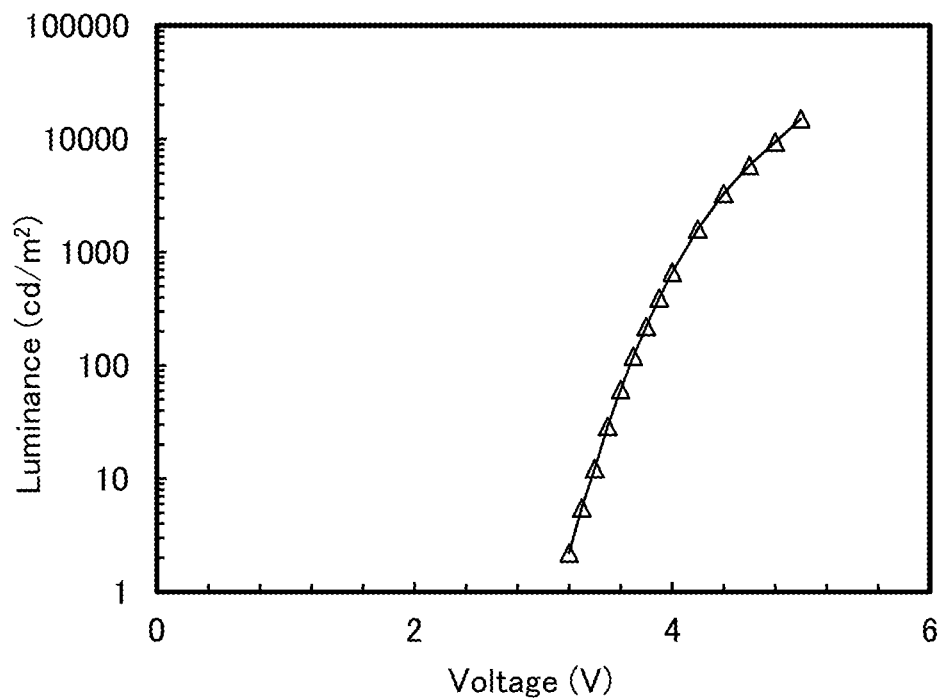
FIG. 43 is luminance-voltage characteristics of the light-emitting device 5.
Figure 44:
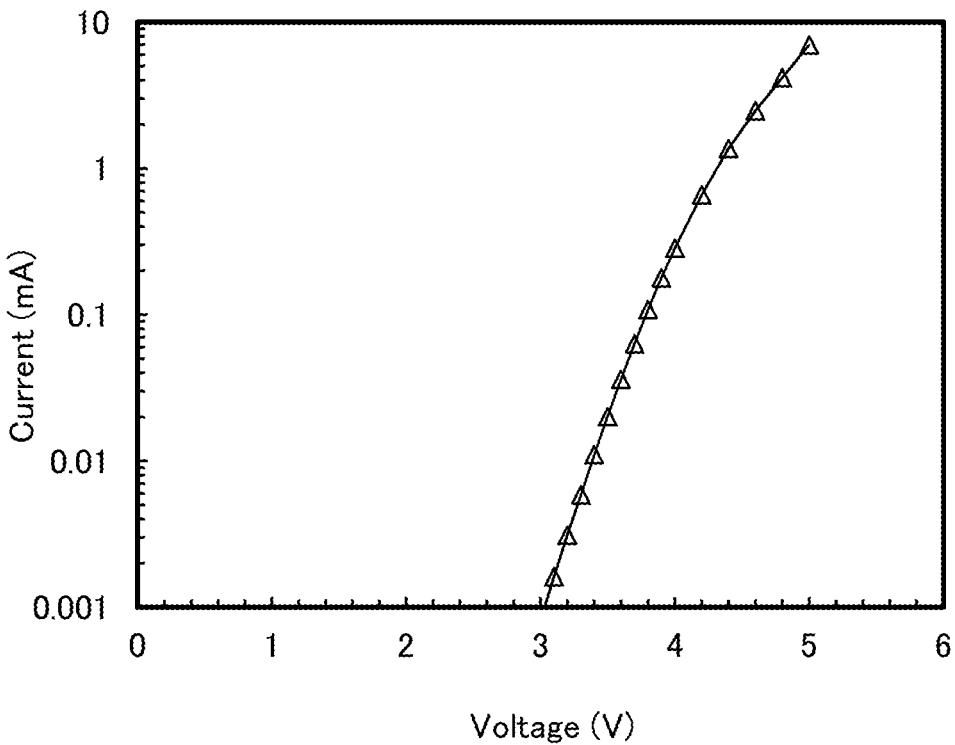
FIG. 44 is current-voltage characteristics of the light-emitting device 5.
Figure 45:
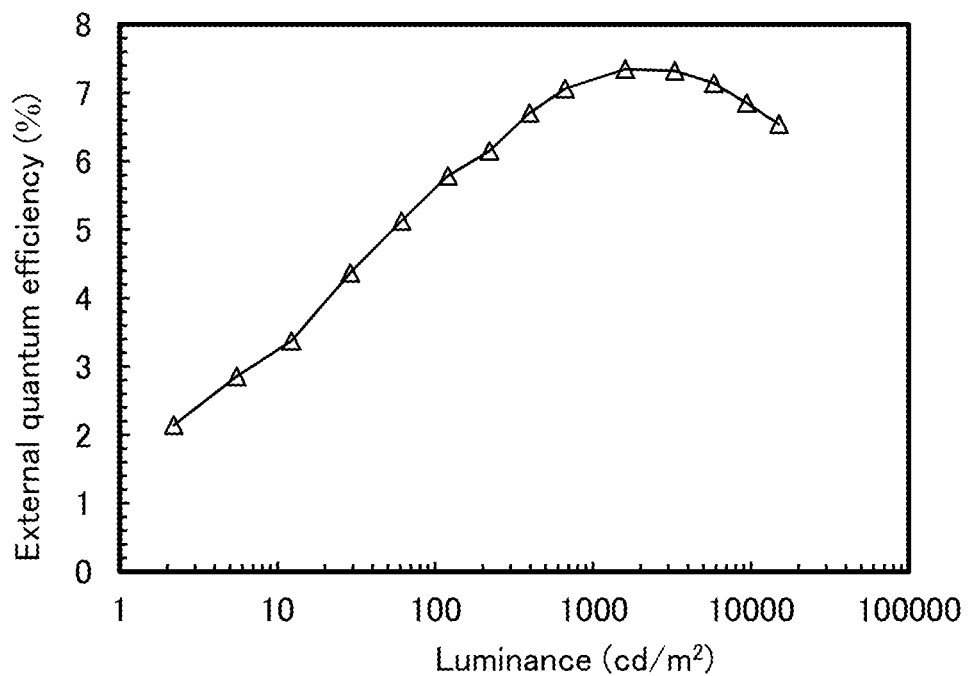
FIG. 45 is external quantum efficiency-luminance characteristics of the light-emitting device 5.
Figure 46:
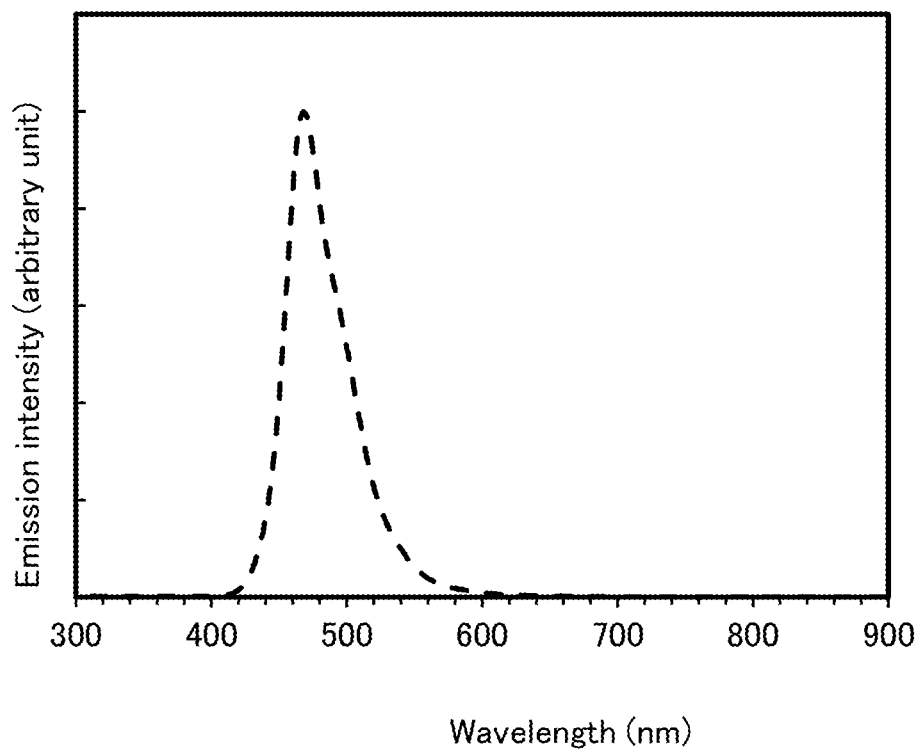
FIG. 46 is an emission spectrum of the light-emitting device 5.

FIG. 41 shows the luminance-current density characteristics of the light-emitting device 5; FIG. 42, the current efficiency-luminance characteristics; FIG. 43, the luminance-voltage characteristics; FIG. 44, the current-voltage characteristics; FIG. 45, the external quantum efficiency-luminance characteristics; and FIG. 46, the emission spectrum. In addition, Table 8 shows the main characteristics of the light-emitting device at around 1000 cd/m$^2$.

TABLE 8

| | Voltage (V) | Current (mA) | Current density (mA/cm$^2$) | Chromaticity x | Chromaticity y | Current efficiency (cd/A) | External quantum efficiency (%) |
|---|---|---|---|---|---|---|---|
| Light-emitting device 5 | 4.0 | 0.28 | 7.1 | 0.14 | 0.19 | 9.3 | 7.1 |

It was found from FIG. 41 to FIG. 46 and Table 8 that the light-emitting device 5 of one embodiment of the present invention was a blue light-emitting device with favorable characteristics.

REFERENCE NUMERALS

101: first electrode, 102: second electrode, 103: EL layer, 111: hole-injection layer, 112: hole-transport layer, 112-1: first hole-transport layer, 112-2: second hole-transport layer, 112-3: third hole-transport layer, 113: light-emitting layer, 114: electron-transport layer, 115: electron-injection layer, 116: charge generation layer, 117: P-type layer, 118: electron-relay layer, 119: electron-injection buffer layer, 400: substrate, 401: first electrode, 403: EL layer, 404: second electrode, 405: sealant, 406: sealant, 407: sealing substrate, 412: pad, 420: IC chip, 501: anode, 502: cathode, 511: first light-emitting unit, 512: second light-emitting unit, 513: charge generation layer, 601: driver circuit portion (source line driver circuit), 602: pixel portion, 603: driver circuit portion (gate line driver circuit), 604: sealing substrate, 605: sealant, 607: space, 608: wiring, 609: FPC (flexible printed circuit), 610: element substrate, 611: switching FET, 612: current control FET, 613: first electrode, 614: insulator, 616: EL layer, 617: second electrode, 618: light-emitting device, 951: substrate, 952: electrode, 953: insulating layer, 954: partition layer, 955: EL layer, 956: electrode, 1001 substrate, 1002 base insulating film, 1003 gate insulating film, 1006 gate electrode, 1007 gate electrode, 1008 gate electrode, 1020 first interlayer insulating film, 1021 second interlayer insulating film, 1022 electrode, 1024W first electrode, 1024R first electrode, 1024G first electrode, 1024B first electrode, 1025 partition, 1028 EL layer, 1029 second electrode, 1031 sealing substrate, 1032 sealant, 1033 transparent base material, 1034R red coloring layer, 1034G green coloring layer, 1034B blue coloring layer, 1035 black matrix, 1036 overcoat layer, 1037 third interlayer insulating film, 1040 pixel portion, 1041 driver circuit portion, 1042 peripheral portion, 2001: housing, 2002: light source, 2100: robot, 2110: arithmetic device, 2101: illuminance sensor, 2102: microphone, 2103: upper camera, 2104: speaker, 2105: display, 2106: lower camera, 2107: obstacle sensor, 2108: moving mechanism, 3001: lighting device, 5000: housing, 5001: display portion, 5002: second display portion, 5003: speaker, 5004: LED lamp, 5006: connection terminal, 5007: sensor, 5008: microphone, 5012: support, 5013: earphone, 5100: cleaning robot, 5101: display, 5102: camera, 5103: brush, 5104: operation button, 5150: portable information terminal, 5151: housing, 5152: display region, 5153: bend portion, 5120: dust, 5200: display region, 5201: display region, 5202: display region, 5203: display region, 7101: housing, 7103: display portion, 7105: stand, 7107: display portion, 7109: control key, 7110: remote controller, 7201: main body, 7202: housing, 7203: display portion, 7204: keyboard, 7205: external connection port, 7206: pointing device, 7210: second display portion, 7401: housing, 7402: display portion, 7403: operation button, 7404: external connection port, 7405: speaker, 7406: microphone, 9310: portable information terminal, 9311: display panel, 9313: hinge, 9315: housing This application is based on Japanese Patent Application Serial No. 2017-225741 filed with Japan Patent Office on Nov. 24, 2017, the entire contents of which are hereby incorporated herein by reference.

The invention claimed is:

1. A dibenzo[c,g]carbazole derivative represented by a general formula (G2),

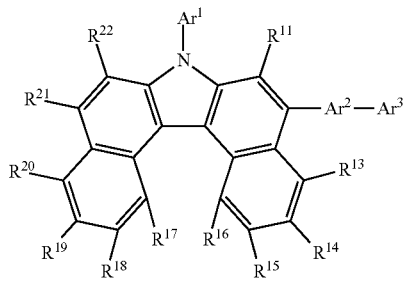

(G2)

wherein:

R$^{11}$ and R$^{13}$ to R$^{22}$ independently represent any of hydrogen, an alkyl group having 1 to 6 carbon atoms, a cycloalkyl group having 3 to 6 carbon atoms, and a substituted or unsubstituted aryl group having 6 to 13 carbon atoms;

Ar$^1$ represents a substituted or unsubstituted aryl group having 6 to 13 carbon atoms in a ring;

Ar$^2$ represents a substituted or unsubstituted arylene group having 6 to 25 carbon atoms in a ring;

Ar$^3$ represents any one of a substituted or unsubstituted naphthyl group, a substituted or unsubstituted anthryl group, a substituted or unsubstituted phenanthryl group and a substituted or unsubstituted triphenylenyl group; and the total number of carbon atoms contained in Ar$^2$ and Ar$^3$ is greater than or equal to 14 and less than or equal to 60.

2. A dibenzo[c,g]carbazole derivative represented by a general formula (G3),

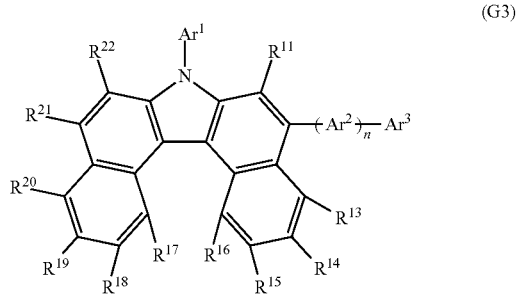

(G3)

wherein:

Ar$^2$ represents a substituted or unsubstituted arylene group having 6 to 25 carbon atoms in a ring;

Ar$^3$ represents any one of a substituted or unsubstituted anthryl group, a substituted or unsubstituted phenanthryl group, and a substituted or unsubstituted triphenylenyl group;

n represents an integer of 1 to 3;

the total number of carbon atoms contained in Ar$^2$ and Ar$^3$ is greater than or equal to 14 and less than or equal to 60;

R$^{11}$ and R$^{13}$ to R$^{22}$ independently represent any of hydrogen, the alkyl group having 1 to 6 carbon atoms, the cycloalkyl group having 3 to 6 carbon atoms, and the substituted or unsubstituted aryl group having 6 to 13 carbon atoms; and Ar$^1$ represents the substituted or unsubstituted aryl group having 6 to 13 carbon atoms in a ring.

3. The dibenzo[c,g]carbazole derivative according to claim 2, wherein n is 1.

4. The dibenzo[c,g]carbazole derivative according to claim 1, wherein Ar$^2$ is a substituted or unsubstituted phenylene group.

5. The dibenzo[c,g]carbazole derivative according to claim 4, wherein Ar$^3$ is an anthryl group comprising a phenyl group as a substituent.

6. The dibenzo[c,g]carbazole derivative according to claim 4, wherein Ar$^3$ is a phenanthryl group.

7. The dibenzo[c,g]carbazole derivative according to claim 1, wherein Ar$^1$ is a substituted or unsubstituted phenyl group.

8. The dibenzo[c,g]carbazole derivative according to claim 1, wherein $R^{11}$ and $R^{13}$ to $R^{22}$ are each hydrogen.

9. A dibenzo[c,g]carbazole derivative represented by a structural formula (100)

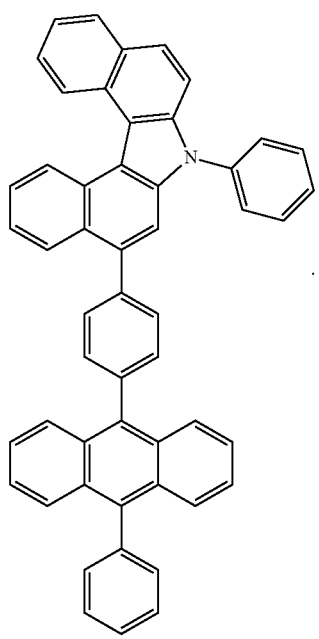

(100)

10. A dibenzo[c,g]carbazole derivative represented by a structural formula (101)

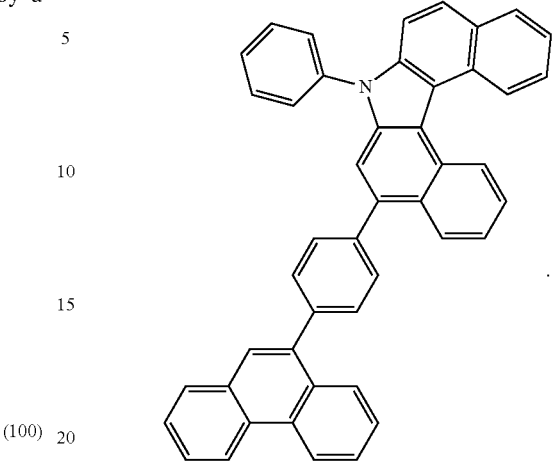

(101)

11. A material for a light-emitting device comprising the dibenzo[c,g]carbazole derivative according to claim 1.

12. A light-emitting device comprising the dibenzo[c,g]carbazole derivative according to claim 1.

13. An electronic device comprising:
   the light-emitting device according to claim 12; and
   at least one of a sensor, an operation button, a speaker, and a microphone.

14. A light-emitting apparatus comprising:
   the light-emitting device according to claim 12; and
   at least one of a transistor and a substrate.

15. A lighting device comprising:
   the light-emitting apparatus according to claim 14; and
   a housing.

16. The dibenzo[c,g]carbazole derivative according to claim 2, wherein $Ar^2$ is a substituted or unsubstituted phenylene group.

17. The dibenzo[c,g]carbazole derivative according to claim 16, wherein $Ar^3$ is an anthryl group comprising a phenyl group as a substituent.

18. The dibenzo[c,g]carbazole derivative according to claim 16, wherein $Ar^3$ is a phenanthryl group.

19. The dibenzo[c,g]carbazole derivative according to claim 2, wherein $R^{11}$ and $R^{13}$ to $R^{22}$ are each hydrogen.

* * * * *